US010689460B2

(12) United States Patent
Imran et al.

(10) Patent No.: US 10,689,460 B2
(45) Date of Patent: Jun. 23, 2020

(54) PCSK9 ANTIBODY PREPARATIONS FOR DELIVERY INTO A LUMEN OF THE INTESTINAL TRACT USING A SWALLOWABLE DRUG DELIVERY DEVICE

(71) Applicant: Incube Labs, LLC, San Jose, CA (US)

(72) Inventors: Mir Imran, Los Altos Hills, CA (US); Radhika Korupolu, Fremont, CA (US); Elaine To, Santa Clara, CA (US); Joel Harris, Mountain View, CA (US); Mir Hashim, Fremont, CA (US)

(73) Assignee: Incube Labs, LLC, San Jose, CA (US)

(*) Notice: Subject to any disclaimer, the term of this patent is extended or adjusted under 35 U.S.C. 154(b) by 315 days.

(21) Appl. No.: 15/260,260

(22) Filed: Sep. 8, 2016

(65) Prior Publication Data

US 2017/0066841 A1 Mar. 9, 2017
US 2019/0062451 A9 Feb. 28, 2019

Related U.S. Application Data

(63) Continuation-in-part of application No. 15/150,379, filed on May 9, 2016, which is a continuation-in-part of application No. 14/714,136, filed on May 15, 2015, now Pat. No. 10,039,810.

(60) Provisional application No. 62/215,586, filed on Sep. 8, 2015, provisional application No. 62/159,134, filed on May 8, 2015, provisional application No. 61/993,907, filed on May 15, 2014, provisional application No. 62/156,105, filed on May 1, 2015.

(51) Int. Cl.
*C07K 16/40* (2006.01)
*A61K 39/00* (2006.01)

(52) U.S. Cl.
CPC ........ *C07K 16/40* (2013.01); *A61K 2039/505* (2013.01); *A61K 2039/54* (2013.01); *A61K 2039/542* (2013.01); *A61K 2039/545* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| 2010/0063557 | A1  | 3/2010 | Imran |            |
|---|---|---|---|---|
| 2011/0160699 | A1* | 6/2011 | Imran | A61K 31/155 604/514 |
| 2013/0165859 | A1  | 6/2013 | Imran |            |
| 2014/0221912 | A1  | 8/2014 | Imran et al. |  |
| 2015/0231236 | A1* | 8/2015 | Pordy et al. | A61K 39/3955 424/142.1 |

FOREIGN PATENT DOCUMENTS

WO   WO-2013008185 A1   1/2013
WO   WO-2016183040 A1   11/2016

OTHER PUBLICATIONS

Schwartz et al. Alirocumab and Cardiovascular Outcomes after Acute Coronary Syndrome. NEJM, 2018; 379(22):2097-107 (Year: 2018).*
Paul. Fundamental Immunology, 3rd Edition, Raven Press, New York, Chapter 8, pp. 292-295, 1993 (Year: 1993).*
MacCallum et al. Antibody-antigen Interactions: Contact Analysis and Binding Site Topography. Journal of Molecular Biology, 262: 732-745, 1996 (Year: 1996).*
Vajdos et al. Comprehensive Functional Maps of the Antigen-binding Site of an Anti-ErbB2 Antibody Obtained with Shotgun Scanning Mutagenesis. Journal of Molecular Biology, Jul. 5, 2002; 320(2):415-28 (Year: 2002).*
Bandyopadhyay et al. Cardiovascular Outcomes of PCSK9 Inhibitors: With Special Emphasis on Its Effect beyond LDL-Cholesterol Lowering. Journal of Lipids, 2018; Article ID 3179201:1-13 (Year: 2018).*
Ma. Animal models of disease. Modern Drug Discovery 2004, 7(6): 30-36 (Year: 2004).*
"International search report with written opinion dated Jan. 9, 2017 for PCT/US16/50832".
Chen, et al., Systematic synergy modeling: understanding drug synergy from a systems biology perspective. BMC Systems Biology. 2015. 9:56.
Co-pending U.S. Appl. No. 15/150,379, filed May 9, 2016.
Jin, et al., An enhanced Petri-net model to predict synergistic effects of pairwise drug combinations from gene microarray data. Bioinformatics. 27(13). 2011.
U.S. Appl. No. 12/556,524, filed Sep. 9, 2009.

(Continued)

*Primary Examiner* — Vanessa L. Ford
*Assistant Examiner* — Sandra E Dillahunt
(74) *Attorney, Agent, or Firm* — Wilson Sonsini Goodrich and Rosati, P.C.

(57) ABSTRACT

Embodiments provide swallowable devices, preparations and methods for delivering therapeutic agents (TAs) within the GI tract such as antibodies (AP-antibodies) or other proteins which neutralize PCSK9 molecules. Many embodiments provide a swallowable device e.g., a capsule for delivering TAs into the intestinal wall (IW). Embodiments also provide TA preparations that are configured to be contained within the capsule, advanced from the capsule into the IW and/or peritoneum and degrade to release the TA into the bloodstream to produce a therapeutic effect. The preparation can be operably coupled to delivery means having a first configuration where the preparation is contained in the capsule and a second configuration where the preparation is advanced out of the capsule into the IW. Embodiments are particularly useful for delivery of AP-antibodies and related TA's for the treatment of cholesterol, lipid and related conditions where such TAs are poorly absorbed and/or degraded within the GI tract.

39 Claims, 48 Drawing Sheets

(56) References Cited

OTHER PUBLICATIONS

Z-Lunven—A randomized study of the relative pharmacokinetics, pharmacodynamics, and safety of alirocumab, a fully human monoclonal antibody to PCSK9, after single subcutaneous administration at three different injection sites in healthy subjects. Cardiovascular Therapeutics. 2014.
EP16845073.2 The Extended European Search Report dated Apr. 23, 2019.

* cited by examiner

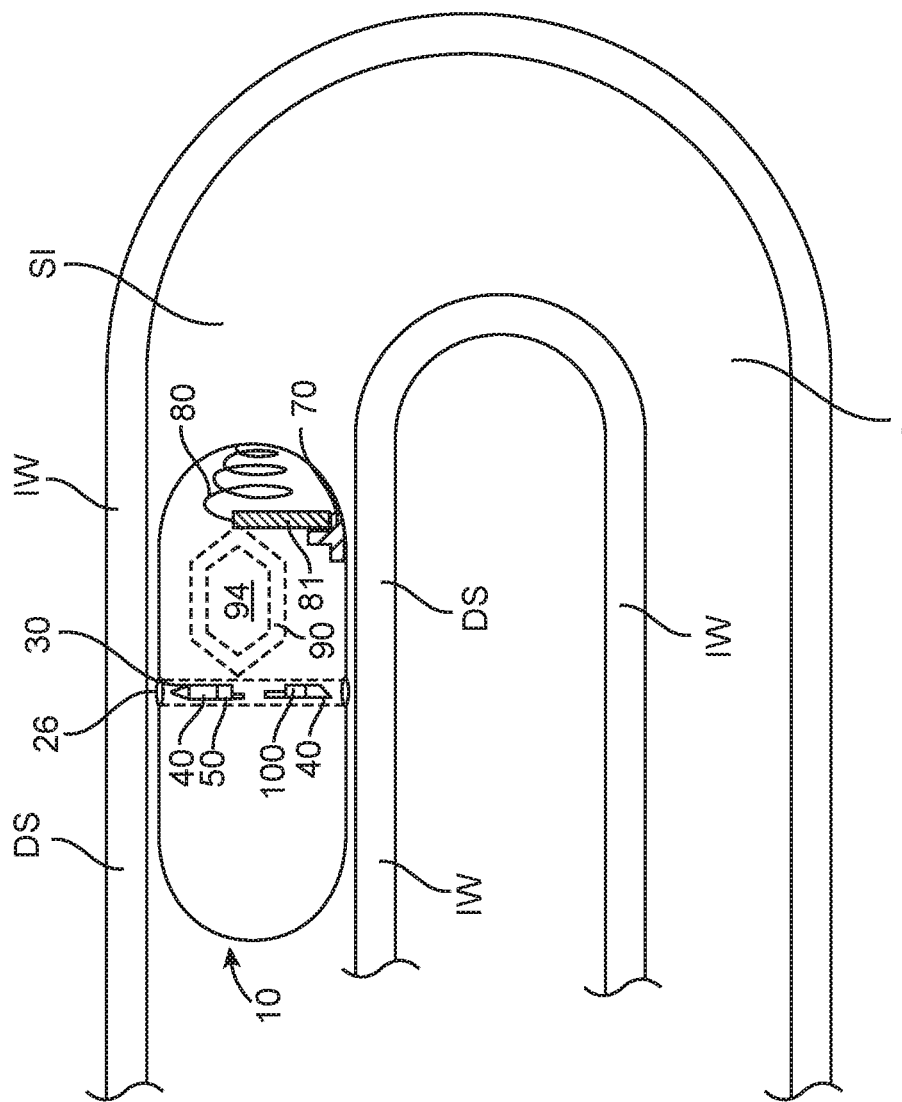

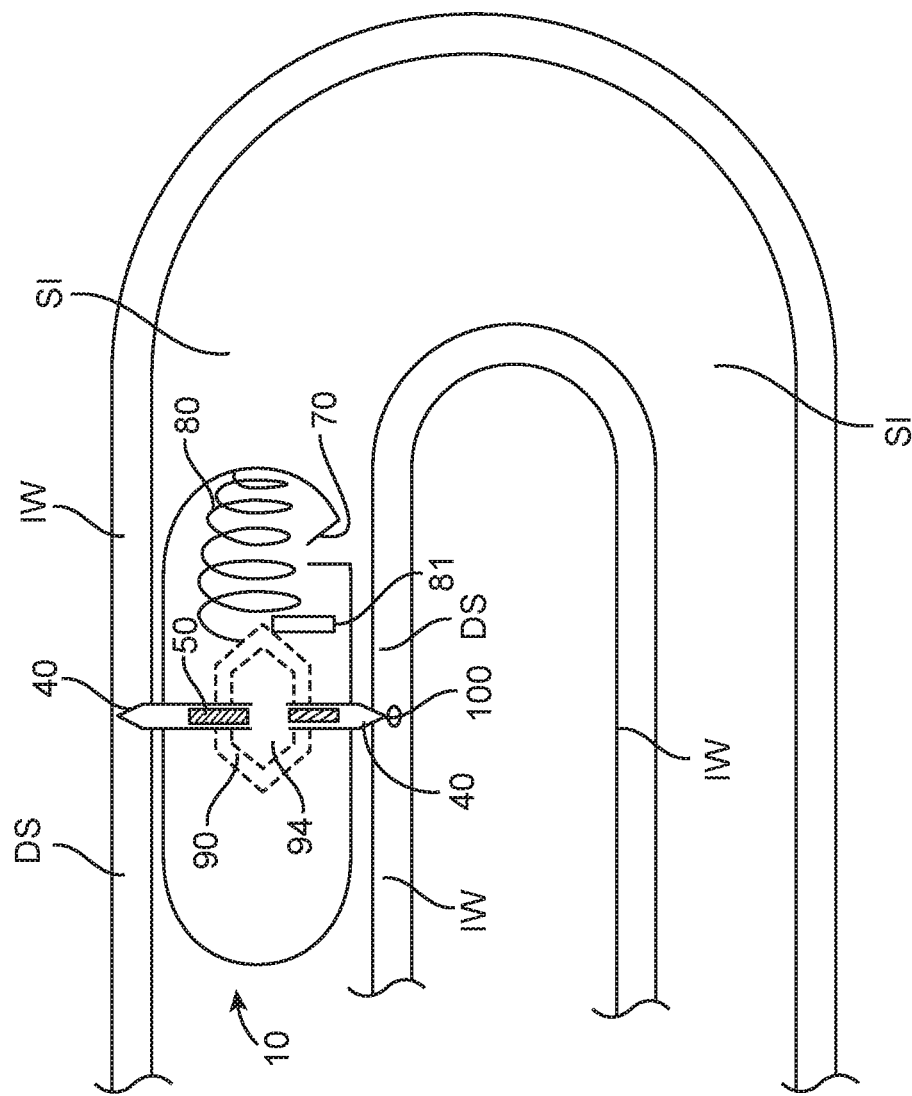

Deglutition

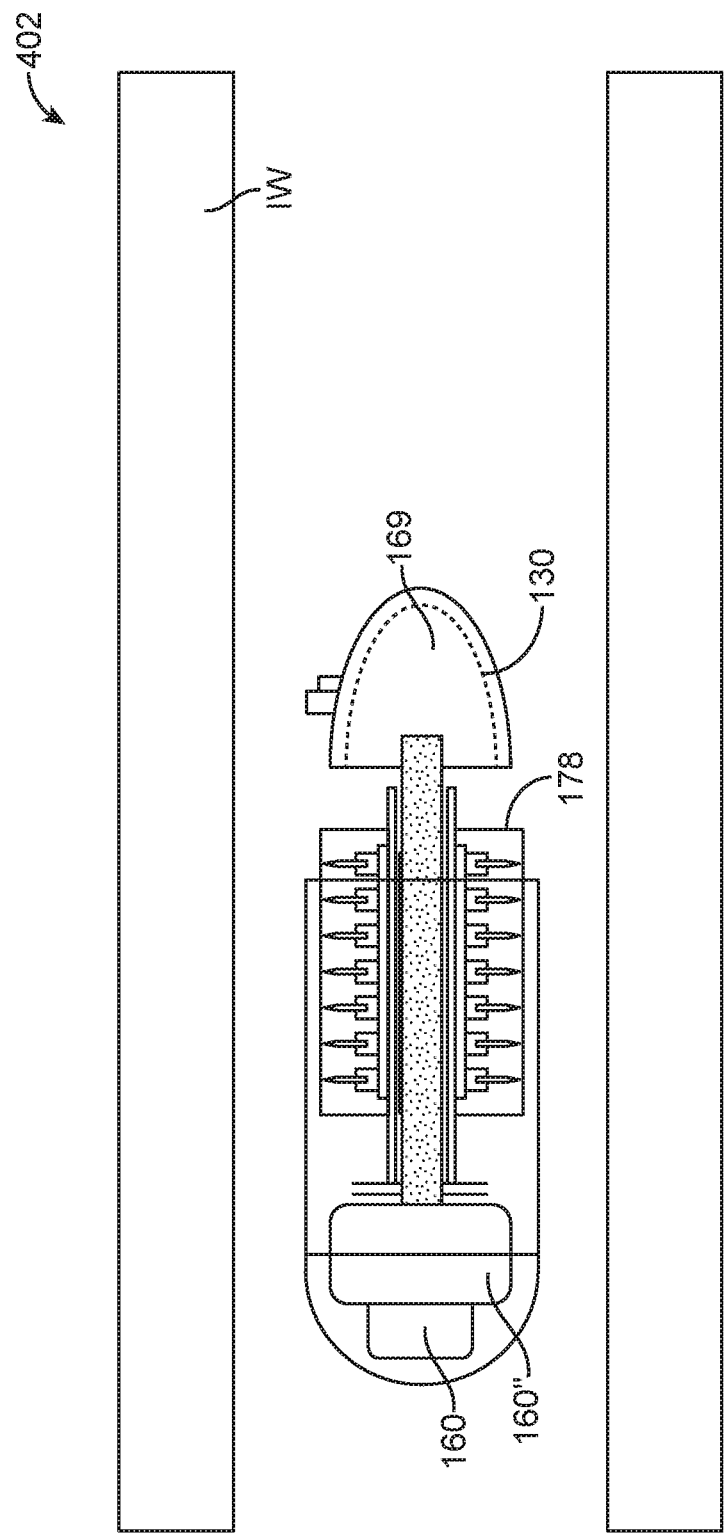

Figure 21  Drugs targeting PCSK-9 for treatment of hypercholesterolemia, dyslipidemia and atherosclerosis

| Type/Generic name | Brand name | Company | Dose Range | Dose Frequency | Route | molecular wt | other info |
|---|---|---|---|---|---|---|---|
| Monoclonal Antibodies | | | | | | | |
| Alirocumab | Praluent | Regeneron/Sanofi | 75mg/150mg/300mg | 75mg/150- every 2-week; 150mg/300mg-every 4-week (clinical studies) | s.c | 146KDa | Approved |
| Evolocumab | Repatha | Amgen | 140mg/420 mg | 140 biweekly, 420 mg monthly (Clinical studies) | S.C | 141.8 Kda | Phase III |
| Bococizumab | | Pfizer | 150mg/300mg | 150 mg- twice monthly and 300 mg once monthly (clinical studies) | S.C | 145.1 Kda | Phase III ongoing |
| RG7652 | | Roche/Genentech | | | | | Phase II |
| LGT-209 | | Novartis | | | | | Phase II |
| 1D05-IgG2 | | Merck | | | | | Preclinical |
| 1B20 | | Merck | | | | | Preclinical |
| J10,J16,J17 | | Pfizer | | | | | Preclinical |
| Adnectins | | | | | | | |
| BMS-962476 | | BMS/Adnexus | | | | | Phase I |
| Mimetic Peptides | | | | | | | |
| EGF-AB peptide frangment | | Schering-Plough | | | | | |
| LDLR Subfragment | | US NIH | | | | | |
| LDLR DNA Construct | | US NIH | | | | | |
| Small molecule inhibitors | | | | | | | |
| SX-PCK9 | | Serometrix | | | | | |
| TBD | | Schifa Biomedical | | | | | |
| Antisense Oligonucleotides | | | | | | | |
| ISIS394814 | | Isis | | | | | |
| SPC 4061 | | Santasis-Pharma | | | | | |
| SPC 5011 | | Santasis-Pharma | | | | | |
| RNAi | | | | | | | |
| ALN-PCS02 | | Alnylam | | | | | |

Figure 22a: Simulated Human Plasma Concentration Profile for Alirocumab delivered as an injected 150mg dose every two weeks days.
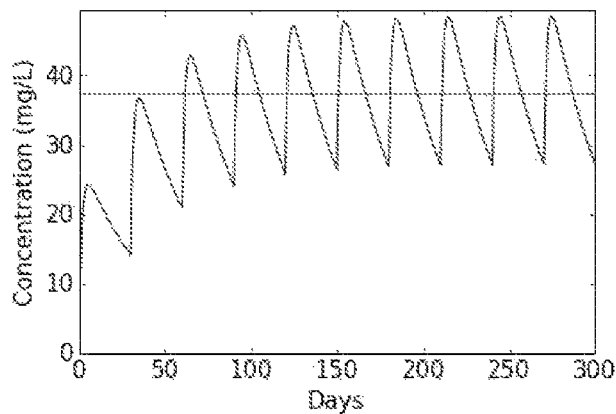
Figure 22b: Simulated Human Plasma Concentration Profile for Alirocumab delivered daily as a 10.5 mg dose using swallowable device embodiments of the invention.
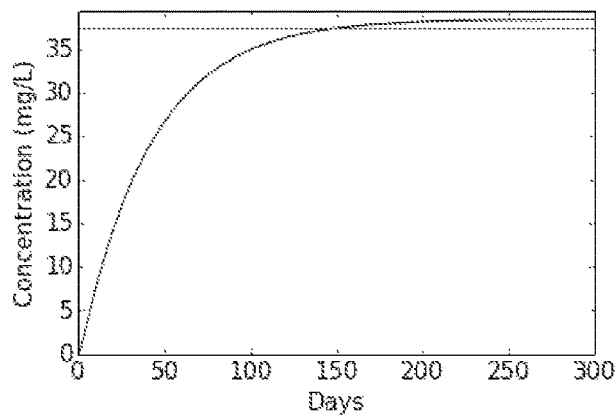

PCSK9 ANTIBODY PREPARATIONS FOR DELIVERY INTO A LUMEN OF THE INTESTINAL TRACT USING A SWALLOWABLE DRUG DELIVERY DEVICE

CROSS-REFERENCES TO RELATED APPLICATIONS

This application claims the benefit of priority to U.S. Provisional Application No. 62/215,586, filed Sep. 8, 2015, the entire content of which is incorporated herein by reference for all purposes. This application is also a continuation-in-part of U.S. patent application Ser. No. 15/150,379, filed May 9, 2016, which is a continuation-in-part of U.S. patent application No. 14/714,136, filed May 15, 2015, which each claim the benefit of priority to U.S. Provisional Application No. 61/933,907, filed May 15, 2014, U.S. Provisional Application No. 62/156,105, filed May 1, 2015, and U.S. Provisional Application No. 62/159,134, filed May 8, 2015, the entire contents of which are incorporated by reference herein for all purposes.

This application incorporates by reference the following U.S. Patent and provisional patent applications for all purposes. Provisional U.S. Patent Application Ser. No. 61/571,642, entitled "Therapeutic Agent Preparation for Delivery Into a Lumen of The Intestinal Tract Using a Swallowable Drug Delivery Device", filed on Jun. 29, 2011; and U.S. Provisional Application No. 61/571,641, entitled "Device, System and Method for the Oral of Therapeutic Compounds", filed Jun. 29, 2011, both of which are fully incorporated by reference herein for all purposes; and this application is also a continuation in part of the following U.S. patent application Ser. No. 12/978,233, entitled "Swallowable Drug Delivery Device and Methods of Drug Delivery", filed on Dec. 23, 2010; U.S. patent application Ser. No. 12/978,164, entitled "Therapeutic Agent Preparation for Delivery Into a Lumen of The Intestinal Tract Using a Swallowable Drug Delivery Device", filed on Dec. 23, 2010; U.S. patent application Ser. No. 12/978,301, entitled "Swallowable Drug Delivery Device and Methods of Drug Delivery", filed on Dec. 23, 2010. U.S. patent application Ser. No. 13/532,589, entitled "Device, System And Methods For The Oral Delivery Of Therapeutic Compounds" filed on Jun. 25, 2012; U.S. Pat. No. 8,809,269, entitled "Therapeutic Agent Preparations for Delivery into A Lumen of the Intestinal Tract using a Swallowable Drug Delivery Devices"; U.S. Provisional Patent Application Ser. No. 61/993,907, entitled, "Pharmaceutical Compositions And Methods For Fabrication Of Solid Masses Comprising Polypeptides And/Or Proteins" filed on May 15, 2014; U.S. Provisional Patent Application Ser. No. 62/156,105, entitled, "Pharmaceutical Compounds And Methods For Fabrication Of Solid Masses Comprising Polypeptides And/Or Proteins, Filed May 1, 2015; and U.S. Provisional Patent Application Ser. No. 62/159,134 entitled "Anti-Interleukin Antibody Preparations For Delivery Into A Lumen Of The Intestinal Tract Using A Swallowable Drug Delivery Device" filed May 8, 2015.

BACKGROUND OF THE INVENTION

Field of the Invention

Embodiments of the invention relate to orally deliverable drug and other therapeutic agent formulations and swallowable drug delivery devices for delivery those formulations to the small intestine. More specifically, embodiments of the invention relate to orally deliverable drug formulations such as antibodies to PCSK9. Still more specifically, embodiments of the invention relate to orally deliverable solid drug formulations such as antibodies to PCSK9.

While there has been an increasing development of new drugs in recent years for the treatment of a variety of diseases, many have limited application because they cannot be given orally. This is due to a number of reasons including: poor oral toleration with complications including gastric irritation and bleeding; breakdown/degradation of the drug compounds in the stomach; and poor, slow or erratic absorption of the drug. Conventional alternative drug delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other drug delivery approaches have been employed such as implantable drug delivery pumps, these approaches require the semi-permanent implantation of a device and can still have many of the limitations of IV delivery. Thus, there is a need for an improved method for delivery of drugs and other therapeutic agents, including a need for improved delivery of antibodies for treatment of cardiovascular and other conditions.

Elevated plasma levels of LDL (low density lipoprotein, cholesterol including LDL-C) a condition known as hypercholesterolemia) has been shown to be a key risk factor for the development of atherosclerosis and associated ischemic cardiovascular disease (CVD), such as myocardial infarction and stroke which are the leading cause of death in the US. High plasma levels of LDL-C levels are highly inheritable and a number of molecular defects have been shown to cause such high levels. One of the pivotal factors in LDL metabolism is the LDL receptor (LDLR). This is due to its capacity to bind and subsequently clear LDL derived cholesterol derived from the circulation. LDL bound to the LDLR is internalized into clathrin-coated pits and subsequently undergoes lysosomal degradation. The LDLR is then recycled back to the plasma membrane where it can bind more LDL. Internalization and re-shuttling of the receptor towards the plasma membrane is a continuous process. The molecule Proprotein convertase subtilisin kexin type 9 (PCSK9) plays a pivotal role in this process since it promotes the degradation of the LDLR and prevents it from recycling to the membrane. PCSK9 specifically acts by reducing the amount of LDLR at the cell surface of hepatocytes. This was first demonstrated in mouse models and inferred by human genetic studies. Numerous overexpression and knockdown/knockout animal studies clearly show that PCSK9 targets the LDLR for degradation. In particular, a series of parabiosis experiments showing that PCSK9 is secreted from liver cells, circulates in the plasma, binds to LDLR, and is subsequently internalized together with the LDLR, thereby promoting the cellular degradation of the receptor.

While antibodies to PCSK9 have been developed as a possible treatment for hypercholesterolemia, the antibodies must be delivered by subdermal injections in biweekly doses or even longer intervals. There a number of drawbacks to this approach. These include giving the patient extremely high doses of the antibodies exposing them to the possibility of one or more allergic reactions (e.g., anaphylactic shock, edema, difficulty breathing, fever, etc.) or other adverse event as well as the development of an immunogenic reaction to the antibodies (e.g. the development by the patient of antibodies to the PCSK9 antibodies, as well as erythema and other adverse reaction the injection cite). They also require the patient to come into the hospital every week to two weeks for the shot. Oral delivery does not have many of these complications as the doses can be delivered in much smaller amounts which do not cause these adverse events. However, currently antibodies such as PCSK9 antibodies cannot be delivered orally as the acids and enzymes in the intestinal tract such a various proteases would break down the antibodies before they are able to be absorbed into the small intestine. What is needed therefore, are compositions and methods for delivering these antibodies orally and in smaller more frequent doses (e.g. daily) but to do so in a manner which does not cause degradation of the antibodies before they are taken up into the wall of the small intestine.

BRIEF SUMMARY OF THE INVENTION

Embodiments of the invention provide devices, systems, kits and methods for delivering drugs and other therapeutic agents to various locations in the body. Many embodiments provide a swallowable device for delivering drugs and other therapeutic agents within the Gastrointestinal (GI) tract. Particular embodiments of the invention provide a swallowable device such as a capsule for delivering drugs and other therapeutic agents into the wall of the small intestine and/or surrounding tissue (e.g. the peritoneum) or other GI organ wall. Embodiments of the invention are particularly useful for the oral delivery of therapeutic agents such as various PCSK9 neutralizing proteins (PN-protein), particularly antibodies which are poorly absorbed, poorly tolerated and/or degraded within the GI tract. Further, embodiments of the invention can be used to orally deliver such PN proteins including PCSK9 neutralizing antibodies (PN-antibodies, also referred to herein as AP-antibodies) which were previously only capable of being delivered by injection including various non-vascular injected forms of administration such as intramuscular or subcutaneous injection. Moreover, such embodiments can be used to provide an orally delivered treatment for hypercholesterolemia or other cholesterol related disease or condition using PN antibodies (or other PN-proteins) without the side effects associated with subcutaneous injection or other form of injected delivery of these compounds.

In one aspect of the invention, the invention provides a therapeutic agent preparation for delivery into the wall of the small intestine and/or surrounding tissue (e.g. the peritoneum) or other location in the intestinal tract, comprising a therapeutically effective dose of at least one PCSK9 neutralizing protein (PN protein or PNP also known as a PCSK9 binding protein or PB-protein) such as an antibody which binds to PCSK9 molecules (herein anti-PCSK9 antibodies or AP-antibodies) or its receptors along with their respective analogues and derivatives. The AP-antibodies used in one or more embodiments of the therapeutic preparations can be full-length antibodies or an antigen-binding portion thereof. The preparation may have a shape and material consistency to be contained in an embodiment of the swallowable capsule (or like device) and delivered from the capsule into the intestinal wall to release the dose of AP-antibody or other PN-protein from within the intestinal wall. Such shapes may correspond to various structures having a pointed end such as various dart-like, or needle like shapes or structures. The preparation may be in solid, liquid, or powder form. Preferably, the preparation including the AP-antibody or other PN protein is in solid form allowing the preparation to be stored for extended periods of time, as well as to be shaped (e.g. into a tissue penetrating shape) and have a mechanical force or other force exerted against the preparation to insert it into an intestinal wall.

The PN-protein may be selected from an immunoglobulin molecule or functional variants thereof known in the art, with such variants retaining the characteristic binding property of the PCSK9 binding protein. Examples of specific immunoglobulin molecules which may be used include, but are not limited to, an scFv (single chain variable fragment); a monoclonal antibody; a human antibody; a chimeric antibody; a humanized antibody; a single domain antibody; a Fab (fragment antigen binding) fragment; an Fab' fragment; an F(ab')2; an Fv (variable fragment); a disulfide linked Fv, and a bispecific or dual specific antibody. Preferably, the binding protein is a human antibody and/or a monoclonal antibody.

One or more of the immunoglobulin molecules described herein will typically, though not necessarily, comprise 2 heavy (H) chains and 2 light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function. Light chains are classified as kappa or lambda, which are each characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is also characterized by a particular constant region with a sequence well known in the art. "Antigen-binding fragment", as used herein, refers to Fab fragments, Fab' fragments, F(ab')$_2$ fragments, and single chain Fv fragments one more of which bind to human PCSK9. The term "bind (or 'binds') to human PCSK9", as used herein, refers to interaction with an epitope on human PCSK9. The term "epitope" as used herein refers to discrete, three-dimensional sites on an antigen that are recognized by the antibodies or antigen-binding fragments of the invention.

Another aspect of the invention provides a PCSK9 neutralizing protein comprising any one of the binding proteins disclosed herein (e.g., AP-antibodies and AP-antibodies such as Secukinumab) wherein the PCSK9 neutralizing binding protein is capable of neutralizing and/or inhibiting the biologic effects of one more of PCSK9 molecules by preventing or diminishing the ability of the selected PCSK9 from binding to a receptor for that PCSK9. Such a neutralizing effect can be achieved by selecting the binding protein to either: 1) bind to the selected PCSK9 so as prevent or inhibit that PCSK9 from binding to the receptor for that PCSK9 and in turn causing one or more biological effects; or 2) bind to a receptor for that particular PCSK9 so as to prevent the PCSK9 from activating the receptor and causing the one or more biologic effects In many embodiments, the dose of the selected AP-antibody or other PN-protein delivered by embodiments of the swallowable capsule described herein, though it is contemplated that other swallowable devices can be used. The dose of the selected AP-antibody can be titrated to treat a cholesterol or lipid related condition (e.g. hypercholesterolemia, dyslipidemia) while minimizing the adverse effect associated with an injected dose (e.g. intravenous, intramuscular, subcutaneous etc.) of the antibody. Such adverse effects can include without limitation one or more of anaphylactic shock or other allergic reaction (e.g., edema, water eyes, respiratory congestion), immunogenic reaction to the PN-protein (including immunogenic neutralization of the delivered PN-protein by patients own antibodies), headache, fever and other related effect. In particular embodiments, this can be achieved by titrating the delivered dose of AP-antibody or other PN-protein to a daily vs a monthly dose which is typically given for AP-antibodies. For the case of minimizing immune response, this result can also be achieved by delivering the dose of AP-antibodies to the upper or mid portion of the small intestine and avoiding the lower section of the intestine e.g., the ileum containing the Peyer's patches as is discussed in further detail herein. Other benefits of delivering the AP-antibody in smaller doses into the small intestine (vs. by injection) include one or more of the following: i) higher therapeutic ratios; and ii) reduced fluctuation (known as % steady state fluctuation as is described in more detail herein) in the plasma concentration for the AP-antibody or other PN protein.

In another aspect, the invention provides methods for reducing LDL-C levels in a patient having elevated LDL-C levels, comprising administering to the patient a therapeutically effective amount of an AP-antibody using one or more embodiments of the swallowable capsule described herein, thereby reducing LDL-C levels. The invention also provides methods for reducing LDL-C levels in a patient comprising selecting a patient having elevated LDL-C levels (determined by one or more methods known in the art), and administering to the patient a therapeutically effective amount of an AP-antibody using one or more embodiments of the swallowable capsule described herein (or any other swallowable device or pill). LDL-cholesterol levels and or lipids can be monitored to determine the efficacy of treatments in lowering LDL-C levels and if necessary, adjustments can be made in the dosage (e.g. increase of decrease) and/or dose frequency of the administered AP-antibody Related aspects of the invention provide methods for treating atherosclerosis in a patient, comprising: selecting a patient diagnosed with atherosclerosis, administering to the patient a therapeutically effective amount of an AP-antibody using an embodiment of the swallowable capsule descried herein, and monitoring the patient's level of atherosclerosis (e.g. using various imaging modalities and/or via cardiac catheterization). Also provided are methods for reducing coronary heart disease risk, comprising: selecting a patient having elevated LDL-C and/or lipid levels and one or more additional indicators of coronary heart disease, administering to the patient a therapeutically effective amount of an antisense compound targeted to one or more PCSK9 nucleic acids, and monitoring LDL-C levels and/or lipid levels and adjusting the dose of antisense compound accordingly. Additionally, provided are methods for treating hypercholesterolemia, dyslipidemia or other related condition comprising administering to a patient diagnosed with hypercholesterolemia and/or dyslipidemia a therapeutically effective amount of an antisense oligonucleotide targeted to a PCSK9 nucleic acid, thereby reducing cholesterol and/or lipid levels. In these and related embodiments, the AP-antibody may correspond to one more of Alirocumab, Evolocumab or Bococizumab their analogues and derivatives as well as antigen-binding portions thereof. In additional or supplemental embodiments, genetic testing can be performed on the patient prior to AP-antibody administration to determine the most effective of these or other AP antibody to use (and/or those that may have an adverse reaction) and/or the most effective dosage and/or dose frequency.

In another aspect, the invention provides methods for treating a disease or condition associated with the biological activity of a PCSK9 molecule including various forms of dyslipidemia and/or hypercholesterolemia including, without limitation, heterozygous familial hypercholesterolemia, and homozygous familial hypercholesterolemia. The method comprises providing a solid anti-PCSK9 antibody (AP-antibody) dosage shaped as a tissue penetrating member which may be dart like or needle shaped with other shapes and/or structures contemplated as well. The dosage is orally delivered to the small intestine by mean of an orally ingested swallowable capsule or other swallowable device. Once in the small intestine (or other location in the intestinal tract), the solid dosage penetrates and is inserted into the intestinal wall by the application of a mechanical force or other force on the tissue penetrating member such that the tissue penetrating member is retained in the intestinal wall. A therapeutically effective dose of the AP-antibody is then released into the blood stream from the solid dosage AP-antibody in the intestinal wall to inhibit the activity of PCSK9 molecule and thereby treat the diseases or condition. In these and related embodiments, the AP-antibody may correspond to one more of Alirocumab, Evolocumab or Bococizumab as well as antigen-binding portions thereof along with the analogues and derivatives of the aforementioned AP-antibodies.

In other aspects, the invention provides a method for delivering therapeutic agents into the wall of the small intestine and/or surrounding tissue such as the peritoneum comprising swallowing a drug delivery device comprising a capsule, an actuator and an embodiment of the therapeutic agent preparation such as a INP preparation (e.g. a preparation comprising one or more anti-PCSK9 antibodies). The actuator is responsive to a condition in the small intestine such as pH so as to actuate delivery of the therapeutic agent preparation into the wall of the small intestine and/or surrounding tissue such as the wall of the peritoneum. In specific embodiments, the actuator can comprise a release element or coating on the capsule which is degraded by a selected pH in the small intestine. Once degraded, the element or coating initiates delivery of the therapeutic agent preparation by one or more delivery means such as the by expansion of one or more balloons that are operably coupled to tissue penetrating members that contain the therapeutic agent preparation and are configured to penetrate and be advanced into the intestinal wall upon expansion of the balloon. Once the tissue penetrating members are in the intestinal wall, they degrade to release the therapeutic agent into the bloodstream. Because the therapeutic agent preparation is delivered directly into the wall of the small intestine (and or surrounding tissue such as the peritoneum), the time period (described herein as $t_{max}$) for achieving the maximum concentration of the IBO or other therapeutic agent in the bloodstream or other location in the body is shorter than a corresponding time period for achieving such a maximum concentration when the therapeutic agent is non-vascularly injected into the body such as by intramuscular or subcutaneous injection. In various embodiments, the time period for achieving $C_{max}$ by insertion of the therapeutic preparation into the intestinal wall using one or more embodiments of the invention (such as an embodiment of the swallowable device) can be about 80%, 50%, 30%, 20 or even 10% of the time period for achieving a $C_{max}$ through the use of a non-vascular injection of the therapeutic agent. As used herein the term about generally refers to within 5% of the stated value of a number, but in some cases may larger of smaller. In other embodiments, the $C_{max}$ achieved by insertion of the therapeutic preparation into the intestinal wall using one or more embodiments of the invention, such as an embodiment of the swallowable device, can be greater than a $C_{max}$ achieved by taking a conventional oral form of the therapeutic agent (e.g., a pill) where the therapeutic agent is not inserted into the intestinal wall. In various embodiments, the $C_{max}$ achieved by insertion of the therapeutic preparation into the intestinal wall using one or more embodiments of the invention (such as an embodiment of the swallowable device) can be 5, 10, 20, 30, 40, 50, 60, 70, 80 or even a 100 times greater than when the therapeutic agent is delivered in a pill or other oral form. In other related embodiments, the composition can be configured to produce a long-term release of therapeutic agent with a selectable t½, (that is the time period required for the concentration of the therapeutic agent in the bloodstream or other location in the body to reach half its original $C_{max}$ value after having reached $C_{max}$). For example, the selectable t½ may be 6, or 9, or 12, or 15 or 18, or 24 hours.

In another aspect, the invention provides a swallowable device for delivering a drug or other therapeutic agent preparation into the wall of the small or large intestine, peritoneum or other organ of the gastro-intestinal tract organ. The devise comprises a capsule sized to be swallowed and pass through the gastro-intestinal tract, a deployable aligner positioned within the capsule for aligning a longitudinal axis of the capsule with the a longitudinal axis of the small intestine, a delivery mechanism for delivering the therapeutic agent into the intestinal wall and a deployment member for deploying at least one of the aligner or the delivery mechanism. The capsule wall is degradable by contact with liquids in the GI tract but also may include an outer coating or layer which only degrades in the higher pH found in the small intestine, and serves to protect the underlying capsule wall from degradation within the stomach before the capsule reaches the small intestine at which point the drug delivery is initiated by degradation of the coating. In use, such materials allow for the targeted delivery of a therapeutic agent in a selected portion of the intestinal tract such as the small intestine. Suitable outer coatings can include various enteric coatings such as various co-polymers of acrylic acid (a particular example including EUDRAGIT available from EVONIK industries), Methacrylic Acid and Ethyl Acrylate. In particular embodiments, the outer coating can be configured to degrade in the pH found in the upper portion of the small intestine (e.g. the duodenum) or mid portions (jejunum) such that therapeutic agent preparation is delivered into that respective portion and avoids the lower portion of the small intestine (the ileum) containing the Peyer's patches which are aggregated lymphoid nodules which produce macrophages, and other immune related cells. In example of such a coating which degrades in the pH of the duodenum or jejunum can include EUDRAGIT. By delivering the therapeutic agent to a location in the small intestine without Peyer's patches, the generation of immune related cells and subsequent immune response (e.g. generation of various PCSK9s) to the therapeutic agent is minimized. Thus in use, such controlled placement or delivery of the therapeutic agent into the upper or other select portions of the small intestines, eliminates or otherwise minimizes the immune response of the patient to a particular therapeutic agent.

Another embodiment of the capsule includes at least one guide tube, one or more tissue penetrating members positioned in the at least one guide tube, a delivery member and an actuating mechanism. The tissue penetrating member will typically comprise a hollow needle or other like structure and will have a lumen and a tissue penetrating end for penetrating a selectable depth into the intestinal wall. In various embodiments, the device can include a second and a third tissue penetrating member with additional numbers contemplated. Each tissue penetrating member can include the same or a different drug. In preferred embodiments having multiple tissue penetrating members, the tissue penetrating members can be symmetrically distributed around the perimeter of the capsule so as to anchor the capsule onto the intestinal wall during delivery of drug. In some embodiments, all or a portion of the tissue penetrating member (e.g., the tissue penetrating end) can be fabricated from the drug preparation itself. In these and related embodiments, the drug preparation can have a needle, dart-like or other elongated structure with a pointed end (with or without barbs) configured to penetrate and be retained in the intestinal wall.

The tissue penetrating member can be fabricated from various biodegradable materials so as to degrade within the small intestine and thus provide a fail-safe mechanism for detaching the tissue penetrating member from the intestinal wall should this component become retained in the intestinal wall. Such biodegradable materials may correspond to one or more of, PGLA, maltose or other sugar, polyethylene, polyethylene oxide or other biodegradable polymer known in the art. Additionally, in theses and related embodiments, selectable portions of the capsule can be fabricated from such biodegradable materials so as to allow the entire device to controllably degrade into smaller pieces. Such embodiments facilitate passage and excretion of the devices through the GI tract. In particular embodiments, the capsule can include seams of biodegradable material which controllably degrade to produce capsule pieces of a selectable size and shape to facilitate passage through the GI tract. The seams can be pre-stressed, perforated or otherwise treated to accelerate degradation. The concept of using biodegradable seams to produce controlled degradation of a swallowable device in the GI tract can also be applied to other swallowable devices such as swallowable cameras to facilitate passage through the GI tract and reduce the likelihood of a device becoming stuck in the GI tract.

The delivery member is configured to advance the drug from the capsule through the tissue penetrating member lumen and into the intestinal wall. Typically, at least a portion of the delivery member is advanceable within the tissue penetrating member lumen. The delivery member can have a piston or like structure sized to fit within the delivery member lumen. The distal end of the delivery member (the end which is advanced into tissue) can have a plunger element which advances the drug within tissue penetrating member lumen and also forms a seal with the lumen. The plunger element can be integral or attached to the delivery member. Preferably, the delivery member is configured to travel a fixed distance within the needle lumen so as to deliver a fixed or metered dose of drug into the intestinal wall. This can be achieved by one or more of the selection of the diameter of the delivery member (e.g., the diameter can be distally tapered), the diameter of the tissue penetrating member (which can be narrowed at its distal end), use of a stop, and/or the actuating mechanism. For embodiments of the device having a tissue penetrating member fabricated from drug (e.g., a drug dart), the delivery member is adapted to advance the dart out of the capsule and into tissue.

The delivery member and tissue penetrating member can be configured for the delivery of liquid, semi-liquid or solid forms of drug or all three. Solid forms of drug can include both powder or pellet. Semi liquid can include a slurry or paste. The drug can be contained within a cavity of the capsule, or in the case of the liquid or semi-liquid, within an enclosed reservoir. In some embodiments, the capsule can include a first second, or a third drug (or more). Such drugs can be contained within the tissue penetrating member lumen (in the case of solids or powder) or in separate reservoirs within the capsule body.

The actuating mechanism can be coupled to at least one of the tissue penetrating member or the delivery member. The actuating mechanism is configured to advance the tissue penetrating member a selectable distance into the intestinal wall as well as advance the delivery member to deliver the drug and then withdraw the tissue penetrating member from the intestinal wall. In various embodiments, the actuating mechanism can comprise a preloaded spring mechanism which is configured to be released by the release element. Suitable springs can include both coil (including conical shaped springs) and leaf springs with other spring structures also contemplated. In particular embodiments, the spring can be cone shaped to reduce the length of the spring in the compressed state even to the point where the compressed length of the spring is about the thickness of several coils (e.g., two or three) or only one coil.

In particular embodiments, the actuating mechanism comprises a spring, a first motion converter, and a second motion converter and a track member. The release element is coupled to the spring to retain the spring in a compressed state such that degradation of the release element releases the spring. The first motion converter is configured to convert motion of the spring to advance and withdraw the tissue penetrating element in and out of tissue. The second motion converter is configured to convert motion of the spring to advance the delivery member into the tissue penetrating member lumen. The motion converters are pushed by the spring and ride along a rod or other track member which serves to guide the path of the converters. They engage the tissue penetrating member and/or delivery member (directly or indirectly) to produce the desired motion. They are desirably configured to convert motion of the spring along its longitudinal axis into orthogonal motion of the tissue penetrating member and/or delivery member though conversion in other directions is also contemplated. The motion converters can have a wedge, trapezoidal or curved shape with other shapes also contemplated. In particular embodiments, the first motion converter can have a trapezoidal shape and include a slot which engages a pin on the tissue penetrating member that rides in the slot. The slot can have a trapezoidal shape that mirrors or otherwise corresponds to the overall shape of the converter and serves to push the tissue penetrating member during the upslope portion of the trapezoid and then pull it back during the down slope portion. In one variation, one or both of the motion converters can comprise a cam or cam like device which is turned by the spring and engages the tissue penetrating and/or delivery member.

In other variations, the actuating mechanism can also comprise an electro-mechanical device/mechanism such as a solenoid or a piezoelectric device. In one embodiment, the piezoelectric device can comprise a shaped piezoelectric element which has a non-deployed and deployed state. This element can be configured to go into the deployed state upon the application of a voltage and then return to the non-deployed state upon the removal of the voltage. This and related embodiments allow for a reciprocating motion of the actuating mechanism so as to both advance the tissue penetrating member and then withdraw it.

The release element is coupled to at least one of the actuating mechanism or a spring coupled to the actuating mechanism. In particular embodiments, the release element is coupled to a spring positioned within the capsule so as to retain the spring in a compressed state. Degradation of the release element releases the spring to actuate the actuation mechanism. In many embodiments, the release element comprises a material configured to degrade upon exposure to chemical conditions in the small or large intestine such as pH. Typically, the release element is configured to degrade upon exposure to a selected pH in the small intestine, e.g., about 7.0, 7.1, 7.2, 7.3, 7.4, 8.0 or greater. However, it can also be configured to degrade in response to other conditions in the small intestine e.g. osmolality, fluid content of the small intestine contents, viscosity of contents, flora, compressive forces, presence and/or concentration of various bile salts and the line. In particular embodiments, the release element can be configured to degrade in response to particular chemical conditions in the fluids in the small intestine such as those which occur after ingestion of a meal (e.g., a meal high in fats or proteins).

Biodegradation of the release element from one or more conditions (e.g. pH, osmolality, presence of bile salts, etc.) in the small intestine (or other location in the GI tract) can be achieved by selection of the materials for the release element, the amount of cross linking of those materials as well as the thickness and other dimensions of the release elements. Lesser amounts of cross linking and or thinner dimensions can increase the rate of degradation and vice versa. Suitable materials for the release element can comprise biodegradable materials such as various enteric materials which are configured to degrade upon exposure to the higher pH or other condition in the small intestine. The enteric materials can be copolymerized or otherwise mixed with one or more polymers to obtain a number of particular material properties in addition to biodegradation. Such properties can include without limitation stiffness, strength, flexibility and hardness.

In particular embodiments, the release element can comprise a film or plug that fits over or otherwise blocks the guide tube and retains the tissue penetrating member inside the guide tube. In these and related embodiments, the tissue penetrating member is coupled to a spring loaded actuating mechanism such that when the release element is degraded sufficiently, it releases the tissue penetrating member which then springs out of the guide tube to penetrate into the intestinal wall. In other embodiments, the release element can be shaped to function as a latch which holds the tissue penetrating element in place. In these and related embodiments, the release element can be located on the exterior or the interior of the capsule. In the interior embodiments, the capsule and guide tubes are configured to allow for the ingress of intestinal fluids into the capsule interior to allow for the degradation of the release element.

In some embodiments, the actuating mechanism can be actuated by means of a sensor, such as a pH or other chemical sensor which detects the presence of the capsule in the small intestine and sends a signal to the actuating mechanism (or to an electronic controller coupled to the actuating mechanism to actuate the mechanism). Embodiments of a pH sensor can comprise an electrode-based sensor or it can be a mechanically-based sensor such as a polymer which shrinks or expands upon exposure to the pH or other chemical conditions in the small intestine. In related embodiments, an expandable/contractable sensor can also comprise the actuating mechanism itself by using the mechanical motion from the expansion or contraction of the sensor.

According to another embodiment for detecting that the device is in the small intestine (or other location in the GI tract), the sensor can comprise a strain gauge or other pressure/force sensor for detecting the number of peristaltic contractions that the capsule is being subject to within a particular location in the intestinal tract. In these embodiments, the capsule is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments detection of the number of peristaltic contractions can be used to not only determine if the capsule is in the small intestine but the relative location within the intestine as well.

As an alternative or supplement to internally activated drug delivery, in some embodiments, the user may externally activate the actuating mechanism to deliver drug by means of RF (radio frequency), magnetic or other wireless signaling means known in the art. In these and related embodiments, the user can use a handheld device (e.g., a hand held RF device) which not only includes signaling means, but also means for informing the user when the device is in the small intestine or other location in the GI tract. The later embodiment can be implemented by including an RF transmitter on the swallowable device to signal to the user when the device is in the small intestine or other location (e.g., by signaling an input from the sensor). The same handheld device can also be configured to alert the user when the actuating mechanism has been activated and the selected drug(s) delivered. In this way, the user is provided confirmation that the drug has been delivered. In another approach an external acoustical sensor can be used to detect when the actuating mechanism has been activated by detecting sounds unique to the actuating mechanism be activated, for example, by detecting one or more eigen frequency sounds which can occur for embodiments using a chamber including a piston and cylinder mechanism operably coupled to the tissue penetrating member. One or more of the preceding approaches allow the user to take other appropriate drugs/therapeutic agents as well as make other related decisions (e.g., for diabetics to eat a meal or not and what foods should be eaten). The handheld device can also be configured to send a signal to the swallowable device to over-ride the actuating mechanism and so prevent, delay or accelerate the delivery of drug. In use, such embodiments allow the user to intervene to prevent, delay or accelerate the delivery of drug based upon other symptoms and/or patient actions (e.g., eating a meal, deciding to go to sleep, exercise etc.).

The user may also externally activate the actuating mechanism at a selected time period after swallowing the capsule. The time period can be correlated to a typical transit time or range of transit times for food moving through the user's GI tract to a particular location in the tract such as the small intestine. External activation can be done by any number of means including radio control means (e.g. using an RF communication device), magnetic means (e.g. by use of miniature magnetic switch or release built into the swallowable device that the user activates with an external magnetic) or acoustic means (e.g. via an ultrasonic transmission device and an acoustical receive and/or switch built into the swallowable device)

Another aspect of the inventions provides therapeutic agent preparations for delivery into the wall of the small intestine (including surrounding tissue such as the peritoneum) or other wall in the intestinal tract using embodiments of the swallowable device described herein. The preparation comprises a therapeutically effective dose of at least one therapeutic agent such as antibody or other binding protein. Also, it may comprise a solid, liquid or combination of both and can include one or more pharmaceutical excipients. The preparation has a shape and material consistency to be contained in embodiments of the swallowable capsule, delivered from the capsule into the intestinal wall and/or peritoneal wall or other surrounding tissue) and degrade within the intestinal/peritoneal wall to release the dose of therapeutic agent. The preparation may also have a selectable surface area to volume ratio so as enhance or otherwise control the rate of degradation of the preparation in the wall of the small intestine, peritoneal wall or other body lumen. In various embodiments, the preparation can be configured to be coupled to an actuator such as a release element or actuation mechanism which has a first configuration in which the preparation is contained in the capsule and a second configuration in which the preparation is advanced out of the capsule and into the wall of the small intestine and/or peritoneum. The dose of the drug or other therapeutic agent in the preparation can be titrated downward from that which would be required for conventional oral delivery methods so that potential side effects from the drug can be reduced.

Typically, though not necessarily, the preparation will be shaped and otherwise configured to be contained in the lumen of a tissue penetrating member, such as a hollow needle, which is configured to be advanced out of the capsule and into the wall of the small intestine and/or peritoneal wall. The preparation itself may comprise a tissue penetrating member configured to be advanced into the wall of the small intestine and/or peritoneal wall, or other lumen in the intestinal tract. Such configurations of the tissue penetrating member may include various shapes having a pointed tip including for example, needles, darts, and other like shapes. In particular embodiments the tissue penetrating member comprises various elongated shapes having a pointed end. It may also comprise various isometric shapes having a pointed end, such as a triangle, square with pointed end, conical with a pointed end, or hemispherical with a pointed end.

Another aspect of the invention provides methods for the delivery of drugs and the therapeutic agents into the walls of the GI tract using embodiments of the swallowable drug delivery devices. Such methods can be used for the delivery of therapeutically effective amounts of a variety of drugs and other therapeutic agents. These include a number of large molecule peptides and proteins which would otherwise require injection due to chemical breakdown in the stomach e.g., antibodies growth hormone, parathyroid hormone, insulin, interferons and other like compounds. Suitable drugs and other therapeutic agents which can be delivered by embodiments of invention include various antibodies (e.g., anti-PCSK9 antibodies, TNF inhibiting class of antibodies, chemotherapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents, immune suppression agents and anti-parasitic agents such as various anti-malarial agents. The dosage of the particular drug can be titrated for the patient's weight, age, condition or other parameter.

In various method embodiments of the invention, embodiments of the drug swallowable drug delivery device can be used to deliver a plurality of drugs for the treatment of multiple conditions or for the treatment of a particular condition (e.g., a mixture of protease inhibitors for treatment HIV AIDS). In use, such embodiments allow a patient to forgo the necessity of having to take multiple medications for a particular condition or conditions. Also, such embodiments provide a means for ensuring that a regimen of two or more drugs is delivered and absorbed into the small intestine and thus, the blood stream at about the same time. Due to differences in chemical makeup, molecular weight, etc., drugs can be absorbed through the intestinal wall at different rates, resulting in different pharmacokinetic distribution curves. Embodiments of the invention address this issue by injecting the desired drug mixtures at about the same time. This in turn improves (e.g. by substantially synchronizing e.g., within 5% in time) the pharmacokinetic parameters for the mixture of the selected drugs (e.g., by achieving similar $t_{1/2}$'s for different drugs) and thus, the efficacy of the selected mixture of drugs.

In another aspect, various embodiment of the invention provide pharmaceutical compositions comprising solid shaped masses comprising a drug such as an antibody or other immunglobulin having a biological activity (e.g. binding affinity for an antigen) in the body of a mammal wherein at least a portion of the biological activity of the antibody is maintained after formation of the shape mass from a precursor material such as powder. The biological activity may be correlated to the structural integrity of the antibody or other drug post formation (e.g. by correlating bioactivity assays to chemical assays), such that on a compositional level, a selected percentage of the antibody (e.g., on a weight basis) is maintained post formation relative to that in the precursor material. Typically, the shape will be formed by a compression process (e.g. compression molding), though other processes are also contemplated such as non compressive molding. The drug may correspond to a peptide, antibody, immunglobulin or other protein wherein the biological activity of the drug in the shaped mass is at least 70% to that prior to compression and more preferably, at least 90% to that prior to compression and still more preferably at least 95%. These numbers may also correspond to a weight percentage of the drug remaining in the shaped mass relative to that in the precursor material (e.g., by correlating biological activity assays to chemical assays for weight composition as described above). In these and related embodiments, the shaped mass can have a density in a range of about 1.00 and 1.15 mg/mm3 and in more preferred embodiments, 1.02 and 1.06 mg/mm3. The shape will typically comprise a pellet shape but may also have a tablet, conical, cylindrical, cube, sphere or other like shape. Typically the pellet or other form of the shaped mass will then by inserted into an embodiment of the tissue penetrating member described herein.

Embodiments of the invention also provide methods for forming solid shaped masses comprising antibodies, immuglobulins, or other proteins where the shaped masses are formed by the shaping of a precursor material and where at least a portion of the biological activity (e.g antigen binding affinity, specifity, etc) of the peptide, antibody or other protein in the shaped mass is preserved after formation. In many embodiments, the shaping is done by compression of the precursor material where the compressive forces are selected to minimize degradation of the biological activity of the protein or polypeptide. Other shaping methods are also contemplated. Typically, the precursor material will comprise a powder mixture comprising the drug and one or more excipients. The precursor material may also comprise a liquid, slurry or paste. The excipients may include one more of a lubricant, a binder, bulking agent, etc. The shaped mass may be in the form of a tablet, micro-tablet, pill or slug shape. According to one or more embodiments, the shaped masses produced using embodiments of the formation process can have another property such as density or particle grain size (of the powder used to formulate the shaped mass) which is correlated to minimum level of bioactivity of the protein or peptide. Also, that correlated property may be may consistently maintained within a selected range within a given lot of shaped masses as well from lot to lot. Embodiments of the solid masses described herein can be configured to be used in combination with any suitable drug delivery system to be administered via any appropriate route of administration for the condition to be treated. Such routes of administration can include without limitation, oral, sublingual parenteral, intravenous, intramuscular, intra-ventricular, intra-cardiac, intracranial. For example, according to one embodiments, antibody-containing micro-tablets (e.g, a microtablet containing an anti-PCSK9 antibody) can be taken orally and delivered into the small intestine where the antibody is delivered into the wall of the small intestine and/or peritoneal wall where the tablet(s) dissolves to release the antibody into the blood stream where it binds to the selected target molecule (e.g an PCSK9) to treat one or more conditions (e.g various autoimmune conditions such as rheumatoid arthritis, multiple sclerosis, psoriatis, etc). In another embodiment insulin, containing micro tablets can be injected or otherwise placed subcutaneously (e.g. intramuscularly) where they dissolve to release antibody into the bloodstream.

Further details of these and other embodiments and aspects of the invention are described more fully below, with reference to the attached drawing figures.

BRIEF DESCRIPTION OF THE DRAWINGS

FIGS. 8a-8c are side view illustrating positioning of the drug delivery device in the small intestine and deployment of the tissue penetrating members to deliver drug; FIG. 8a shows the device in the small intestine prior to deployment of the tissue penetrating members with the release element in tact; FIG. 8b shows the device in the small intestine with the release element degraded and the tissue penetrating elements deployed; and FIG. 8c shows the device in the small intestine with the tissue penetrating elements retracted and the drug delivered.

FIG. 12a shows the capsule in an unassembled state and FIG. 12b in an assembled state FIG. 13a shows an embodiment of the assembly for a single dome configuration of the deployment balloon; and FIG. 13b shows an embodiment of the assembly for dual dome configuration of the deployment balloon; and.

FIG. 14a shows the balloon in a non-inflated state with the separation valve closed; FIG. 14b shows the balloon with valve open and mixing of the chemical reactants; and FIG. 14c shows the balloon in an inflated state.

FIG. 15d, pertains to the final folding step unique to dual dome configurations; FIG. 15e, pertains to a folding step unique to single dome configurations; and FIGS. 15f and 15g are orthogonal views pertaining to the final folding step unique to single dome configurations.

FIG. 18e shows the tissue penetrating member and shaped drug section prior to assembly; and FIG. 18f after assembly.

FIGS. 20a-20i provide assorted views illustrating a method of operation of an embodiment of the swallowable device to deliver medication to the intestinal wall.

FIG. 21 is a table illustrating various information for PCSK9s, including PCSK9s configured to be bound and/or neutralized by one or more antibodies provided by embodiments of the invention.

FIGS. 22a and 22b are simulated plasma concentration profiles for Alirocumab delivered daily by embodiments of the swallowable capsule (FIG. 22b) and monthly by injection using conventional means (FIG. 22a).

DETAILED DESCRIPTION OF THE INVENTION

Figure 1A:
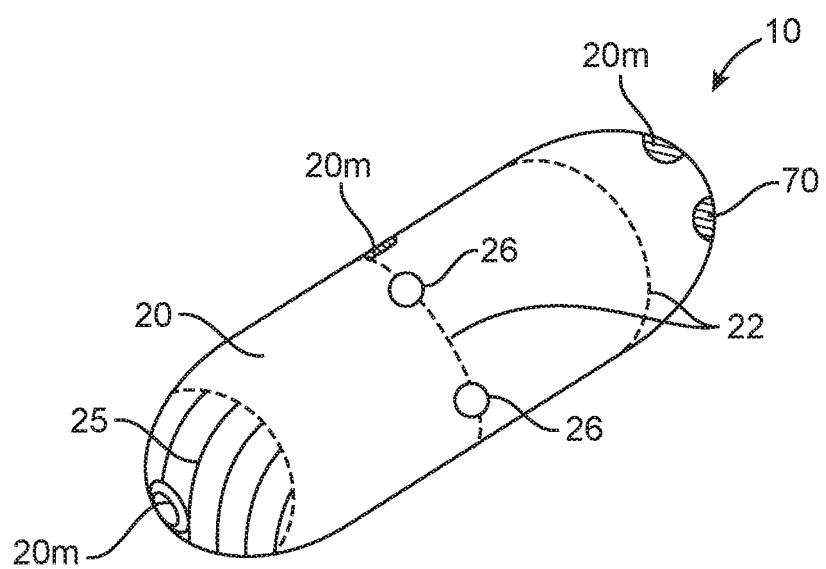
FIG. 1a is a lateral viewing showing an embodiment of a swallowable drug delivery device.

Embodiments of the invention provide devices, systems and methods for delivering medications in to various locations in the body as well as therapeutic compositions comprising the medication. As used herein, the term "medication" refers to a medicinal preparation in any form which can include one more drugs or other therapeutic agent as well as one or more pharmaceutical excipients. Many embodiments provide a swallowable device for delivering medication within the GI tract. Particular embodiments provide a swallowable device such as a capsule for delivering medications into the wall of the small intestine and/or peritoneal wall or other GI organ. As used herein, "GI tract" refers to the esophagus, stomach, small intestine, large intestine and anus, while "Intestinal tract" refers to the small and large intestine. Particular embodiments also provide therapeutics preparations for delivery into the wall of the GI tract comprising a therapeutically effective dose of at least one PCSK9 neutralizing protein (PN protein or PNP also known as a PCSK9 binding protein or PB-protein) such as an antibody which binds to PCSK9 molecules (herein anti-PCSK9 antibodies or AP-antibodies) or its receptors along with their respective analogues and derivatives. Various embodiments of the invention can be configured and arranged for delivery of medication into the intestinal tract as well as the entire GI tract. Also, as used herein, the term "about" means within 10% of a given stated numerical value for a parameter, variable, dimension, and the like (e.g., a pharmacokinetic parameter such as $t_{1/2}$, $t_{max}$, $c_{max}$, etc.).

Referring now to FIGS. 1-11, an embodiment of a device 10 for the delivery of medication 100 to a delivery site DS in the intestinal tract such as the of the small intestine and/or peritoneal wall, comprises a capsule 20 including at least one guide tube 30, one or more tissue penetrating members 40 positioned or otherwise advanceable in the at least one guide tube, a delivery member 50, an actuating mechanism 60 and release element 70. Medication 100, also described herein as preparation 100, typically comprises at least one drug or therapeutic agent 101 and may include one or more pharmaceutical excipients known in the art. Collectively, one or more of delivery member 50 and mechanism 60 may comprise a means for delivery of medication 100 into a wall of the intestinal tract. Other delivery means contemplated herein include one or more expandable balloons (e.g., delivery balloon 172) or other expandable device/member described herein.

Figure 1B:
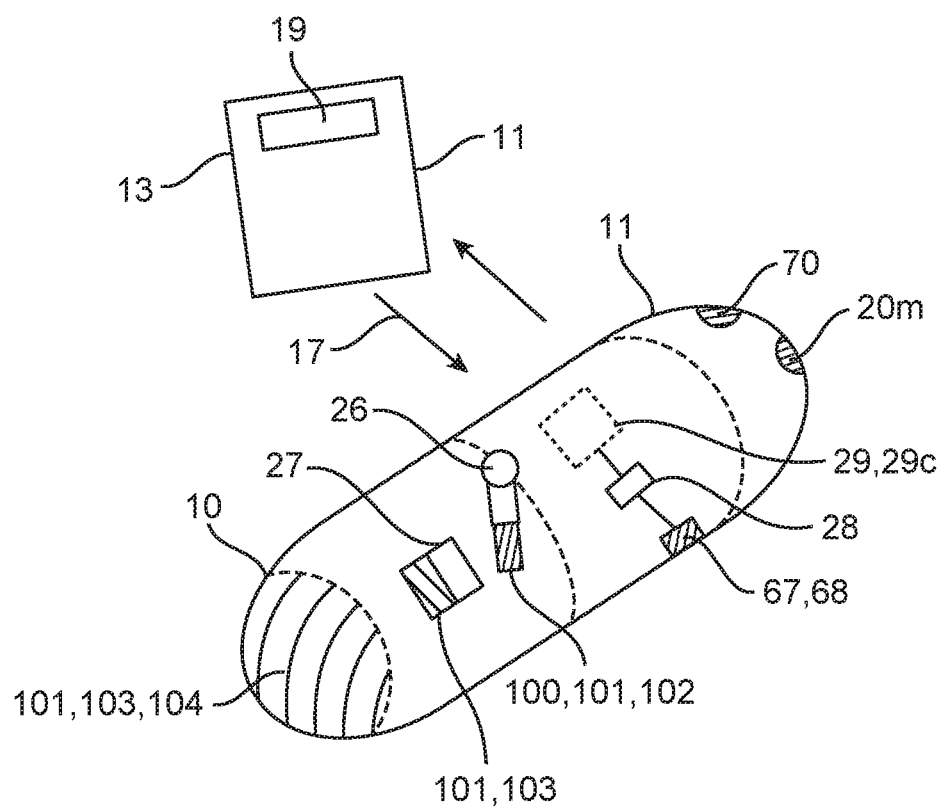
FIG. 1b is a lateral viewing showing an embodiment of a system including a swallowable drug delivery device.

Device 10 can be configured for the delivery of liquid, semi-liquid or solid forms of medication 100 or all three. Solid forms of medication/preparation 100 can include both powder and pellet. Semi liquid forms can include a slurry or paste. Whatever the form, preparation 100 desirably has a shape and material consistency allowing the medication to be advanced out of the device, into the intestinal wall (or other luminal wall in the GI tract) and then degrade in the intestinal wall to release the drug or other therapeutic agent 101 which in various embodiments may correspond to one or more Anti-PCSK9 antibodies (or other PCSK9 neutralizing proteins) described herein. The material consistency can include one or more of the hardness, porosity and solubility of the preparation (in body fluids). The material consistency can be achieved by one or more of the following: i) the compaction force used to make the preparation; ii) the use of one or more pharmaceutical disintegrants known in the art; iii) use of other pharmaceutical excipients; iv) the particle size and distribution of the preparation (e.g., micronized particles); and v) use of micronizing and other particle formation methods known in the art. Suitable shapes for preparation 100 can include cylindrical, cubical, rectangular, conical, spherical, hemispherical and combinations thereof. Also, the shape can be selected so as to define a particular surface area and volume of preparation 100 and thus, the ratio between the two. The ratio of surface area to volume can in turn, be used to achieve a selected rate of degradation within the intestinal or other lumen wall within the GI tract. Larger ratios (e.g., larger amounts of surface area per unit volume) can be used to achieve faster rates of degradation and vice versa. In particular embodiments, the surface area to volume ratio can be in the range of about 1:1 to 100:1, with specific embodiments of 2:1, 5:1, 20:1, 25:1, 50:1 and 75:1 (about being within 5%). Preparation/medication 100 will typically be pre-packed within a lumen 44 of tissue penetrating members 40, but can also be contained at another location within an interior 24 of capsule 20, or in the case of a liquid or semi-liquid, within an enclosed reservoir 27. The medication can be pre-shaped to fit into the lumen or packed for example, in a powder form. Typically, the device 10 will be configured to deliver a single drug 101 as part of medication 100. However in some embodiments, the device 10 can be configured for delivery of multiple drugs 101 including a first second, or a third drug which can be compounded into a single or multiple medications 100. For embodiments having multiple medications/drugs, the medications can be contained in separate tissue penetrating members 40 or within separate compartments or reservoirs 27 within capsule 20. In another embodiment, a first dose 102 of medication 100 containing a first drug 101 can be packed into the penetrating member(s) 40 and a second dose 103 of medication 100 (containing the same or a different drug 101) can be coated onto the surface 25 of capsule as is shown in the embodiment of FIG. 1b. The drugs 101 in the two doses of medication 102 and 103 can be the same or different. In this way, a bimodal pharmacokinetic release of the same or different drugs can be achieved. The second dose 103 of medication 100 can have an enteric coating 104 to ensure that it is released in the small intestine and achieve a time release of the medication 100 as well. Enteric coating 104 can include one or more enteric coatings described herein or known in the art.

Figure 1C:
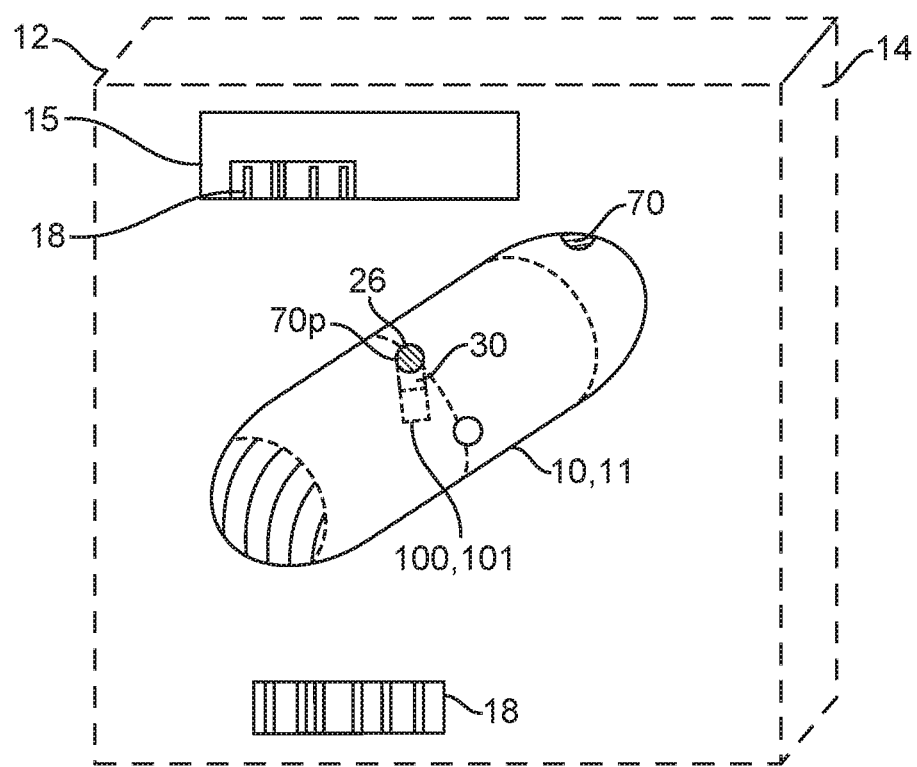
FIG. 1c is a lateral viewing showing an embodiment of a kit including a swallowable drug delivery device and a set of instructions for use.
Figure 1D:
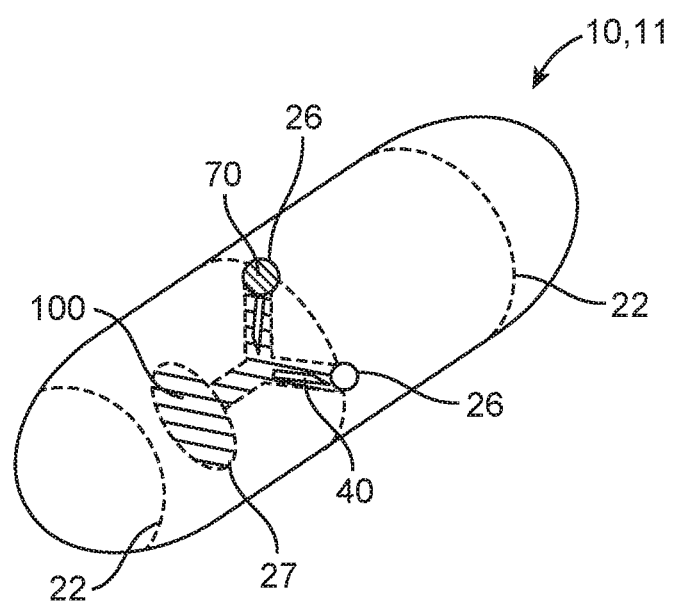
FIG. 1d is a lateral viewing showing an embodiment of a swallowable drug delivery device including a drug reservoir.

A system 11 for delivery of medication 100 into the wall of the small intestine and/or peritoneal wall or other location within the GI tract, may comprise device 10, containing one or more medications 100 for the treatment of a selected condition or conditions. In some embodiments, the system may include a hand held device 13, described herein for communicating with device 10 as is shown in the embodiment of FIG. 1b. System 11 may also be configured as a kit 14 including system 11 and a set of instructions for use 15 which are packaged in packaging 12 as is shown in the embodiment of FIG. 1c. The instructions can indicate to the patient when to take the device 10 relative to one or more events such as the ingestion of a meal or a physiological measurement such as blood glucose, cholesterol, etc. In such embodiments, kit 14 can include multiple devices 10 containing a regimen of medications 100 for a selected period of administration, e.g., a day, week, or multiple weeks depending upon the condition to be treated.

Capsule 20 is sized to be swallowed and pass through the intestinal tract. The size can also be adjusted depending upon the amount of drug to be delivered as well as the patient's weight and adult vs. pediatric applications. Capsule 20 includes an interior volume 24 and an outer surface 25 having one or more apertures 26 sized for guide tubes 30. In addition to the other components of device 10, (e.g., the actuation mechanism etc.) the interior volume can include one or more compartments or reservoirs 27. One or more portions of capsule 20 can be fabricated from various biocompatible polymers known in the art, including various biodegradable polymers which in a preferred embodiment can comprise PGLA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof. As is described in further detail herein, in various embodiments, capsule 20 can include seams 22 of bio-degradable material so as to controllably degrade into smaller pieces 23 which are more easily passed through the intestinal tract. Additionally, in various embodiments, the capsule can include various radio-opaque or echogenic materials for location of the device using fluoroscopy, ultrasound or other medical imaging modality. In specific embodiments, all or a portion of the capsule can include radio-opaque/echogenic markers 20m as is shown in the embodiment of FIGS. 1a and 1b. In use, such materials not only allow for the location of device 10 in the GI tract, but also allow for the determination of transit times of the device through the GI tract.

In preferred embodiments, tissue penetrating members 40 are positioned within guide tubes 30 which serve to guide and support the advancement of members 40 into tissue such as the of the small intestine and/or peritoneal wall or other portion of the GI tract. The tissue penetrating members 40 will typically comprise a hollow needle or other like structure and will have a lumen 44 and a tissue penetrating end 45 for penetrating a selectable depth into the intestinal wall IW. Member 40 may also include a pin 41 for engagement with a motion converter 90 described herein. The depth of penetration can be controlled by the length of member 40, the configuration of motion converter 90 described herein as well as the placement of a stop or flange 40s on member 40 which can, in an embodiment, correspond to pin 41 described herein. Medication 100 will typically be delivered into tissue through lumen 44. In many embodiments, lumen 44 is pre-packed with the desired medication 100 which is advanced out of the lumen using delivery member 50 or other advancement means (e.g. by means of force applied to a collapsible embodiment of member 40). As an alternative, medication 100 can be advanced into lumen 44 from another location/compartment in capsule 20. In some embodiments, all or a portion of the tissue penetrating member 40 can be fabricated from medication 100 itself. In these and related embodiments, the medication can have a needle or dart-like structure (with or without barbs) or other elongated structure with a pointed end configured to penetrate and be retained in the intestinal wall (e.g., the wall of the small intestine and/or peritoneal wall) after insertion. The dart can be sized and shaped depending upon the medication, dose and desired depth of penetration into the intestinal wall. Medication 100 can be formed into darts, pellets or other shapes using various compression molding methods known in the pharmaceutical arts.

Figure 7A:
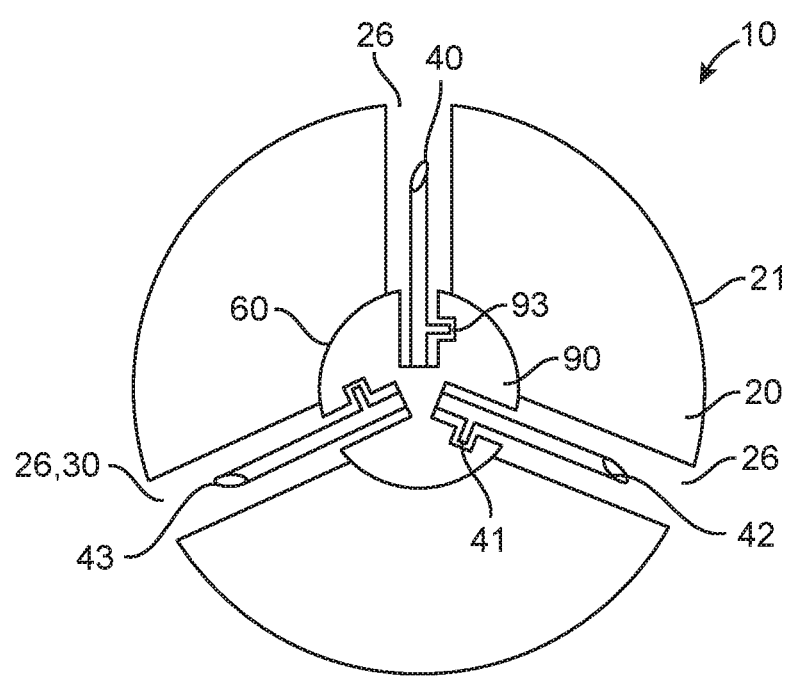
FIG. 7a is a cross sectional view illustrating an embodiment of the swallowable drug delivery device having multiple tissue penetrating members and an actuating mechanism for advancing the tissue penetrating members.
Figure 7B:
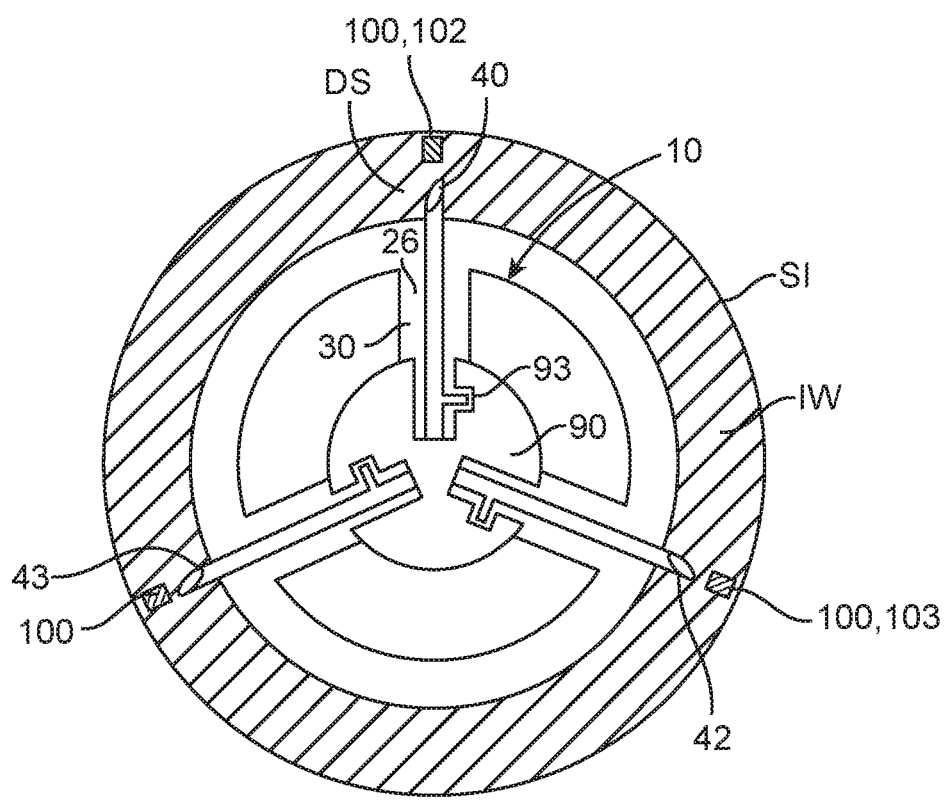
FIG. 7b is a cross sectional view illustrating deployment of the tissue penetrating members of the embodiment of FIG. 7a to deliver medication to a delivery site and anchor the device in the intestinal wall during delivery.
Figure 8C:
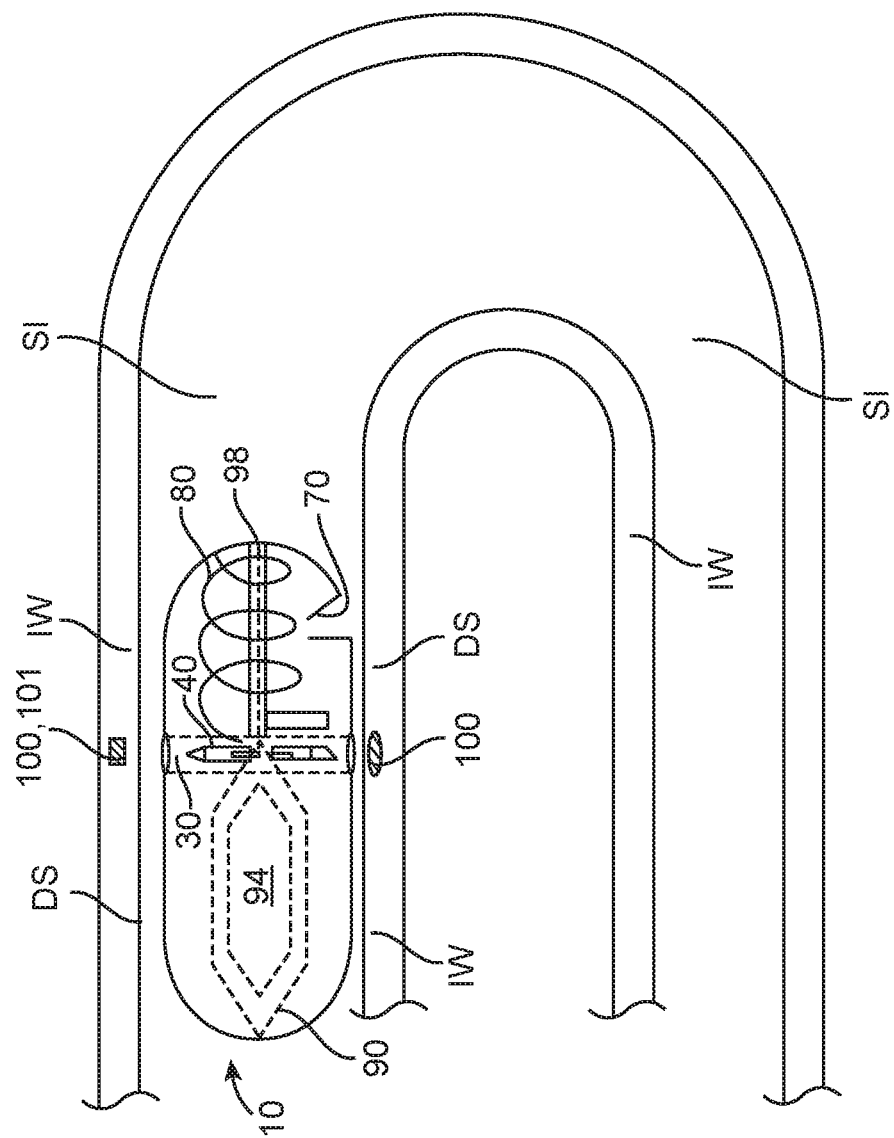

In various embodiments, device 10 can include a second 42 and a third 43 tissue penetrating member 40 as is shown in the embodiments of FIGS. 7a and 7b, with additional numbers contemplated. Each tissue penetrating member 40 can be used to deliver the same or a different medication 100. In preferred embodiments, the tissue penetrating members 40 can be substantially symmetrically distributed around the perimeter 21 of capsule 20 so as to anchor the capsule onto the intestinal wall IW during delivery of medications 100. Anchoring capsule 20 in such a way reduces the likelihood that the capsule will be displaced or moved by peristaltic contractions occurring during delivery of the medication. In specific embodiments, the amount of anchoring force can be adjusted to the typical forces applied during peristaltic contraction of the small intestine. Anchoring can be further facilitated by configured some or all of tissue penetrating members 40 to have a curved or arcuate shape.

Delivery member 50 is configured to advance medication 100 through the tissue penetrating member lumen 44 and into the intestinal wall IW. Accordingly, at least a portion of the delivery member 50 is advanceable within the tissue penetrating member lumen 44 and thus member 50 has a size and shape (e.g., a piston like shape) configured to fit within the delivery member lumen 44.

In some embodiments, the distal end 50d of the delivery member (the end which is advanced into tissue) can have a plunger element 51 which advances the medication within the tissue penetrating member lumen 44 and also forms a seal with the lumen. Plunger element 51 can be integral or attached to delivery member 50. Preferably, delivery member 50 is configured to travel a fixed distance within the needle lumen 44 so as to deliver a fixed or metered dose of drug into the intestinal wall IW. This can be achieved by one or more of the selection of the diameter of the delivery member (e.g., the diameter can be distally tapered), the diameter of the tissue penetrating member (which can be narrowed at its distal end), use of a stop, and/or the actuating mechanism. However in some embodiments, the stroke or travel distance of member 50 can be adjusted in situ responsive to various factors such as one or more sensed conditions in the GI tract. In situ adjustment can be achieved through use of logic resource 29 (including controller 29c) coupled to an electro-mechanical embodiment of actuating mechanism 60. This allows for a variable dose of medication and/or variation of the distance the medication is injected into the intestinal wall.

Actuating mechanism 60 can be coupled to at least one of the tissue penetrating member 40 or delivery member 50. The actuating mechanism is configured to advance tissue penetrating member 40 a selectable distance into the intestinal wall IW as well as advance the delivery member to deliver medication 100 and then withdraw the tissue penetrating member from the intestinal wall. In various embodiments, actuating mechanism 60 can comprise a spring loaded mechanism which is configured to be released by release element 70. Suitable springs 80 can include both coil (including conical shaped springs) and leaf springs with other spring structures also contemplated. In particular embodiments, spring 80 can be substantially cone-shaped to reduce the length of the spring in the compressed state even to the point where the compressed length of the spring is about the thickness of several coils (e.g., two or three) or only one coil.

Figure 2:
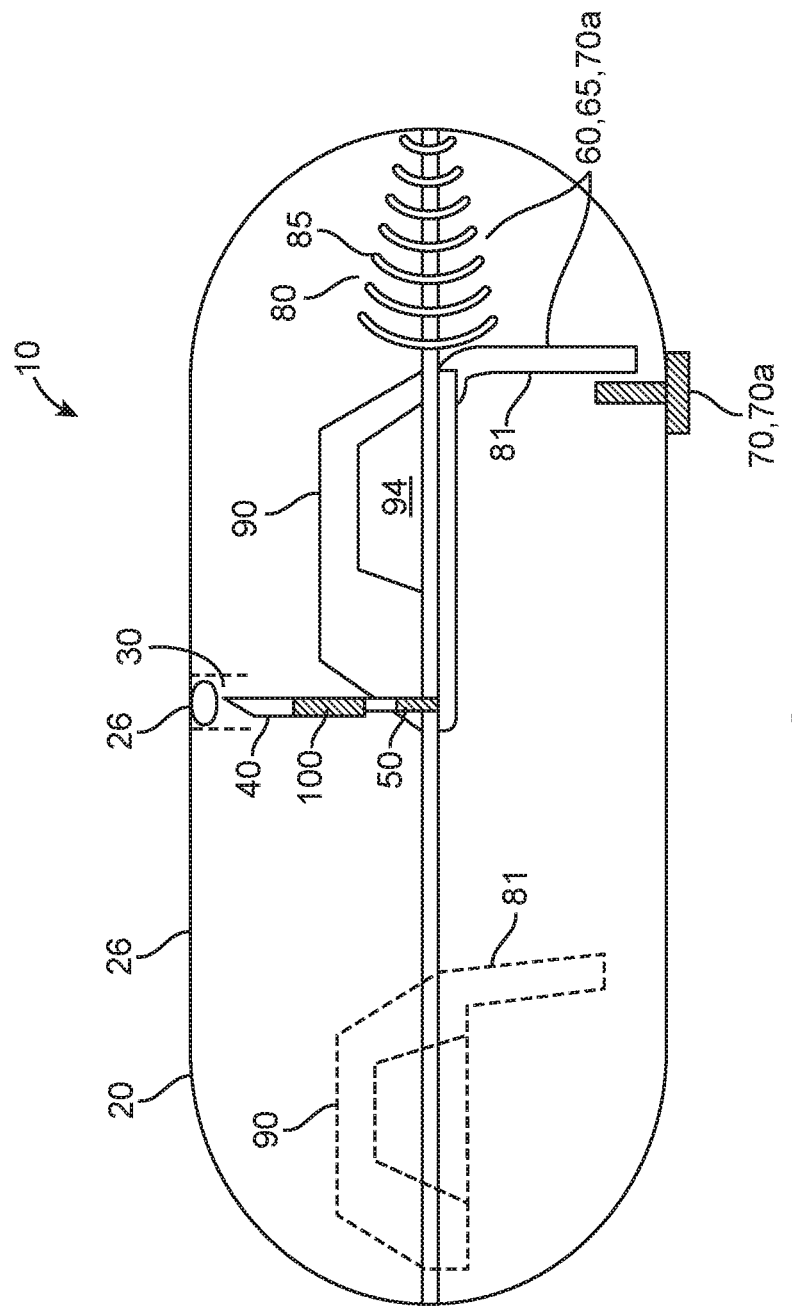
FIG. 2 is a lateral view illustrating an embodiment of the swallowable drug delivery device having a spring loaded actuation mechanism for advancing tissue penetrating members into tissue.
Figure 3:
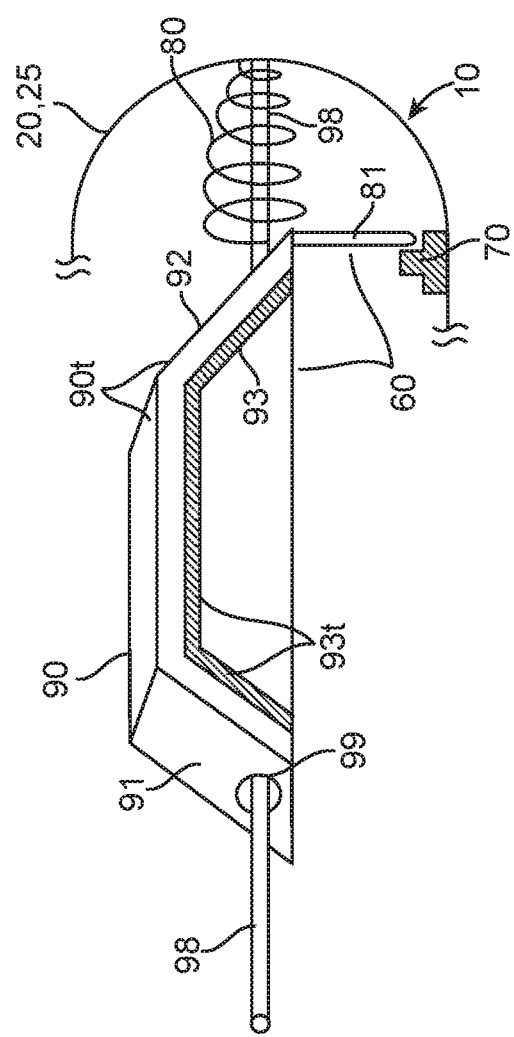
FIG. 3 is a lateral view illustrating an embodiment of the swallowable drug delivery device having a spring loaded actuation mechanism having a first motion converter.
Figure 4:
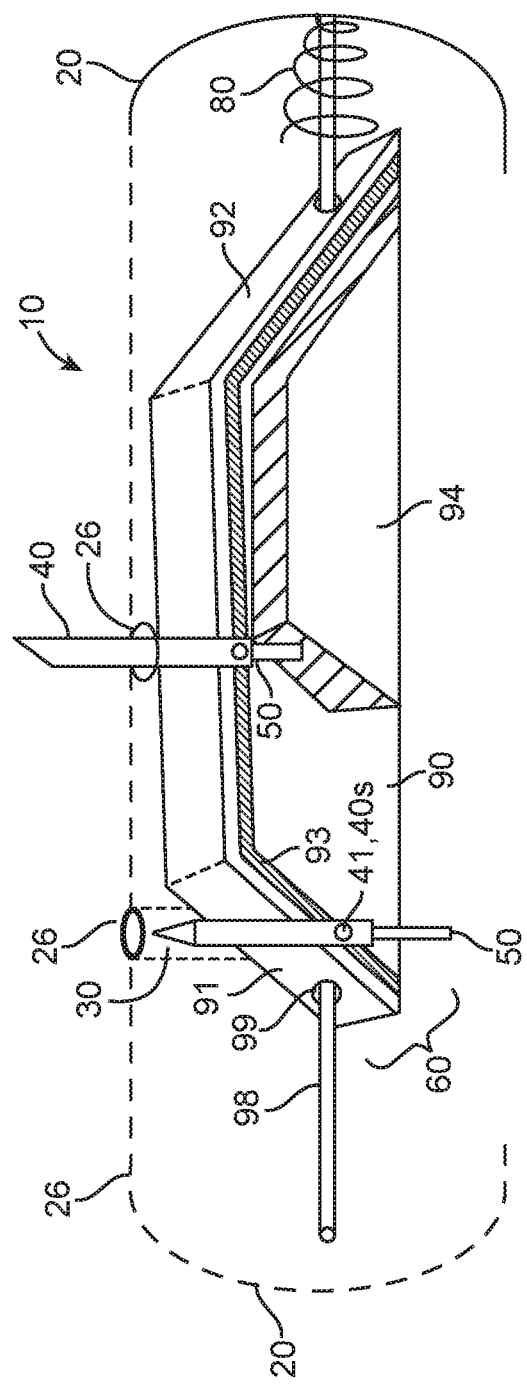
FIG. 4 is a lateral view illustrating an embodiment of the swallowable drug delivery device having a spring loaded actuation mechanism having first and a second motion converter.
Figure 5:
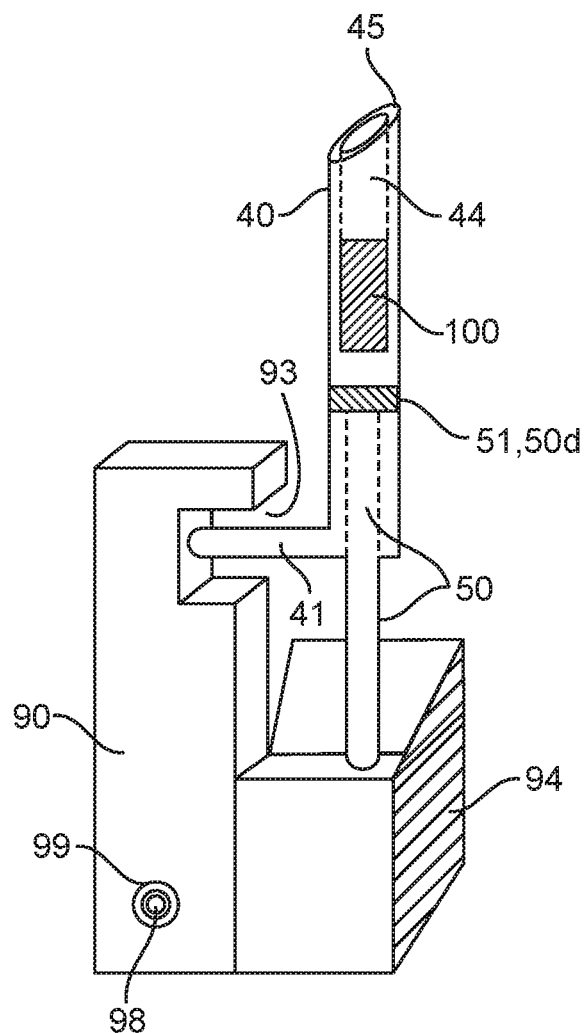
FIG. 5 is a perspective view illustrating engagement of the first and second motion converters with the tissue penetrating member and delivery members.
Figure 6:
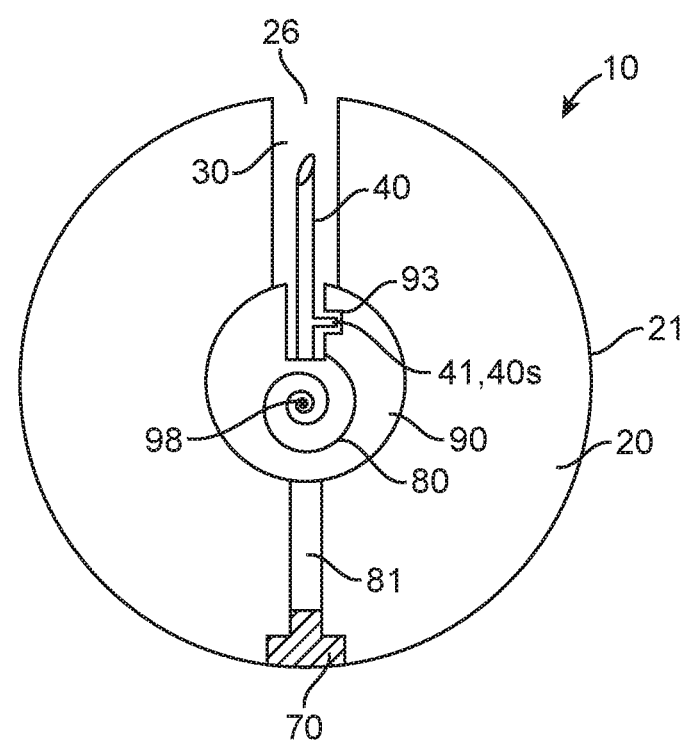
FIG. 6 is a cross sectional view illustrating an embodiment of the swallowable drug delivery device having a single tissue penetrating member and an actuating mechanism for advancing the tissue penetrating member.

In particular embodiments actuating mechanism 60 can comprise a spring 80, a first motion converter 90, and a second motion converter 94 and a track member 98 as is shown in the embodiments of FIGS. 2, 4 and 8a-8c. The release element 70 is coupled to spring 80 to retain the spring in a compressed state such that degradation of the release element releases the spring. Spring 80 may be coupled to release element 70 by a latch or other connecting element 81. First motion converter 90 is configured to convert motion of spring 80 to advance and withdraw the tissue penetrating member 40 in and out of the intestinal wall or other tissue. The second motion converter 94 is configured to convert motion of the spring 80 to advance the delivery member 50 into the tissue penetrating member lumen 44. Motion converters 90 and 94 are pushed by the spring and ride along a rod or other track member 98 which fits into a track member lumen 99 of converter 90. The track member 98 serves to guide the path of the converters 90. Converters 90 and 94 engage the tissue penetrating member 40 and/or delivery member 50 (directly or indirectly) to produce the desired motion. They have a shape and other characteristics configured to convert motion of the spring 80 along its longitudinal axis into orthogonal motion of the tissue penetrating member 40 and/or delivery member 50 though conversion in other directions is also contemplated. The motion converters can have a wedge, trapezoidal or curved shape with other shapes also contemplated. In particular embodiments, the first motion converter 90 can have a trapezoidal shape 90t and include a slot 93 which engages a pin 41 on the tissue penetrating member that rides in the slot as is shown in the embodiments of FIGS. 2, 3 and 4. Slot 93 can also have a trapezoidal shape 93t that mirrors or otherwise corresponds to the overall shape of converter 90. Slot 93 serves to push the tissue penetrating member 40 during the upslope portion 91 of the trapezoid and then pull it back during the down slope portion 92. In one variation, one or both of the motion converters 90 and 94 can comprise a cam or cam like device (not shown). The cam can be turned by spring 80 so as to engage the tissue penetrating and/or delivery members 40 and 50. One or more components of mechanism 60 (as well as other components of device 10) including motion converters 90 and 94 can be fabricated using various MEMS-based methods known in the art so as to allow for selected amounts of miniaturization to fit within capsule 10. Also as is described herein, they can be formed from various biodegradable materials known in the art.

In other variations, the actuating mechanism 60 can also comprise an electro-mechanical device/mechanism such as a solenoid or a piezoelectric device. In one embodiment, a piezoelectric device used in mechanism 60 can comprise a shaped piezoelectric element which has a non-deployed and deployed state. This element can be configured to go into the deployed state upon the application of a voltage and then return to the non-deployed state upon the removal of the voltage or other change in the voltage. This and related embodiments allow for a reciprocating motion of the actuating mechanism 60 so as to both advance the tissue penetrating member and then withdraw it. The voltage for the piezoelectric element can be obtained generated using a battery or a piezoelectric based energy converter which generates voltage by mechanical deformation such as that which occurs from compression of the capsule 20 by a peristaltic contraction of the small intestine around the capsule. Further description of piezoelectric based energy converters is found in U.S. patent application Ser. No. 12/556,524 which is fully incorporated by reference herein for all purposes. In one embodiment, deployment of tissue penetrating members 40 can in fact be triggered from a peristaltic contraction of the small intestine which provides the mechanical energy for generating voltage for the piezoelectric element.

Release element 70 will typically be coupled to the actuating mechanism 60 and/or a spring coupled to the actuating mechanism; however, other configurations are also contemplated. In preferred embodiments, release element 70 is coupled to a spring 80 positioned within capsule 20 so as to retain the spring in a compressed state 85 as shown in the embodiment of FIG. 2. Degradation of the release element 70 releases spring 80 to actuate actuation mechanism 60. Accordingly, release element 70 can thus function as an actuator 70a (actuator 70 may also include spring 80 and other elements of mechanism 60). As is explained further below, release element 70/actuator 70a has a first configuration where the therapeutic agent preparation 100 is contained within capsule 20 and a second configuration where the therapeutic agent preparation is advanced from the capsule into the wall of the small intestine and/or peritoneal wall or other luminal wall in the intestinal tract.

In many embodiments, release element 70 comprises a material configured to degrade upon exposure to chemical conditions in the small or large intestine such as pH. Typically, release element 70 is configured to degrade upon exposure to a selected pH in the small intestine, e.g., 7.0, 7.1, 7.2, 7.3, 7.4, 7.5, 7.6 8.0 or greater. The release element can also be configured to degrade within a particular range of pH such as, e.g., 7.0 to 7.5. In particular embodiments, the pH at which release element 70 degrades (defined herein as the degradation pH) can be selected for the particular drug to be delivered so as to release the drug at a location in small intestine which corresponds to the selected pH. Further, for embodiments of device 10 having multiple medications 100, the device can include a first release element 70 (coupled to an actuating mechanism for delivering a first drug) configured to degrade at first pH and a second release element 70 (coupled to an actuating mechanism for delivering a second drug) configured to degrade at a second pH (with additional numbers of release elements contemplated for varying number of drugs).

Release element 70 can also be configured to degrade in response to other conditions in the small intestine (or other GI location). In particular embodiments, the release element 70 can be configured to degrade in response to particular chemical conditions in the fluids in the small intestine such as those which occur after ingestion of a meal (e.g., a meal containing fats, starches or proteins). In this way, the release of medication 100 can be substantially synchronized or otherwise timed with the digestion of a meal.

Various approaches are contemplated for biodegradation of release element 70. In particular embodiments, biodegradation of release element 70 from one or more conditions in the small intestine (or other location in the GI tract) can be achieved by one or more of the following approaches: i) selection of the materials for the release element, ii) the amount of cross linking of those materials; and iii) the thickness and other dimensions of the release element. Lesser amounts of cross linking and or thinner dimensions can increase the rate of degradation and vice versa. Suitable materials for the release element can comprise biodegradable materials such as various enteric materials which are configured to degrade upon exposure to the higher pH in the intestines. Suitable enteric materials include, but are not limited to, the following: cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters as well as other enteric materials known in the art. The selected enteric materials can be copolymerized or otherwise combined with one or more other polymers to obtain a number of other particular material properties in addition to biodegradation. Such properties can include without limitation stiffness, strength, flexibility and hardness.

In alternative embodiments, the release element 70 can comprise a film or plug 70p that fits over or otherwise blocks guide tubes 30 and retains the tissue penetrating member 40 inside the guide tube. In these and related embodiments, tissue penetrating member 40 is coupled to a spring loaded actuating mechanism such that when the release element is degraded sufficiently, it releases the tissue penetrating member which then springs out of the guide tube to penetrate into the intestinal wall. In still other embodiments, release element 70 can be shaped to function as a latch which holds the tissue penetrating member 40 in place. In these and related embodiments, the release element can be located on the exterior or the interior of capsule 20. In the latter case, capsule 20 and/or guide tubes 30 can be configured to allow for the ingress of intestinal fluids into the capsule interior to allow for the degradation of the release element.

In some embodiments, actuating mechanism 60 can be actuated by means of a sensor 67, such as a pH sensor 68 or other chemical sensor which detects the presence of the capsule in the small intestine. Sensor 67 can then send a signal to actuating mechanism 60 or to an electronic controller 29c coupled to actuating mechanism 60 to actuate the mechanism. Embodiments of a pH sensor 68 can comprise an electrode-based sensor or it can be a mechanically-based sensor such as a polymer which shrinks or expands upon exposure to a selected pH or other chemical conditions in the small intestine. In related embodiments, an expandable/contractible sensor 67 can also comprise the actuating mechanism 60 itself by using the mechanical motion from the expansion or contraction of the sensor.

According to another embodiment for detecting that the device in the small intestine (or other location in the GI tract), sensor 67 can comprise pressure/force sensor such as strain gauge for detecting the number of peristaltic contractions that capsule 20 is being subject to within a particular location in the intestinal tract (in such embodiments capsule 20 is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments, detection of the number of peristaltic contractions can be used to not only determine if capsule 20 is in the small intestine, but the relative location within the intestine as well. In use, these and related embodiments allow for release of medication 100 at a particular location in the small intestine.

As an alternative or supplement to internally activated drug delivery (e.g., using a release element and/or sensor), in some embodiments, the user may externally activate the actuating mechanism 60 to deliver medication 100 by means of RF, magnetic or other wireless signaling means known in the art. In these and related embodiments, the user can use a handheld communication device 13 (e.g., a hand held RF device such as a cell phone) as is shown in the embodiment of FIG. 1b, to send a receive signals 17 from device 10. In such embodiments, swallowable device may include a transmitter 28 such as an RF transceiver chip or other like communication device/circuitry. Handheld device 13 may not only includes signaling means, but also means for informing the user when device 10 is in the small intestine or other location in the GI tract. The later embodiment can be implemented through the use of logic resources 29 (e.g., a processor 29) coupled to transmitter 28 to signal to detect and singe to the user when the device is in the small intestine or other location (e.g., by signaling an input from the sensor). Logic resources 29 may include a controller 29c (either in hardware or software) to control one or more aspects of the process. The same handheld device can also be configured to alert the user when actuating mechanism 60 has been activated and the selected medication 100 delivered (e.g., using processor 29 and transmitter 28). In this way, the user is provided confirmation that medication 100 has been delivered. This allows the user to take other appropriate drugs/therapeutic agents as well as make other related decisions (e.g., for diabetics to eat a meal or not and what foods should be eaten). The handheld device can also be configured to send a signal to swallowable device 10 to over-ride actuating mechanism 60 and so prevent delay or accelerate the delivery of medication 100. In use, such embodiments allow the user to intervene to prevent, delay or accelerate the delivery of medication, based upon other symptoms and/or patient actions (e.g., eating a meal, deciding to go to sleep, exercise etc). The user may also externally activate actuating mechanism 60 at a selected time period after swallowing the capsule. The time period can be correlated to a typical transit time or range of transit times for food moving through the user's GI tract to a particular location in the tract such as the small intestine.

Figure 10:
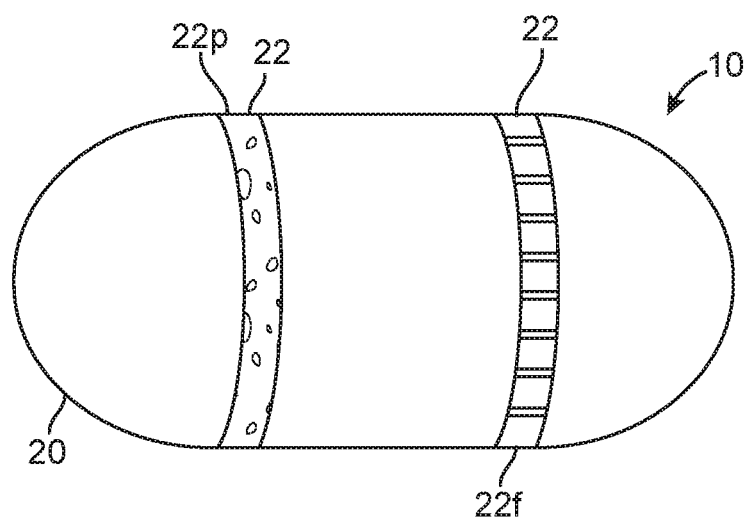
FIG. 10 shows an embodiment of a capsule having biodegradable seams including pores and/or perforations to accelerate biodegradation of the capsule.

In particular embodiments, the capsule 20 can include seams 22 of biodegradable material which controllably degrade to produce capsule pieces 23 of a selectable size and shape to facilitate passage through the GI tract as is shown in the embodiment of FIGS. 10a and 10b. Seams 22 can also include pores or other openings 22p for ingress of fluids into the seam to accelerate biodegradation as is shown in the embodiment of FIG. 10. Other means for accelerating biodegradation of seams 22 can include pre-stressing the seam and/or including perforations 22f in the seam as is also shown in the embodiment of FIG. 10. In still other embodiments, seam 22 can be constructed of materials and/or have a structure which is readily degraded by absorption of ultrasound energy, e.g. high frequency ultrasound (HIFU), allowing the capsule to be degraded into smaller pieces using externally or endoscopically (or other minimally invasive method) administered ultrasound.

Suitable materials for seams 22 can include one or more biodegradable materials described herein such as PGLA, glycolic acid etc. Seams 22 can be attached to capsule body 20 using various joining methods known in the polymer arts such as molding, hot melt junctions, etc. Additionally for embodiments of capsule 20 which are also fabricated from biodegradable materials, faster biodegradation of seam 22 can be achieved by one or more of the following: i) fabricating the seam from a faster biodegrading material, ii) pre-stressing the seam, or iii) perforating the seam. The concept of using biodegradable seams 22 to produce controlled degradation of a swallowable device in the GI tract can also be applied to other swallowable devices such as swallowable cameras (or other swallowable imaging device) to facilitate passage through the GI tract and reduce the likelihood of such a device becoming stuck in the GI tract. Accordingly, embodiments of biodegradable seam 22 can be adapted for swallowable imaging and other swallowable devices.

Figure 11:
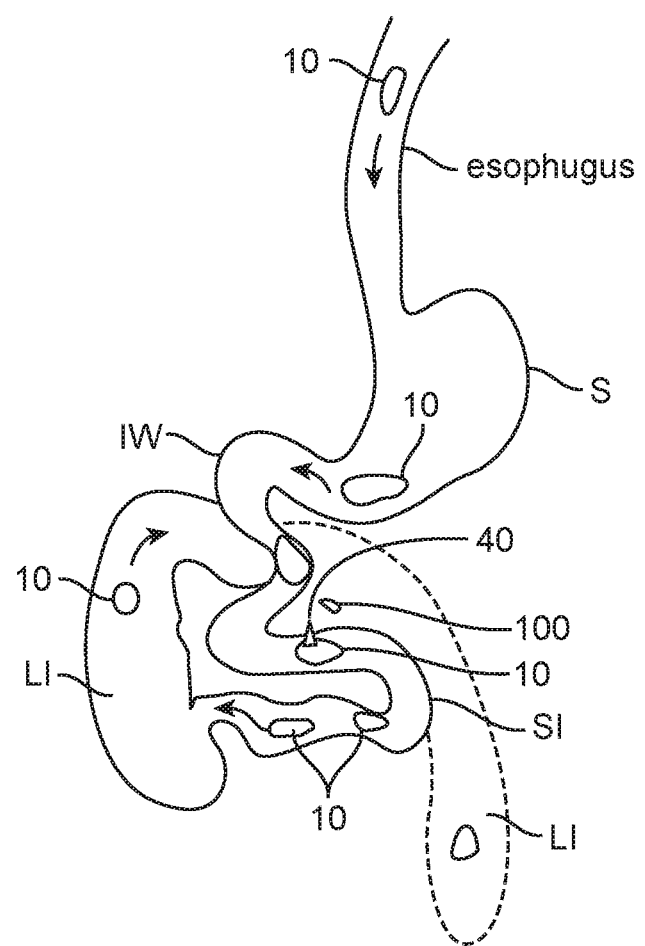
FIG. 11 is a lateral viewing illustrating use of an embodiment of a swallowable drug delivery device including transit of device in the GI tract and operation of the device to deliver drug.
Figures 12A, 12B:
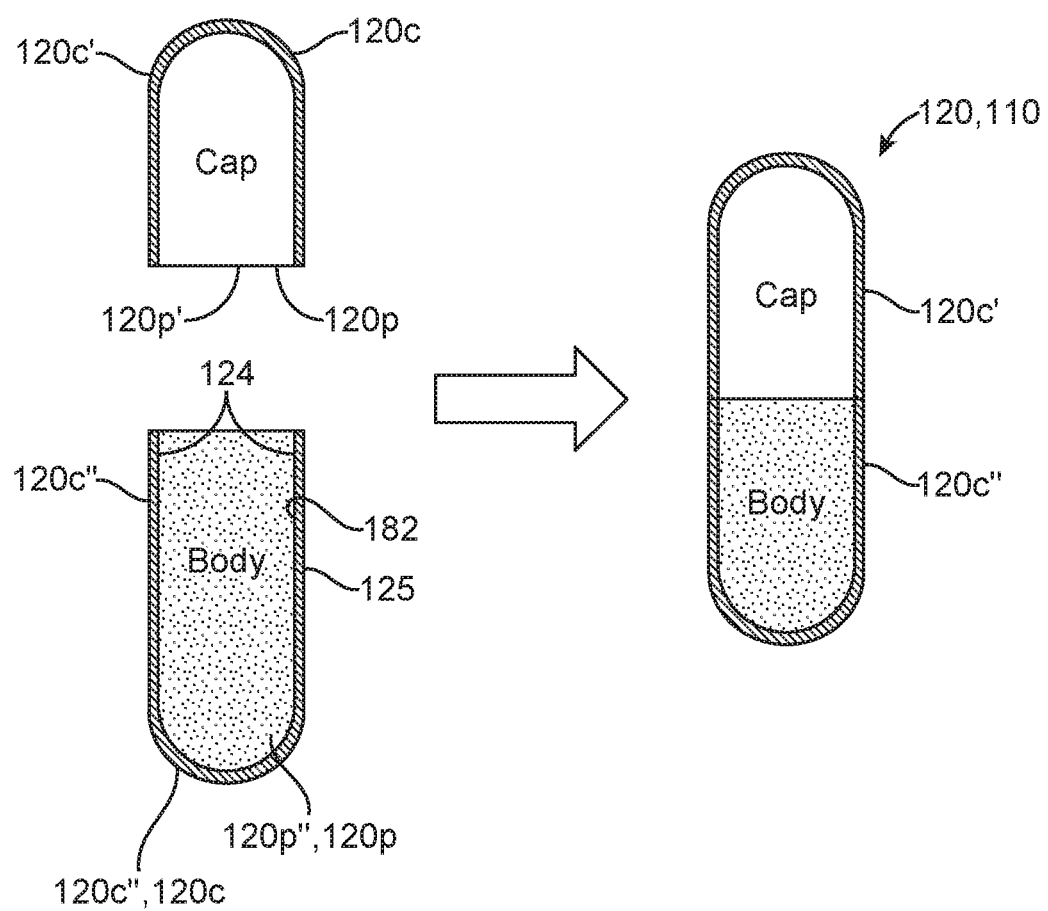
FIGS. 12a and 12b are lateral view illustrating an embodiment of a capsule for the swallowable drug delivery device including a cap and a body coated with pH sensitive biodegradable coatings.

Another aspect of the invention provides methods for the delivery of drugs and other therapeutic agents (in the form of medication 100) into the walls of the GI tract using one or more embodiments of swallowable drug delivery device 10. An exemplary embodiment of such a method will now be described. The described embodiment of drug delivery occurs in the small intestine SI. However, it should be appreciated that this is exemplary and that embodiments of the invention can be used for delivering drug in a number of locations in the GI tract including the stomach and the large intestine. For ease of discussion, the swallowable drug delivery device 10 will sometimes be referred to herein as a capsule. As described above, in various embodiments device 10 may be packaged as a kit 11 within sealed packaging 12 that includes device 10 and a set of instructions for use 15. If the patient is using a handheld device 13, the patient may instructed to enter data into device 13 either manually or via a bar code 18 (or other identifying indicia 18) located on the instructions 15 or packaging 12. If a bar code is used, the patient would scan the bar code using a bar code reader 19 on device 13. After opening packaging 12, reading the instructions 15 and entering any required data, the patient swallows an embodiment of the swallowable drug delivery device 10. Depending upon the drug, the patient may take the device 10 in conjunction with a meal (before, during or after) or a physiological measurement. Capsule 20 is sized to pass through the GI tract and travels through the patient's stomach S and into the small intestine SI through peristaltic action as is shown in the embodiment of FIG. 11. Once in the small intestine, the release element 70 is degraded by the basic pH in the small intestine (or other chemical or physical condition unique to the small intestine) so as to actuate the actuating mechanism 60 and deliver medication 100 into the wall of the small intestine SI according to one or more embodiments of the invention. For embodiments including a hollow needle or other hollow tissue penetrating member 40, medication delivery is effectuated by using the actuating mechanism 60 to advance the needle 40 a selected distance into the mucosa of the intestinal wall IW, and then the medication is injected through the needle lumen 40 by advancement of the delivery member 50. The delivery member 50 is withdrawn and the needle 40 is then withdrawn back within the body of the capsule (e.g. by recoil of the spring) detaching from the intestinal wall. For embodiments of device 10 having multiple needles, a second or third needle 42, 43 can also be used to deliver additional doses of the same drug or separate drugs 101. Needle advancement can be done substantially simultaneously or in sequence. In preferred embodiments that use multiple needles, needle advancement can be done substantially simultaneously so as to anchor device 10 in the small intestine during drug delivery.

Figure 9A:
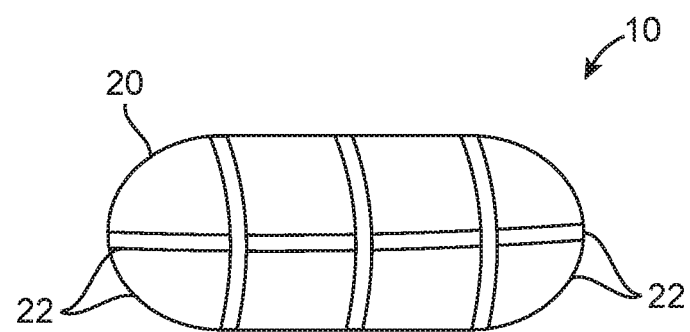
FIG. 9a shows an embodiment of a swallowable drug delivery device including a capsule having bio-degradable seams positioned to produce controlled degradation of the capsule in the GI tract.
Figure 9B:
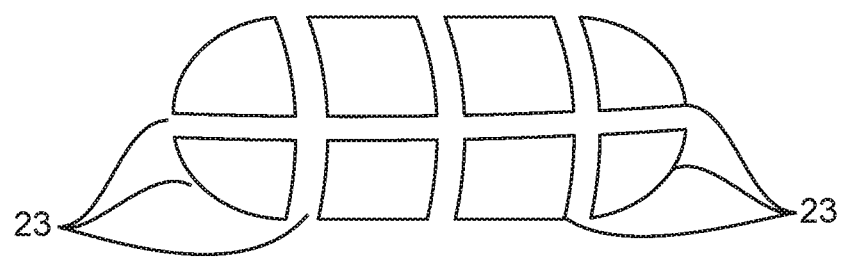
FIG. 9b shows the embodiment of FIG. 9a after having been degraded in the GI tract into smaller pieces.

After medication delivery, device 10 then passes through the intestinal tract including the large intestine LI and is ultimately excreted. For embodiments of the capsule 20 having biodegradable seams 22 or other biodegradable portions, the capsule is degraded in the intestinal tract into smaller pieces to facilitate passage through and excretion from the intestinal tract as is shown in the embodiments of FIGS. 9a and 9b. In particular embodiments having biodegradable tissue penetrating needles/members 40, should the needle get stuck in the intestinal wall, the needle biodegrades releasing the capsule 20 from the wall.

For embodiments of device 10 including a sensor 67, actuation of mechanism 60 can be effectuated by the sensor sending a signal to actuating mechanism 60 and/or a processor 29/controller 29c coupled to the actuating mechanism. For embodiments of device 10 including external actuation capability, the user may externally activate actuating mechanism 60 at a selected time period after swallowing the capsule. The time period can be correlated to a typical transit time or range of transit times for food moving through the user's GI tract to a particular location in the tract such as the small intestine.

One or more embodiments of the above methods can be used for the delivery of preparations 100 containing therapeutically effective amounts of a variety of drugs and other therapeutic agents 101 to treat a variety of diseases and conditions. These include a number of large molecule peptides and proteins which would otherwise require injection due to chemical breakdown in the stomach. The dosage of the particular drug can be titrated for the patient's weight, age or other parameter. Also the dose of drug 101 to achieve a desired or therapeutic effect (e.g., insulin for blood glucose regulation) when delivered by one or more embodiments of the invention can be less than the amount required should the drug have been delivered by conventional oral delivery (e.g., a swallowable pill that is digested in the stomach and absorbed through the wall of the small intestine). This is due to the fact that there is no degradation of the drug by acid and other digestive fluids in the stomach and the fact that all, as opposed to only a portion of the drug is delivered into the wall of the small intestine and/or peritoneal wall (or other lumen in the intestinal tract, e.g., large intestine, stomach, etc.). Depending upon the drug 101, the dose 102 delivered in preparation 100 can be in the range from 100 to 5% of a dose delivered by conventional oral delivery (e.g., a pill) to achieve a desired therapeutic effect (e.g., blood glucose regulation, seizure regulation, etc.) with even lower amounts contemplated. The particular dose reduction can be titrated based upon the particular drug, the amount of degradation occurring in the GI tract for conventional oral methods, the frequency of dosing vs dosing using embodiments of the swallowable capsule described herein, the condition to be treated, and the patient's weight, age and condition. For some drugs (with known levels of degradation in the intestinal tract) a standard dose reduction can be employed (e.g., 10 to 20%). Larger amounts of dose reduction can be used for drugs which are more prone to degradation and poor absorption. In this way, the potential toxicity and other side effects (e.g., gastric cramping, irritable bowel, hemorrhage, etc.) of a particular drug or drugs delivered by device 10 can be reduced because the ingested dose is lowered. This in turn, improves patient compliance because the patient has reduction both in the severity and incidence of side effects. Additional benefits of embodiments employing dose reduction of drug 101 include a reduced likelihood for the patient to develop a tolerance to the drug (requiring higher doses) and, in the case of antibiotics, for the patient to develop resistant strains of bacteria. Also, other levels of dose reduction can be achieved for patients undergoing gastric bypass operations and other procedures in which sections of the small intestine have been removed or its working (e.g., digestive) length effectively shortened.

In addition to delivery of a single drug, embodiments of swallowable drug delivery device 10 and methods of their use can be used to deliver a plurality of drugs for the treatment of multiple conditions or for the treatment of a particular condition (e.g., protease inhibitors for treatment HIV AIDS). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream, at about the same time. Due to difference in chemical makeup, molecular weight, etc., drugs can be absorbed through the intestinal wall at different rates, resulting in different pharmacokinetic distribution curves. Embodiments of the invention address this issue by injecting the desired drug mixtures at substantially the same time. This in turn, improves the pharmacokinetics and thus the efficacy of the selected mixture of drugs. Additionally, eliminating the need to take multiple drugs is particularly beneficial to patients who have one or more long term chronic conditions including those who have impaired cognitive or physical abilities.

In various applications, embodiments of the above methods can be used to deliver preparations 100 including drugs and therapeutic agents 101 to provide treatment for a number of medical conditions and diseases. The medical conditions and diseases which can be treated with embodiments of the invention can include without limitation: cancer, hormonal conditions (e.g., hypo/hyper thyroid, growth hormone conditions), osteoporosis, high blood pressure, elevated cholesterol and triglyceride, diabetes and other glucose regulation disorders, infection (local or systemic, e.g., septicemia), epilepsy and other seizure disorders, osteoporosis, coronary arrhythmia's (both atrial and ventricular), coronary ischemia anemia or other like condition. Still other conditions and diseases are also contemplated.

In many embodiments, the treatment of the particular disease or condition can be performed without the need for injecting the antibody or other therapeutic agent (or other non-oral form of delivery such as suppositories) but instead, relying solely on the therapeutic agent(s) that is delivered into the wall of the small intestine and/or peritoneal wall or other portion of the GI tract. Similarly, the patient need not take conventional oral forms of a drug or other therapeutic agent, but again can rely solely on delivery into the wall of the small intestine and/or peritoneal wall using embodiments of the swallowable capsule. In other embodiments, the therapeutic agent(s) delivered into the wall of the small intestine and/or peritoneal wall can be delivered in conjunction with an injected dose of the agent(s). For example, the patient may take a daily dose of therapeutic agent using the embodiments of the swallowable capsule, but only need take an injected dose every several days or when the patient's condition requires it (e.g., hyperglycemia). The same is true for therapeutic agents that are traditionally delivered in oral form (e.g., the patient can take the swallowable capsule and take the conventional oral form of the agent as needed). The dosages delivered in such embodiments (e.g., the swallowed and injected dose) can be titrated as needed (e.g., using standard dose response curve and other pharmacokinetic methods can be used to determine the appropriate dosages). Also, for embodiments using therapeutic agents that can be delivered by conventional oral means, the dose delivered using embodiments of the swallowable capsule can be titrated below the dosage normally given for oral delivery of the agent since there is little or no degradation of the agent within the stomach or other portion of the intestinal tract (herein again standard dose response curve and other pharmacokinetic methods can be applied).

Various embodiments of preparation 100 containing one or more drugs or other therapeutic agents 101 for the treatment of various diseases and conditions will now be described with references to dosages. It should be appreciated that these embodiments, including the particular therapeutic agents and the respective dosages are exemplary and the preparation 100 can comprise a number of other therapeutic agents described herein (as well as those known in the art) that are configured for delivery into a luminal wall in the intestinal tract (e.g., the small intestinal wall) using various embodiments of device 10. The dosages can be larger or smaller than those described and can be adjusted using one or more methods described herein or known in the art.

In a group of embodiments, therapeutic agent preparation 100 can comprise a therapeutically effective dose of growth hormone for the treatment of one or more growth disorders, as well as wound healing. In one embodiment, preparation 100 can contain a therapeutically effective amount of growth hormone in the range of about 0.1-4 mg, with particular ranges of 0.1-1, 1-4, 1-2, and 2-4 mg, with still larger ranges contemplated. The particular dose can be titrated based on one or more of the following factors: i) the particular condition to be treated and its severity (e.g. level and particular type of hypercholesterolemia or dyslipidemia); ii) the patient's weight; iii) the patient's age; and iv) the frequency of dosage (e.g. daily vs. twice daily).

Drug delivery compositions and components of known drug delivery systems may be employed and/or modified for use in some embodiments of the inventions described herein. For example, micro-needles and other microstructures used for delivery of drugs through the skin surface with drug patches may be modified and included within the capsules described herein and used to instead deliver a drug preparation into a lumen wall of the gastrointestinal tract such as the of the small intestine and/or peritoneal wall. Suitable polymer micro-needle structures may be commercially available from Corium of California, such as the MicroCor™ micro delivery system technology. Other components of the MicroCor™ patch delivery systems, including drug formulations or components, may also be incorporated into the capsules described herein. Alternatively, a variety of providers are commercially available to formulate combinations of polymers or other drug-delivery matrices with selected drugs and other drug preparation components so as to produce desired shapes (such as the releasable tissue-penetrating shapes described herein) having desirable drug release characteristics. Such providers may, for example, include Corium, SurModics of Minnesota, BioSensors International of Singapore, or the like.

One advantage and feature of various embodiments of the therapeutic compositions described herein is that by being enclosed or otherwise contained in the swallowable capsule or other swallowable device, the antibody (e.g. an AP-antibody such as Alirocumab) or other biologic (e.g. peptide or protein) drug payload is protected from degradation and hydrolysis by the action of peptidases and proteases in the gastrointestinal (GI) tract. These enzymes are ubiquitous throughout living systems. The GI tract is especially rich in proteases whose function is to break down the complex proteins and peptides in one's diet into smaller segments and release amino acids which are then absorbed from the intestine. The devices and compositions described herein are designed to protect the therapeutic peptide, antibody or other protein from the actions of these GI proteases and to deliver the peptide or protein payload directly into the wall of the intestine. There are two features in various embodiments of the compositions described herein which serve to protect the protein or peptide payload from the actions of GI proteases. First, in certain embodiments, the capsule shell, which contains the deployment engine and machinery, does not dissolve until it reaches the duodenal and sub-duodenal intestinal segments, owing to the pH-sensitive coating on the outer surface of the capsule which prevents its dissolution in the low pH of the stomach. Second, in certain embodiments, hollow polymer micro-spears (e.g., polyethylene oxide, maltose, silicone etc.) contain the actual therapeutic peptide or protein; the polymer micro-spears are designed to penetrate the intestine muscle as soon as the outer capsule shell dissolves; and the micro-spears themselves slowly dissolve in the intestinal muscle wall to release the drug payload. Thus, the peptide, antibody protein payload is not exposed to the actions of the GI proteases and therefore does not undergo degradation via proteolysis in the GI tract. This in turn, contributes to the high bioavailability of the therapeutic peptide or protein versus what would be expected if one or both of the above approaches were not used and the peptide or protein were exposed to the GI proteases. In particular for embodiments of the compositions comprising antibodies, such approaches preserve the binding affinity and specificity of the antibody allowing it to bind to the target antigen (e.g. one or more members of the PCSK9 family of cytokines)

Anti-PCSK9 Antibodies

As discussed above, various embodiments of the invention provide therapeutic compositions comprising antibodies or other binding proteins which attenuate the biological effects of PCSK9 and its analogues and derivatives by either binding to the PCSK9 molecule or it receptors for that PCSK9 so as to prevent in either case the PCSK9 from attaching to the receptor for that PCSK9.

A brief explanation will now be presented on PCSK9 molecules. This molecule is a serine protease encoded by a gene comprising 12 exons, located on chromosome 1p32.3. It is synthesized primarily by the liver and intestine as a 692-amino acid precursor (~75 kDa) in which a signal peptide (residues 1-30) and a prodomain (residues 31-152) precede a catalytic domain (residues 153-451) that contains the canonical N-H-S catalytic triad, followed by a C-terminal domain (residues 452-692). Pro-PCSK9 undergoes autocatalytic intramolecular processing between the Q152 and S153 residues in the endoplasmic reticulum to form a mature enzyme (~62 kDa). The cleavage of the prodomain is required for PCSK9 maturation and secretion. This was demonstrated by experiments where the prodomain and the catalytically inactive 62 kDa PCSK9 moiety were co-expressed, allowing the exit of a non-covalently bound PCSK9/prodomain complex from the endoplasmic reticulum to the Golgi complex, which ultimately promoted LDLR degradation. It is noteworthy that a naturally occurring amino acid substitution within the PCSK9 cleavage site (Q152H) has recently been described in a paper by Mayne J. T, et al (Novel loss-of-function PCSK9 variant is associated with low plasma LDL cholesterol in a French-Canadian family and with impaired processing and secretion in cell culture. 2011 Clin. Chem. 57: 1415-1423) which is fully incorporated herein for all purposes. This mutation prevents autocatalytic processing, thereby precluding PCSK9 secretion, and is associated with a 48% reduction in plasma LDL-C levels. After cleavage, the prodomain forms hydrogen bonds with key amino acids of the catalytic domain, thereby preventing access of other potential substrates to the catalytic pocket of PCSK9. The ability of PCSK9 to promote LDLR degradation is, therefore, independent of its catalytic activity, indicating that PCSK9 functions as a chaperone, a mode of action that is unique among serine proteases. PCSK9 undergoes self-assembly and forms PCSK9 dimers or trimers which have greater LDLR degrading activity. One of the gain-of-function (GOF) mutations of PCSK9 (D374Y) is characterized by an enhanced PCSK9 self-assembly. The main route of PCSK9 elimination is through LDLR binding, although LDLR-independent mechanisms of PCSK9 clearance must exist. Up to 30% of PCSK9 is bound to LDL-C in mice and normal lipidemic subjects. In mice, PCSK9 is also bound to high-density lipoprotein (HDL). The amino residues 31-52 of the prodomain are required for the binding of PCSK9 to LDL-C.

According to various embodiments, such anti-PCSK9 antibodies, herein AP-antibodies, may correspond to a full-length antibody or an antigen-binding portion thereof. Also, they will typically, though not necessarily, comprise monoclonal antibodies which are human or humanized antibodies using methods known in the art. As used herein, the term "antibody", refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Also, as used herein, "epitope" means a segment or feature of a protein capable of specific binding to an antibody. Also, as used herein, an "anti-PCSK9 antibody (AP-antibody)," "AP-antibody portion," or "AP-antibody fragment" and/or "AP-antibody variant" and the like include any protein or peptide containing molecule that comprises at least a portion of an immunoglobulin molecule, including, but not limited to at least one complementarity determining region (CDR) of a heavy or light chain or a ligand binding portion thereof, a heavy chain or light chain variable region, a heavy chain or light chain constant region, a framework region, or any portion thereof, or at least one portion of a PCSK9 receptor or binding protein, which can be incorporated into an antibody of the present invention. Such AP-antibodies optionally further affect a specific ligand, such as but not limited to where such an antibody modulates, decreases, increases, antagonizes, agonizes, mitigates, alleviates, blocks, inhibits, abrogates and/or interferes with PCSK9 activity or binding, or with PCSK receptor activity or binding, in vitro, in situ and/or in vivo. According to one or more embodiments, the PCSK9 antibodies may correspond to one or more of Alirocumab (available from Regeneron/Sanofi), Evolocumab (from Amgen), or Bococizumab (from Pfizer).

AP-antibodies or other binding protein provided by embodiments of the invention are particularly useful for treating hypercholesterolemia and various forms of cardiovascular disease including arteriolosclerosis and/or coronary, cerebral and peripheral vascular stenosis and related conditions. Specific forms of hypercholesterolemia which can be treated included without limitation heterozygous familial hypercholesterolemia, and homozygous familial hypercholesterolemia. Such embodiments result in the delivery of AP-antibody with particular pharmacokinetic properties which are advantageous verses intravenous, sub-dermal or intramuscular injection. They also allow for the usage of dosages which provide one or more of the following benefits including higher therapeutic ratio, reduced incidence of allergic reaction (including e.g., anaphylactic shock; myalgia and neurocognitive and ophthalmologic events, the latter two observed during clinical trials of Alirocumab) and reduced immunogenicity and/or immunogenic reaction (verses subcutaneous and/or intramuscular injection). In one embodiment, the reduced incidence of allergic reaction can be determined by comparison of such incidences for patient populations who are delivered drug by standard injection (e.g., intramuscular, intravenous etc.) vs the oral delivery for traditional compounds and then using that reduction to model a predicted reduction for known incidences of allergic reaction in patient populations for one or more of the AP antibodies described herein (e.g., Alirocumab, Evolocumab, Bococizumab) etc.

Dosage

According to one or more embodiments, the dosage of AP-antibody administered using one or more embodiments of the swallowable capsule is usually, though not necessarily, a therapeutically effective amount. As used herein, the phrase "therapeutically effective amount" means a dose of anti-AP antibody that results in: i) a detectable improvement in one or more clinical measurements (e.g. serum cholesterol and/or lipid levels) and/or symptoms of hypercholesterolemia and/or dyslipidemia in a patient; or ii) a dose of AP-antibody that inhibits, prevents, lessens, or delays the progression of hypercholesterolemia and/or dyslipidemia in a patient e.g., such as i) the development of arteriosclerosis; ii) coronary stenosis and/or ischemia; or iii) peripheral artery stenosis or ischemia. According to various embodiments, a therapeutically effective amount of AP-antibody delivered by embodiments of the invention can be in a range from about 0.05 mg to about 200 mg, with specific embodiments of about 0.05 mg, about 0.1 mg, about 1.0 mg, about 1.5 mg, about 2.0 mg, about 5 mg, about 7, about 10 mg, about 11 mg, about 12 mg, about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, of the anti-PCSK9 antibody.

Embodiments of PCSK9 Neutrializing Proteins Comprising Alirocumab, Evolocumab or Bococizumab In one or more embodiments, the AP-antibodies may correspond to one or more of Alirocumab, Evolocumab or Bococizumab and their analogue and derivatives. Alirocumab is a fully human monoclonal antibody to PCSK9. It binds to and inhibits and/or neutralizes the activity of PCSK9 which as described above has been implicated in lowering the LDL-cholesterol or hyperlipidemia, a risk factor for the development of atherosclerosis and associated ischemic cardiovascular disease (CVD), such as myocardial infarction and stroke. Positive results from clinical study were published and won a priority review by the FDA.

From its use as a monotherapy during clinical trials, Alirocumab has been shown to reduce LDL-C as much as intensive statin treatment and in conjunction with statin, Alirocumab significantly enhanced reduction of serum levels of LDL-C. For example, among patients with baseline LDL-C≥100 mg/dL on atorvastatin 10 mg daily, an increase in atorvastatin to 80 mg daily resulted in a further 17% decrease in LDL-C, whereas an increase in atorvastatin to 80 mg daily along with Alirocumab 150 mg every 2 weeks resulted in a further 73% decrease. The Alirocumab group, as compared with the placebo group, had higher rates of injection-site reactions (5.9% vs. 4.2%), myalgia (5.4% vs. 2.9%), neurocognitive events (1.2% vs. 0.5%), and ophthalmologic events (2.9% vs. 1.9%). In a post hoc analysis, the rate of major adverse cardiovascular events (death from coronary heart disease, nonfatal myocardial infarction, fatal or nonfatal ischemic stroke, or unstable angina requiring hospitalization) was lower with Alirocumab than with placebo (1.7% vs. 3.3%; hazard ratio, 0.52; 95% confidence interval, 0.31 to 0.90; nominal P=0.02). (ODYSSEY LONG TERM ClinicalTrials.gov number, NCT01507831).

The doses of Alirocumab for such treatment can be delivered using various embodiments of the swallowable devices including swallowable capsules (described herein) and can be in a range from about 1 to 50 mg per day, with specific embodiments of about 5, 10, 20, 25, 30 and 40 mg per day. In preferred embodiments for the treatment of hyperlipidemia, the dose of Alirocumab delivered using embodiments of the swallowable capsule can be in a range of about 5 to 11 mg per day, with specific embodiments of 5, 5.5, 6, 7, 8, 9, 10.0, 10.5 and 10.7 mg per day for various forms of hypercholesterolemia and/or dyslipidemia. Similar dosages may be used for embodiments for delivering AP-antibodies corresponding to one or both of Evolocumab or Bococizumab or their analogues and derivatives. In particular embodiments using Evolocumab, doses of 5, 6, 7, 8, 9 and 9.3 mg can be delivered per day for various forms of hypercholesterolemia and/or dyslipidemia and 14 mg per day for patients with homozygous familial hypercholesterolemia. In particular embodiments using Bococizumab doses of 7, 8, 9, 10, 10.7 and 11 mg per day can be delivered for treating various forms of hypercholesterolemia and/or dyslipidemia. These doses can be delivered by means of one or more swallowable capsules (including multiple capsules taken at the same time) taken at once or over the course of a day. For these and other dosages, the daily dose may be initiated after a loading dose which may be administered via injection (e.g., IV, intramuscular or subdermal) or other delivery method. The dose may be titrated for an individual patient based on one or more of the patient's, weight, age, severity of condition, combination with other drugs, duration of the drug regimin, amount of the loading dose and treatment efficacy index known in the art for a given condition. For example in the case of Bococizumab, initial dosing can be adjusted to achieve reductions in (LDL-C) of about 40 to 60 mg/dl with a specific range of about 50 to 54 mg/dl in serum low-density lipoprotein cholesterol. Correspondingly doses of of the selected AP-antibody (e.g. Alirocumab, Evolocumab or Bococizumab) can be delivered to reduce percent amount of LDL-C or serum lipids in a range from about 10 to 80%, with specific embodiments of 20, 30, 40, 46, 50, 60, or 70. After a desired reduction in in LDL-C or lipids has been achieved, then the dosage of the delivered antibody can then be decreased or otherwise titrated accordingly. For example dosages of the AP-antibody can then be reduced once LDL-C levels in patients have been decreased to ≤25 mg/dl. Also in related embodiments, once some level of LDL-C levels reduction has been achieved dosages can be redured from about 32 to about 35% % after 8 to 10 weeks of delivery.

Embodiments of Combination Therapies for LDL-C Reduction Using PCSK9 Neutralizing Proteins.

In alternative or additional embodiments for reducing LDL-C levels in a patient, the oral delivery of PCSK9 neutrializing proteins (e.g., using embodiments of the swallowable capsule) may be combined with other therapies for achieving such a reduction including the use of various orally delivered agents for reducing LDL-C levels. The orally delivered dose of the LDC-reducing agent may given selected time before, concurrently or after the patient takes an oral dose of PCSK9 neutralizing proteins (e.g, a PN-antibody such as Alirocumab) using embodiments of the swallowable capsule. In many embodiments the orally delivered LDL-C reducing agents may correspond to one or more statins. In particular embodiments the statin may correspond to atorvastatin and its analogues. For example, according to one or embodiments an orally delivered dose of atorvastatin may taken before, during or after the patient takes a swallowable dose of a PN-antibody, such as Alirocumab, Evolocumab or Bococizumab. The dose of the atorvastatin may be in the range of about 10 mg to 80 mg daily. In use such combination therapies such as the oral delivery of Alirocumab and atorvastatin can provide for additional levels of LDL-C levels reduction than possible with individual administration of each medication alone. For example, for an approximate 80 mg daily oral dosage of atorvastatin combined with an approximate 10.7 mg daily dosage of Alirocumab additional decreases in LDL-C levels of up to 73% may be achieved. According to various embodiments, the dose of orally delivered PN-antibody and other LDL-C reducing agent (e.g atorvastatin) may adjusted relative to one another (depending on various factors, e.g the pateints initial LDC-levels, weight, age, etc) to optimize or otherwise achieve a selected level of LDL-C reduction in the patent. Further the dose of the two LDL-C reducing agents and their times of delivery can be adjusted so as to achieve a synergistic effect in LDL-C reduction. According, to one or more embodiments, the doses of each agent for producing such a synergistic effect and/or LDC-C reduction optimization can be determined by using known dose responsive curves for each medication and then using pharmacodynamic and/or pharmacokinetic models to predict the dose which produces the optimal levels of LDC-C reduction. Such models may correspond to one or more of exponential, first order, second order, differential equation or other model known in the pharmaceutical or biochemical art. The models may also correspond to various network models known in the pharmaceutical and biological arts including, for example, protein-protein interaction networks (or PPI network which are based on intentional physical or functional associations between proteins) such as that described by D Chen, et al in *Systematic Synergy Modeling: Understanding Drug Synergy From A Systems Biology Perspective*, BMC Syst Biol. 2015; 9: 56 which is incorporated by reference herein for all purposes. Another example of a suitable network model includes an enhanced Petri-Net (EPN) model such as that described by G. Jin et al in *An Enhanced Petri-Net Model To Predict Synergistic Effects Of Pairwise Drug Combinations From Gene Microarray Data*. Bioinformatics Volume 27, Issue 13 P 310-316 which is also incorporated by reference herein for all purposes. In still another approach, dose response curves using combinations of AP-antibody and other LDL-C reducing agent can then be developed and used with with one or more of the aforementioned models to predict dosages for optimizing an LDL-C reducing effect.

Alternative Embodiments of PCSK9 Neutralizing Proteins.

Other embodiments of the invention contemplate the oral delivery of other PCSK9 neutralizing proteins and or polypeptides which may correspond to one or more of adnectins, memetic peptides, small molecule inhibitors, antisense oligonucleotides, and RNA interence (RNA-i) compounds.

Suitable adnectins include BMS-962476. Suitable mimetic peptides include EGF-AB peptide fragment, LDLR Sub-fragment and LDLR DNA constructs. Suitable small molecule inhibitors include SX-PCK9. Suitable antisense oligonucleotides include ISIS394814 and SPC 4061. Suitable RNA-I compounds include ALN-PCS02. Further description of these and other PCSK9 neutralizing proteins including specific molecules, their properties, dosages and sources may be found in the table shown in FIG. 21.

Benefits of Delivery of AP-Antibodies into the Intestinal Wall or Other Location in the Intestinal Tract.

In use, embodiments of the invention providing for delivery of an AP-antibody or PN-protein into wall of the intestine and/or peritoneal wall and adjoining tissue (e.g the peritinoeam) or other target site in the intestinal tract e.g the larger intestine) for treatment of one or more of the above or conditions provide a number of benefits over injected forms AP-antibodies such as Alirocumab, Evolocumab and Bococizumab. Such benefits can include without limitation: i) a higher therapeutic ratio; ii) reduced incidence and severity of the adverse reactions including one or more of: anaphylactic shock or other allergic reaction (including at the injection site), bruising at the injection site, nasopharyngitis, upper respiratory tract infections, influenza, back pain myalgia, neurocognitive events, and ophthalmologic events; and decreased immunogenicity and/or immunogenetics reaction. In the later case, such immunogenic reactions can result in the development in the patient of antibodies to the AP antibodies themselves resulting in reduced efficacy resulting in the requirement of higher doses of drug and/or an unwanted immune response. These benefits are due to one or more of the following i) the much smaller doses of AP-antibodies or (or other AP-antibody or PN-protein) that are delivered by embodiments of the invention; ii) doses are delivered daily vs weekly or monthly; and iii) the fact that doses are delivered orally vs intravascularly.

In many embodiments, the therapeutic ratio of dosages of AP-antibodies delivered orally by embodiments of the invention can be increased significantly over that for AP-antibody(s) delivered by injection (e.g., intravenously, intramuscularly, or subcutaneously, etc on a weekly, biweekly, or monthly basis). In various embodiments, the term "significantly" corresponds to an increase in the therapeutic ration in an amount of two times or greater, e.g, seven to thirty times greater or more. For AP-antibodies or (or other AP-antibody or PN-protein) that are typically delivered in weekly doses when injected (e.g intravenously, intramuscularly, or subcutaneously, etc), the therapeutic ratio (e.g Toxic Dose/Effective Dose) can be increased by a factor of seven when delivered in daily oral doses using the swallowable devices provided by the invention, while in the case of monthly injected doses of AP antibodies the therapeutic ration can be increased by a factor of 30 when delivered daily oral doses by embodiments of the invention. Further, increases can be obtained when the oral dose of AP-antibody is given multiple times over a day. Similar improvements (e.g by a factor of 7, 30 or even more) can be seen in the incidence in one or more of immunogenicity/immune response (vs intramuscular and/or subcutaneous injection), allegeric reaction, and other adverse reactions. Immunogenicity/immune response, being the production by the body of antibodies to the administered AP-antibody which neutralize or otherwise diminish the clinical efficacy of the AP-antibody. The reduction in the incidence and severity of allergic reaction can be reduced by a factor of two up to 30 due to the fact the antibodies are given in daily doses vs monthly doses which tends to desensitize the immune system (the degree of allergic reaction can be determined using methods known in the art and may be correlated to one or more in vitro tests known in the art). Similarly, the degree of reduced immunogenicity and/or immune response can be reduced by a factor of two to as much as thirty or more due three possible factors: 1) the doses are not delivered subcutaneously and/or intramuscularly (which tend to exacerbate such responses); 2) the doses are delivered in much smaller amounts, e.g by a factor of 7 to as much as 30 depending on whether the injected dose is delivered weekly, biweekly, monthly etc; and 3) as discussed above the dose of AP-antibody is delivered to the upper portions of the small intestine avoiding the peyer's patches and subsequent production of immune cells and other immune response. The amount of immune response/immunence to a given AP-antibody (e.g., Alirocumab) can be quantified using one more more immunologic analytical methods known in the art to measure, for example, the production of generated antibodies to the delivered AP-antibody or other PN-protein and/or the percentage of the administered AP-antibodies that are neutralized by the patients own antibodies. In these and related embodiments, the dosage and dose regiment of the AP-antibody can configured to yield a minimal immune response in the patient, wherein minimal means less than 10% of the delivered AP-antibodies are neutralized by the patients own antibodies and more preferrably less than 5%.

In other embodiments the immune response and/or allergic response to the administered AP-antibody can be quantified by measuring differences in the serum titer of antibodies to the AP-antibody when administered in daily oral doses vs biweekly or monthly intravenous doses. In these and related embodiments, the dosage and dose regiment of the AP-antibody can configured to yield a minimal immune response in the patient, wherein minimal means less than a 10% increase in the serum concentration of the patient's own antibodies against the administered AP-antibody and more preferrably less than a 5% increase.

In related approaches, the serum titer of cytokines (e.g interleukins, such as interleukin 7) and/or white blood cells can be measured for each form of administration. In these and related embodiments, the dosage and dose regiment of the AP-antibody can configured to yield a minimal immune response in the patient, wherein minimal means less than a 10% increase in the serum concentration of one or more of the patients white blood cells and/or a particular cystokine (e.g., interleukin 7) and more preferrably less than a a 5% increase. In related embodiments, immune response can be quantified by using changes in white blood cell differentials (e.g increase in the % of Eosinophils or Basophils which occur in allergic reactions). In these and related embodiments, the dosage and dose regiment of the AP-antibody can configured to yield a minimal immune response in the patient, wherein minimal means less than a 10% change in the percentage of a particular type of white blood cell (e.g., Eosinophils) in the patient's total white blood cell count.

Another benefit achieved by delivering doses of various AP-antibodies or other PN-protein in daily doses versus biweekly or monthly doses by conventional injection means (e.g. by intravenous, intramuscular or subcutaneous injection) is a reduction in the fluctuation of the patients plasma concentration profile for the particular antibody which in turn results in a much smoother plasma concentration profile. Using a pharmacokinetic model explained in more detail in Appendix 1, plasma concentration curves were generated for the delivery of Alirocumab (FIGS. 22a and 22b) in biweekly delivery periods verses daily doses (which were titrated down from biweekly dose). As can be seen from the figures, the amount of daily fluctuation in the curves is much less for Alirocumab. Also a value known as "% steady state fluctuation" was calculated for each of these antibodies using an equation shown and described in detail in Appendix 2. The value reflects the amount of daily fluctuation in the plasma concentration of a given drug. As shown in Table 1 below, the amount of steady state fluctuation in plasma concentration of the particular antibody was reduced significantly when the antibody was delivered by embodiments of the invention in daily doses vs subcutaneous injection (66.3% to 0.39%). With the result being about a 170 times reduction in steady state fluctuation for Alirocumab. The model has also been used to show reductions in steady plasma fluctuations for two anti-interleukin antibodies: Secukinumab and Brodalumab (as is described in U.S. patent application Ser. No. 15/150,379) with results shown in Table 2. In these cases, the reductions in steady fluctuation were from 171 to 216x. Thus, the model consistently show reductions of 170 to 216% in the steady plasma concentrations of a given drug (e.g. AP-antibody) when the drugs is given in daily doses using embodiments of the invention vs biweekly or monthly using subcutaneous injections. Using such a model, similar absolute values (e.g., 0.12 to 0.39%) and reductions are expected for Evolocumab or Bococizumab in % steady state fluctuation. The benefits of such reductions include one more of the following: reduced risk of adverse event, reduced allergic reaction and immunogenicity; as well longer period of time when the patient is kept in the therapeutic index (range) for a given antibody allowing the antibody to better and more consistently treat the intended condition. The reduced steady state fluctuation may also be used to quantify a reduction in the patient's immune response to a particular AP-antibody. Such a reduction may be proportional (e.g. directly proportional, fractionally proportion, etc.) or in the form of first order or second order proportionality.

TABLE 1

% Steady State Fluctuation in Plasma/Serum Concentration of Alirocumab using conventional subcutaneous dosing of the drug vs daily dosing by embodiments of the invention.

|  | Alirocumab |
|---|---|
| Conventional Subcutaneous dosing | 66.33% |
| Daily Dosing via Embodiments of the invention | 0.39% |
| Decrease in Steady Fluctuation | 170x |

TABLE 2

% Steady State Fluctuation in Plasma/Serum Concentration of Secukinumab and Brodalumab using conventional subcutaneous dosing of the drug vs daily dosing by embodiments of the invention.

|  | Secukinumab | Brodalumab |
|---|---|---|
| Conventional Subcutaneous dosing | 56.15% | 20.48% |
| Daily dosing using embodiments of the invention | 0.26% | 0.12% |
| Decrease in Steady Fluctuation | 216x | 171x |

Embodiments of Bioequivalents of AP-Antibodies

Embodiments of the invention also contemplate the compositions and use of AP antibodies and antibody fragments which encompass proteins having amino acid sequences that vary from the AP-antibodies described herein. Such variant AP antibodies and antibody fragments comprise one or more additions, deletions, or substitutions of amino acids (e.g. leucine vs lysine) when compared to the amino-acid sequence of a parent AP-antibody, but exhibit biological activity that is essentially equivalent to that of the described AP antibodies in terms of the ability of the variant to bind and/or neutralize a PCSK9 molecule.

Embodiments of Methods of Treating Hypercholesterolemia and/or Dyslipidemia Using AP Antibodies Delivered into the Intestinal Wall.

In one or more embodiments, the invention provides methods for treating high cholesterol or other form of hypercholesterolemia and/or dyslipidemia comprising: i) administering a dose of PCSK9 antibody to the patient using one or more embodiments of the swallowable capsule described herein; ii) monitoring a cholesterol and/or lipid level of the patient in response to the administered PCSK9; and then iii) titrating the subsequent doses and/or dosing regiments accordingly. Specific PCSK9 antibodies which can be administered to the patient using embodiments of the invention may correspond to one or more of Alirocumab, Evolocumab or Bococizumab as well as their analogues and derivatives. Specific forms of hypercholesterolemia which can be treated include without limitation, heterozygous familial hypercholesterolemia, and homozygous familial hypercholesterolemia (related conditions such as arteriolosclerosis can also be treated with such methods). Higher doses of one or AP-antibodies may delivered depending upon the particular initial level of cholesterol and/or particular type of hypercholesterolemia. For example, in the case of homozygous familial hypercholesterolemia larger doses can be given of the selected AP-antibody such as Evolocumab. In particular embodiments, a daily dose of around 13 to 15 mg of Evolocumab can be given, with a specific embodiment of about 14 mg per day. Also doses can be titrated down once a desired reduction in LDL-C and/or serum lipid levels have been achieved. For example according to one or more embodiments, dosages of the AP antibodies can then be reduced once LDL-C levels in patients have been decreased to ≤25 mg/dl. The dosages may also be reduced after a number of weeks of treatment, for example, reductions from about 32 to about 35% % after 8 to 10 weeks of delivery. In additional or supplemental embodiments, genetic testing can be performed on the patient prior to AP-antibody administration to determine one or more of the following: i) the most therapeutically effective AP antibody to use (e.g., that producing the greatest reduction in PCSK9 levels, e.g. Alirocumab, Evolocumab, etc.), ii) the type and amount of adverse reactions for a given AP-antibody (t e.g., inflammation and degree of); iii the most effective dosage and/or dose frequency for a given AP-antibody (e.g. vs Alirocumab, Evolocumab etc.). Genetic testing can using techniques known in the art can be done looking at single or groups of genes and can also be done to look for the presence of more of single nucleotide polymorphisms (SNP), multiple nucleotide polymorphism (MNP. Further such testing for one of the results listed above can be correlated to results for similar antibodies to the AP antibodies or antibodies in antibody families to which AP-antibodies belong.

Pharmacokinetic Metrics for Delivery of AP-Antibodies into the Intestinal Wall

Embodiments of the invention delivering AP-antibodies or other PN proteins into the intestinal wall (e.g., the small intestine) also provide benefits with regard to one or more pharmacokinetic metrics. Pharmacokinetic metrics of note in this regard include without limitation, $C_{max}$, the peak plasma concentration of a drug after administration; $t_{max}$, the time to reach $C_{max}$; and $t_{1/2}$, the time required for the plasma concentration of the drug to reach half its $C_{max}$ value after having reached $C_{max}$. These metrics can be measured using standard pharmacokinetic measurement techniques known in the art. For example, one approach plasma samples may be taken at set time intervals (e.g., one minute, five minutes, ½ hour, 1 hour, etc.) beginning and then after administration of the AP-antibody or other therapeutic agent either by use of a swallowable device or by non-vascular injection. The concentration of the drug in plasma can then be measured using one or more appropriate analytical methods such as GC-Mass Spec, LC-Mass Spec, HPLC or various ELISA (Enzyme-linked immunosorbent assays) which can be adapted for the particular drug. A concentration vs. time curve (also herein referred to as a concentration profile) can then be developed using the measurements from the plasma samples. The peak of the concentration curve corresponds to $C_{max}$ and the time at which this occurs corresponds to $t_{max}$. The time in the curve where the concentration reaches half its maximum value (i.e., $C_{max}$) after having reached $C_{max}$ corresponds to $t_{1/2}$ this value is also known as the elimination half-life of the drug. The start time for determination of $C_{max}$ can be based on the time at which the injection is made for the case on non-vascular injection and the point in time at which embodiments of the swallowable device advances one or more tissue penetrating members (containing the drug) into the small intestine or other location in the GI tract (e.g., the large intestine). In the latter case, this time can determined using one or more means including a remote controlled embodiment of the swallowable device which deploys the tissue penetrating members into the intestine wall in response to an external control signal (e.g., an RF signal) or for an embodiment of the swallowable device which sends an RF or other signal detectable outside the body when the tissue penetrating members have been deployed. Other means for detection of tissue penetrating member deployment into the small intestine are contemplated such as one more medical imaging modalities including for example, ultrasound or fluoroscopy. In any one of these studies, appropriate animal models can be used for example, dog, pig, rat etc. in order to model the human pharmacokinetic response.

Thus, various embodiments provide a therapeutic composition 100 (also referred to herein as a preparation) comprising an AP-antibody or other PN proteins. The composition is adapted for insertion into an intestinal wall after oral ingestion, wherein upon insertion, the composition releases AP-antibody into the bloodstream from the intestinal wall to achieve a $C_{max}$ faster than an extravascularly injected dose of AP-antibody that is to say, achieving a $C_{max}$ for the inserted form of AP-antibody in a shorter time period (e.g., a smaller $t_{max}$) than that for a dose of AP-antibody that is injected extravascularly. Note, that the dose of AP-antibody in the composition delivered into the intestinal wall and the dose delivered by extravascular injection, may, but need not, be comparable to achieve these results. In various embodiments, the composition is configured to achieve a $t_{max}$ for AP-antibody (e.g., by release of AP-antibody into the bloodstream from the intestinal wall, e.g., that of the small intestine) which is about 80%, or 50%, or 30%, or 20%, or 10% of a $t_{max}$ for an extravascularly injected dose of AP-antibody. Such an extravascularly injected dose of AP-antibody can be, for example, a subcutaneous injection or an intramuscular injection. In certain embodiments, the $C_{max}$ attained by delivering AP-antibody by insertion into the intestinal wall is substantially greater, such as 5, 10, 20, 30, 40, 50, 60, 70, 80 or even a 100 times greater, than the $C_{max}$ attained when the AP-antibody is delivered orally without insertion into the intestinal wall for example by a pill other convention oral form of AP-antibody or related compound. In some embodiments, the AP-antibody (or other PN protein) composition is configured to produce a long-term release of AP-antibody which can include periods in the range of about 1 to 60 days, with particular embodiments of 6 to 12 hours, 6 to 24 hours, 12 to 24 hours, 12 to 36 hours, 1 to 2 days, 1 to 5 days, 1 to 10 days, 1 to 20 days, two days, three days, five days, seven days, ten days, 15 days, 20 days, 30 days, 40 days, 45 days 50 days and 60 days. Also, the composition can be configured to produce a long-term release of AP-antibody with a selectable $t_{1/2}$. For example, the selectable $t_{1/2}$ may be 6, or 9, or 12, or 15 or 18, 24, 36, 48 and 60 hours.

Any appropriate dose of AP-antibody (or other PN protein) for a particular patient may be used, depending on factors such as weight, age, condition, other drugs being taken etc. For example, the dose of AP-antibody or other AN protein administered may range from about 1 to 10 mg, with particular ranges of 1-5, 1-4, 2-4, 2-5 and 2-3 mg and individual doses of 1, 2, 3, 4, 5, 6, 7, 8, 9 and 10 mg. When administered subcutaneously, AP-antibody typically has a $t_{max}$ in the bloodstream of about 130 hours. Therefore, when administered in a therapeutic AP-antibody composition as described herein, the $t_{max}$ of the AP-antibody will be shortened, e.g., to about 80%, or 50%, or 30%, or 20%, or 10% of the $t_{max}$ for AP-antibody when it is subcutaneously injected.

Various embodiments also provide an AP-antibody (or other PN-protein) composition adapted for insertion into an intestinal wall after oral ingestion, wherein upon insertion, the composition releases the AP-antibody (or other PN-protein) into the blood stream from the intestinal wall to achieve a $t_{1/2}$ that is greater than a $t_{1/2}$ for an orally ingested dose of AP-antibody (or other PN-protein) that is not inserted into the intestinal wall. For example, the $t_{1/2}$ of the dose inserted into the intestinal wall may be 100 or 50 or 10 or 5 times greater than the dose that is not inserted into the intestinal wall.

According to one or more embodiments, the AP-antibody (or other PN-protein) may be in solid form, such as a solid form composition configured to degrade in the intestinal wall such as the wall of the small intestine or the perineal wall. Also, the solid form composition may have, for example, a tissue penetrating feature such as a pointed tip. In one or more embodiments, the solid form AP-antibody composition may be in the form of a shaft with a pointed tip, such as needle or dart, allowing the composition to be penetrate and be inserted into the intestinal wall or peritoneal wall. The AP-antibody (or other PN-protein) composition may comprise at least one biodegradable material and/or may comprise at least one pharmaceutical excipient, including a biodegradable polymer such as PGLA or a sugar such as maltose. In other embodiments, the AP-antibody (or other PN-protein) may in a semi-solid or liquid form encased or otherwise fabricated into embodiments of the tissue penetrating member.

Various embodiments of the AP-antibody (or other PN-protein) composition described herein may be adapted to be orally delivered in a swallowable capsule. In certain embodiments such a swallowable capsule may be adapted to be operably coupled to a mechanism having a first configuration and a second configuration, the AP-antibody (or other PN-protein) composition being contained within the capsule in the first configuration and advanced out of the capsule and into the intestinal wall in the second configuration. Such an operably coupled mechanism may comprise at least one of an expandable member, an expandable balloon, a valve, a tissue penetrating member, a valve coupled to an expandable balloon, or a tissue penetrating member coupled to an expandable balloon.

In some embodiments, the AP-antibody (or other PN-protein) may be configured to be delivered within a lumen of a tissue penetrating member and/or the AP-antibody (or other PN-protein) composition may be shaped as a tissue penetrating member advanceable into the intestinal wall. The tissue penetrating member may be sized to be completely contained within the intestinal wall, and/or it may include a tissue penetrating feature for penetrating the intestinal wall, and/or it may include a retaining feature for retaining the tissue penetrating member within the intestinal wall. The retaining feature may comprise, for example, a barb. In some embodiments, the tissue penetrating member is configured to be advanced into the intestinal wall by the application of a force (e.g., a mechanical force) to a surface of the tissue penetrating member. Desirably, the tissue penetrating member has sufficient stiffness and/or column strength to be advanced completely into the intestinal wall and/or the surface of the penetrating member by the application of the mechanical or other force (e.g., electromagnetic). In various embodiments, the column strength/stiffness of the tissue penetrating member can range from about 1 to 20 lbs, 7 to 20 lbs, 8 to 12 lbs, with individual embodiments of 7, 8, 9, 10 and 11 lbs. The column strength can be achieved by selection of one or more of the material selection and diameter of the tissue penetrating member. In many embodiments, the tissue penetrating member is configured to be operatively coupled to an expandable balloon or other expandable member which applies the force upon expansion. In some embodiments, the tissue penetrating member is configured to be directly coupled to a structure applying the force (e.g. a spring, a shaft and the like or even an expandable device). In these and related embodiments, the tissue penetrating member is configured to detach from a structure applying the force when a direction of the force changes.

Various aspects of the invention also provide other embodiments of a swallowable delivery device for the delivery of medications 100 in addition to those described above. According to one or more such embodiments, the swallow delivery device can include one or more expandable balloons or other expandable devices for use in delivering one or more tissue penetrating members including medication 100 into the wall of an intestine, such as the small intestine. Referring now to FIGS. 12-20, another embodiment of a device 110 for the delivery of medication 100 to a delivery site DS in the gastro-intestinal (GI) tract, can comprise a capsule 120 sized to be swallowed and pass through the intestinal tract, a deployment member 130, one or more tissue penetrating members 140 containing medication 100, a deployable aligner 160 and a delivery mechanism 170. In some embodiments, medication 100 (also referred to herein as preparation 100) may itself comprise tissue penetrating member 140. The deployable aligner 160 is positioned within the capsule and configured to align the capsule with the intestine such as the small intestine. Typically, this will entail aligning a longitudinal axis of the capsule with a longitudinal axis of the intestine; however, other alignments are also contemplated. The delivery mechanism 170 is configured for delivering medication 100 into the intestinal wall and will typically include a delivery member 172 such as an expandable member. The deployment member 130 is configured for deploying at least one of the aligner 160 or the delivery mechanism 170. As will be described further herein, all or a portion of the capsule wall is degradable by contact with liquids in the GI tract so as to allow those liquids to trigger the delivery of medication 100 by device 110. As used herein, "GI tract" refers to the esophagus, stomach, small intestine, large intestine and anus, while "Intestinal tract" refers to the small and large intestine. Various embodiments of the invention can be configured and arranged for delivery of medication 100 into both the intestinal tract as well as the entire GI tract.

Device 110 including tissue penetrating member 140 can be configured for the delivery of liquid, semi-liquid or solid forms of medication 100 or combinations of all three. Whatever the form, medication 100 desirably has a material consistency allowing the medication to be advanced out of device 110, into the intestinal wall (small or large intestine) or other luminal wall in the GI tract and then degrade within the intestinal wall to release the drug or other therapeutic agent 101 into the wall and then into the blood stream. The material consistency of medication 100 can include one or more of the hardness, porosity and solubility of the preparation (in body fluids such as those found in the wall of the small intestine). The material consistency can be achieved by selection and use of one or more of the following: i) the compaction force used to make the preparation; ii) the use of one or more pharmaceutical disintegrants known in the art; iii) use of other pharmaceutical excipients; iv) the particle size and distribution of the preparation (e.g., micronized particles); and v) use of micronizing and other particle formation methods known in the art.

Capsule 120 is sized to be swallowed and pass through the intestinal tract. The size can also be adjusted depending upon the amount of drug to be delivered as well as the patient's weight and adult vs. pediatric applications. Typically, the capsule will have a tubular shape with curved ends similar to a vitamin. In these and related embodiments, capsule lengths 120L can be in the range of 0.5 to 2 inches and diameters 120D in the range of 0.1 to 0.5 inches with other dimensions contemplated. The capsule 120 includes a capsule wall 121w, having an exterior surface 125 and an interior surface 124 defining an interior space or volume 124v. In some embodiments, the capsule wall 121w can include one or more apertures 126 sized for the outward advancement of tissue penetrating members 140. In addition to the other components of device 110, (e.g., the expandable member etc.) the interior volume can include one or more compartments or reservoirs 127.

The capsule can be fabricated from various biodegradable gelatin materials known in the pharmaceutical arts, but can also include various enteric coatings 120c, configured to protect the cap from degradation in the stomach (due to acids etc.), and then subsequently degrade in the in higher pH's found in the small intestine or other area of the intestinal tract. In various embodiments, the capsule 120 can be formed from multiple portions one or more of which may be biodegradable. In many embodiments, capsule 120 can be formed from two portions 120p such as a body portion 120p" (herein body 120p") and a cap portion 120p' (herein cap 120p), where the cap fits onto the body, e.g., by sliding over or under the body (with other arrangements also contemplated). One portion, such as the cap 120p', can include a first coating 120c' configured to degrade above a first pH (e.g., pH 5.5) and the second portion such as the body 120p" can include a second coating 120c" configured to degrade above a second higher pH (e.g. 6.5). Both the interior 124 and exterior 125 surfaces of capsule 120 are coated with coatings 120*c*' and 120*c*" so that that either portion of the capsule will be substantially preserved until it contacts fluid having the selected pH. For the case of body 120*p*" this allows the structural integrity of the body 120*p*"' to be maintained so as to keep balloon 172 inside the body portion and not deployed until balloon 130 has expanded. Coatings 120*c*' and 120*c*" can include various methacrylate and ethyl acrylate based coatings such as those manufactured by Evonik Industries under the trade name EUDRAGIT. These and other dual coating configurations of the capsule 120 allows for mechanisms in one portion of capsule 120 to be actuated before those in the other portion of the capsule. This is due to the fact that intestinal fluids will first enter those portions where the lower pH coating has degraded thus actuating triggers which are responsive to such fluids (e.g., degradable valves). In use, such dual coating embodiments for capsule 120 provide for targeted drug delivery to a particular location in the small intestine (or other location in the GI tract), as well as improved reliability in the delivery process. This is due to the fact that deployment of a particular component, such as aligner 160, can be configured to begin in the upper area of the small intestine (e.g., the duodenum) allowing the capsule to be aligned within the intestine for optimal delivery of the drug (e.g., into the intestinal wall) as well as providing sufficient time for deployment/actuation of other components to achieve drug delivery into the intestinal wall while the capsule is still in the small intestine or other selected location.

As is discussed above, one or more portions of capsule 120 can be fabricated from various biocompatible polymers known in the art, including various biodegradable polymers which in a preferred embodiment can comprise cellulose, gelatin materials and PGLA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof.

In various embodiments, the wall 120*w* of the capsule is configured to be degradable by contact with liquids in the GI tract, for example liquids, in the small intestine. In preferred embodiments, the capsule wall is configured to remain intact during passage through the stomach, but then to be degraded in the small intestine. In one or more embodiments, this can be achieved by the use of an outer coating or layer 120*c* on the capsule wall 120*w*, which only degrades in the higher pH's found in the small intestine and serves to protect the underlying capsule wall from degradation within the stomach before the capsule reaches the small intestine (at which point the drug delivery process is initiated by degradation of the coating as is described herein). In use, such coatings allow for the targeted delivery of a therapeutic agent in a selected portion of the intestinal tract such as the small intestine including for example, into the wall of the small intestine.

Similar to capsule 20, in various embodiments, capsule 120 can include various radio-opaque, echogenic or other materials for location of the device using one or more medical imaging modalities known in the art such as fluoroscopy, ultrasound, MRI, etc. Such materials can be arranged in distinct bands or other shapes on the capsule so to readily provide visual indicators of the capsule in the intestinal tract using the one or more medical imaging modalities. They may also be configured to allow the physician to discern if the capsule has or has not deployed.

As is discussed further herein, in many embodiments, one or more of the deployment member 130, delivery member 172 or deployable aligner 160, may correspond to an expandable balloon that is shaped and sized to fit within capsule 120. Accordingly, for ease of discussion, deployment member 130, delivery member 172 and deployable aligner 160 will now be referred to as balloon 130, 160 and 172; however, it should be appreciated that other devices including various expandable devices are also contemplated for these elements and may include for example, various shape memory devices (e.g., an expandable basket made from shape memory biodegradable polymer spires), expandable piezo electric devices, and/or chemically expandable devices having an expanded shape and size corresponding to the interior volume 124*v* of the capsule 120.

One or more of balloons 130, 160 and 172 can comprise various polymers known in the medical device arts. In preferred embodiments such polymers can comprise one or more types of polyethylene (PE) which may correspond to low density PE (LDPE), linear low density PE (LLDPE), medium density PE (MDPE) and high density PE (HDPE) and other forms of polyethylene known in the art. In one more embodiments using polyethylene, the material may be cross-linked using polymer irradiation methods known in the art so. In particular embodiments radiation-based cross-linking may be used as to control the inflated diameter and shape of the balloon by decreasing the compliance of the balloon material. The amount or radiation may be selected to achieve a particular amount of cross linking to in turn produce a particular amount of compliance for a given balloon, e.g., increased irradiation can be used to produce stiffer less compliant balloon material. Other suitable polymers can include PET (polyethylene teraphalate), silicone and polyurethane. In various embodiments balloons 130, 160 and 172 may also include various radio-opaque materials known in the art such as barium sulfate to allow the physician to ascertain the position and physical state of the balloon (e.g., un-inflated, inflated or punctures. Balloons 130, 160 and 172 can be fabricated using various balloon blowing methods known in the balloon catheters arts (e.g., mold blowing, free blowing, etc.) to have a shape and size which corresponds approximately to the interior volume 124*v* of capsule 120. In various embodiments one or more of balloons 130, 160 and 172 and various connecting features (e.g., connecting tubes) can have a unitary construction being formed from a single mold. Embodiments employing such unitary construction provide the benefit of improved manufacturability and reliability since fewer joints must be made between one or more components of device 110.

Figure 13A:
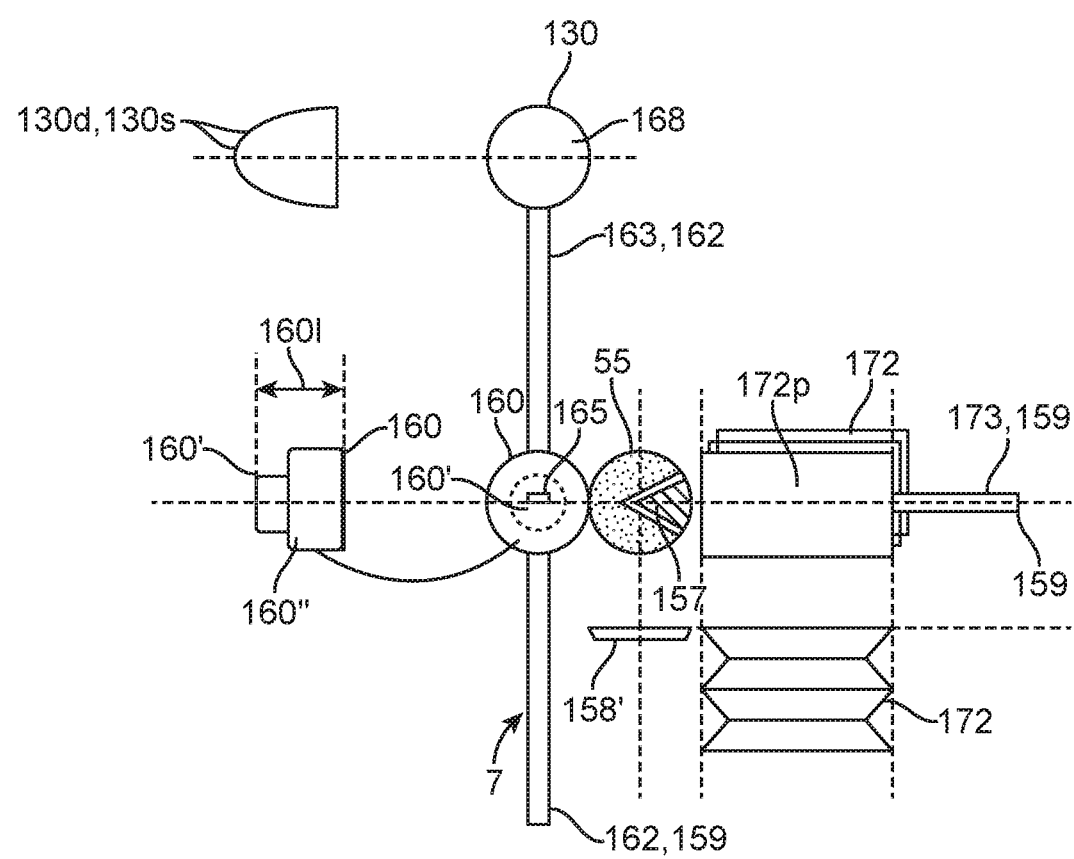
FIGS. 13a and 13b illustrate embodiments of unfolded multi balloon assemblies containing a deployment balloon, an aligner balloon, a delivery balloon and assorted connecting tubes.

Suitable shapes for balloons 130, 160 and 172 include various cylindrical shapes having tapered or curved end portions (an example of such a shape including a hot dog). In some embodiments, the inflated size (e.g., diameter) of one or more of balloons 130, 160 and 172, can be larger than capsule 120 so as to cause the capsule to come apart from the force of inflation, (e.g., due to hoop stress). In other related embodiments, the inflated size of one or more of balloons 130, 160 and 172 can be such that when inflated: i) the capsule 120 has sufficient contact with the walls of the small intestine so as to elicit a peristaltic contraction causing contraction of the small intestine around the capsule, and/or ii) the folds of the small intestine are effaced to allow. Both of these results allow for improved contact between the capsule/balloon surface and the intestinal wall so as deliver tissue penetrating members 40 over a selected area of the capsule and/or delivery balloon 172. Desirably, the walls of balloons 130, 160 and 172 will be thin and can have a wall thickness in the range of 0.005 to 0.0001" more preferably, in the range of 0.005 to 0.0001, with specific embodiments of 0.004, 0.003, 0.002, 0.001, and 0.0005). Additionally in various embodiments, one or more of balloon 130, 160 or 172 can have a nested balloon configuration having an inflation chamber 160IC and extended finger 160EF as is shown in the embodiments of FIG. 13c. The connecting tubing 163, connecting the inflation chamber 160IC can be narrow to only allow the passage of gas 168, while the connecting tubing 36 coupling the two halves of balloon 130 can be larger to allow the passage of water.

As indicated above, the aligner 160 will typically comprise an expandable balloon and for ease of discussion, will now be referred to as aligner balloon 160 or balloon 160. Balloon 160 can be fabricated using materials and methods described above. It has an unexpanded and expanded state (also referred to as a deployed state). In its expanded or deployed state, balloon 160 extends the length of capsule 120 such that forces exerted by the peristaltic contractions of the small intestine SI on capsule 120 serve to align the longitudinal axis 120LA of the capsule 120 in a parallel fashion with the longitudinal axis LAI of the small intestine SI. This in turn serves to align the shafts of tissue penetrating members 140 in a perpendicular fashion with the surface of the intestinal wall IW to enhance and optimize the penetration of tissue penetrating members 140 into the intestinal wall IW. In addition to serving to align capsule 120 in the small intestine, aligner 160 is also configured to push delivery mechanism 170 out of capsule 120 prior to inflation of delivery balloon 172 so that the delivery balloon and/or mechanism is not encumbered by the capsule. In use, this push out function of aligner 160 improves the reliability for delivery of the therapeutic agent since it is not necessary to wait for particular portions of the capsule (e.g., those overlying the delivery mechanism) to be degraded before drug delivery can occur.

Balloon 160 may be fluidically coupled to one or more components of device 110 including balloons 130 and 172 by means of polymer tube or other fluidic couplings 162 which may include a tube 163 for coupling balloons 160 and 130 and a tube 164 for coupling balloon 160 and balloon 172. Tube 163 is configured to allow balloon 160 to be expanded/inflated by pressure from balloon 130 (e.g., pressure generated the mixture of chemical reactants within balloon 130) and/or otherwise allow the passage of liquid between balloons 130 and 160 to initiate a gas generating chemical reaction for inflation of one or both of balloons 130 and 160. Tube 164 connects balloon 160 to 172 so as to allow for the inflation of balloon 172 by balloon 160. In many embodiments, tube 164 includes or is coupled to a control valve 155 which is configured to open at a selected pressure so as to control the inflation of balloon 172 by balloon 160. Tube 164 may thus comprise a proximal portion 164p connecting to the valve and a distal portion 164d leading from the valve. Typically, proximal and distal portions 164p and 164d will be connected to a valve housing 158 as is described below.

Valve 155 may comprise a triangular or other shaped section 156 of a material 157 which is placed within a the chamber 158c of a valve housing 158 (alternately, it may be placed directly within tubing 164). Section 157 is configured to mechanically degrade (e.g., tears, shears, delaminates, etc.) at a selected pressure so as to allow the passage of gas through tube 164 and/or valve chamber 158c. Suitable materials 157 for valve 155 can include bees wax or other form of wax and various adhesives known in the medical arts which have a selectable sealing force/burst pressure.

Figure 13B:
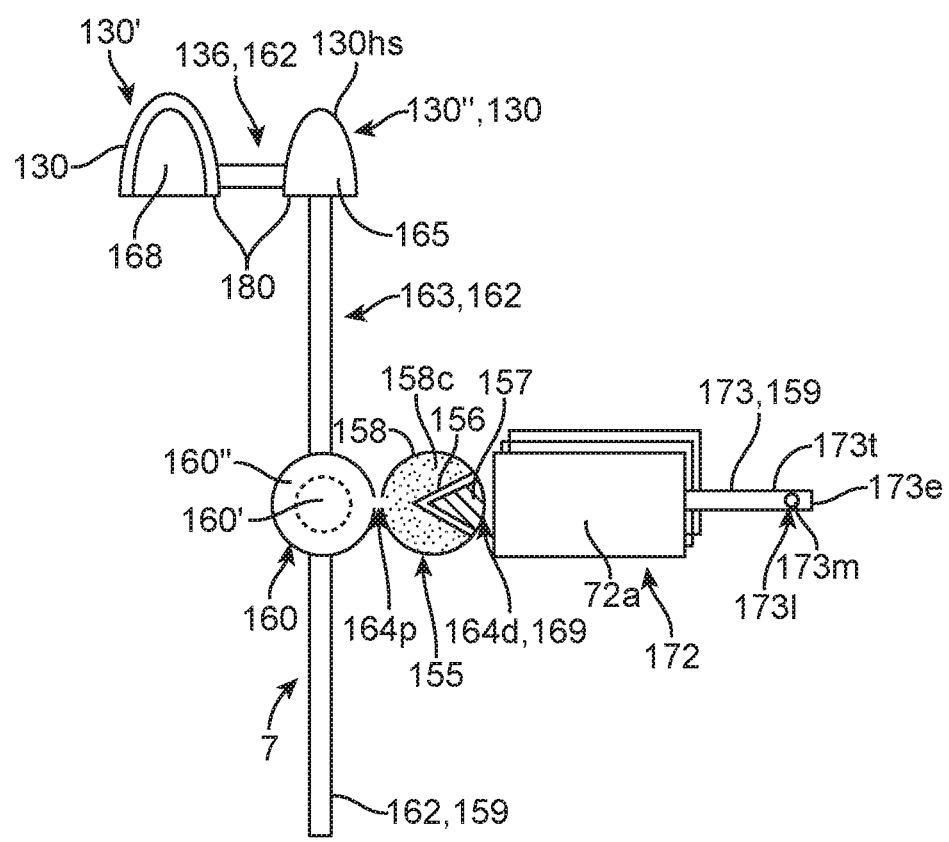
Figure 13C:
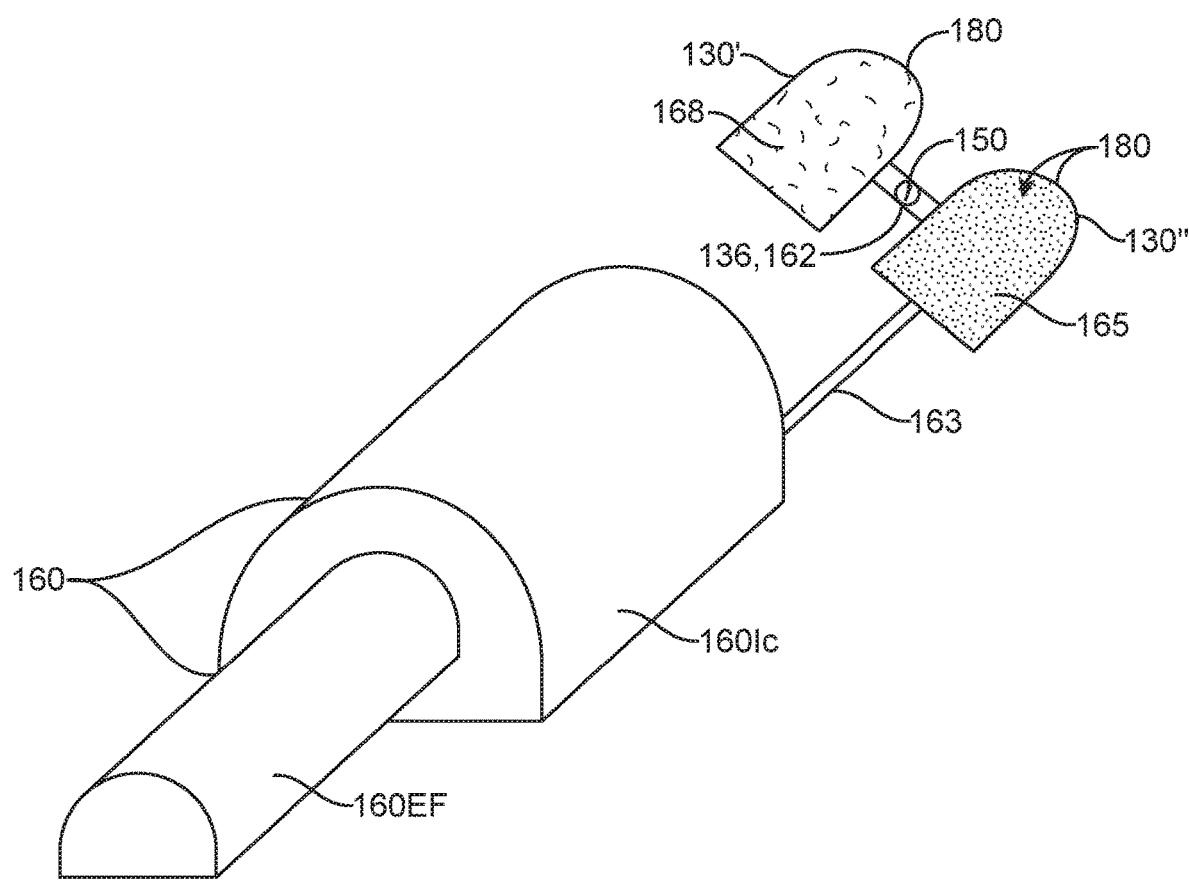
FIG. 13c is a perspective views illustrating embodiments of a nested balloon configuration which can be used for one or more embodiments of the balloons described herein including the aligner balloon.

Valve fitting 158 will typically comprise a thin cylindrical compartment (made from biodegradable materials) in which section 156 of material 157 is placed (as is shown in the embodiment of FIG. 13b) so as to seal the walls of chamber 158c together or otherwise obstruct passage of fluid through the chamber. The release pressure of valve 155 can be controlled through selection of one or more of the size and shape of section 156 as well as the selection of material 157 (e.g., for properties such as adhesive strength, shear strength etc.). In use, control valve 155 allows for a sequenced inflation of balloon 160 and 172 such that balloon 160 is fully or otherwise substantially inflated before balloon 172 is inflated. This, in turn, allows balloon 160 to push balloon 172 along with the rest of delivery mechanism 170 out of capsule 120 (typically from body portion 120p') before balloon 172 inflates so that deployment of tissue penetrating members 140 is not obstructed by capsule 120. In use, such an approach improves the reliability of the penetration of tissue penetrating members 140 into intestinal wall IW both in terms of achieving a desired penetration depth and delivering greater numbers of the penetrating members 140 contained in capsule 120 since the advancement of the members into intestinal wall IW is not obstructed by capsule wall 120w.

As is describe above, the inflated length 160l of the aligner balloon 160 is sufficient to have the capsule 120 become aligned with the lateral axis of the small intestine from peristaltic contractions of the intestine. Suitable inflated lengths 160l for aligner 160 can include a range between about ½ to two times the length 120l of the capsule 120 before inflation of aligner 160. Suitable shapes for aligner balloon 160 can include various elongated shapes such as a hotdog like shape. In specific embodiments, balloon 160 can include a first section 160' and a second section 160", where expansion of first section 160' is configured to advance delivery mechanism 170 out of capsule 120 (typically out of and second section 160" is used to inflate delivery balloon 172. In these and related embodiments, first and second sections 160' and 160" can be configured to have a telescope-style inflation where first section 160' inflates first to push mechanism 170 out of the capsule (typically from body portion 120p') and second section 160" inflates to inflate delivery member 172. This can be achieve by configuring first section 160' to have smaller diameter and volume than second section 160" such that first section 160' inflates first (because of its smaller volume) and with second section 160" not inflating until first section 60' has substantially inflated. In one embodiment, this can be facilitated by use of a control valve 155 (described above) connecting sections 160' and 160" which does not allow passage of gas into section 160" until a minimum pressure has been reached in section 160'. In some embodiments, the aligner balloon can contain the chemical reactants which react upon mixture with water or other liquid from the deploying balloon.

In many embodiments, the deployment member 130 will comprise an expandable balloon, known as the deployment balloon 130. In various embodiments, deployment balloon 30 is configured to facilitate deployment/expansion of aligner balloon 160 by use of a gas, for example, generation of a gas 169 from a chemical. The gas may be generated by the reaction of solid chemical reactants 165, such as an acid 166 (e.g., citric acid) and a base 166 (e.g., potassium bicarbonate, sodium bicarbonate and the like) which are then mixed with water or other aqueous liquid 168. The amount of reactants can be chosen using stoichiometric methods to produce a selected pressure in one or more of balloons 130, 160 and 72. The reactants 165 and liquids can be stored separately in balloon 130 and 160 and then brought together in response to a trigger event, such as the pH conditions in the small intestine. The reactants 165 and liquids 168 can be stored in either balloon, however in preferred embodiments, liquid 168 is stored in balloon 130 and reactants 165 in balloon 160. To allow for passage of the liquid 168 to start the reaction and/or the resulting gas 169, balloon 130 may be coupled to aligner balloon 160 by means of a connector tube 163 which also typically includes a separation means 150 such as a degradable valve 150 described below. For embodiments where balloon 130 contains the liquid, tube 163 has sufficient diameter to allow for the passage of sufficient water from balloon 130 to balloon 60 to produce the desired amount of gas to inflate balloon 160 as well inflate balloon 172. Also when balloon 130 contains the liquid, one or both of balloon 30 and tube 63 are configured to allow for the passage of liquid to balloon 160 by one or more of the following: i) the compressive forced applied to balloon 130 by peristaltic contractions of the small intestine on the exposed balloon 130; and ii) wicking of liquid through tube 163 by capillary action.

Tube 163 will typically include a degradable separation valve or other separation means 150 which separates the contents of balloon 130, (e.g., water 158) from those of balloon 160 (e.g., reactants 165) until the valve degrades. Valve 150 can be fabricated from a material such as maltose, which is degradable by liquid water so that the valve opens upon exposure to water along with the various liquids in the digestive tract. It may also be made from materials that are degradable responsive to the higher pH's found in the intestinal fluids such as methacrylate based coatings. The valve is desirably positioned at location on tube 163 which protrudes above balloon 130 and/or is otherwise sufficient exposed such that when cap 120$p'$ degrades the valve 150 is exposed to the intestinal liquids which enter the capsule. In various embodiments, valve 150 can be positioned to lie on the surface of balloon 130 or even protrude above it (as is shown in the embodiments of FIGS. 16$a$ and 16$b$), so that is has clear exposure to intestinal fluids once cap 120$p'$ degrades. Various embodiments of the invention provide a number of structures for a separation valve 150, for example, a beam like structure (where the valve comprises a beam that presses down on tube 163 and/or connecting section 136), or collar type structure (where the valve comprise a collar lying over tube 163 and/or connecting section 136). Still other valve structures are also contemplated.

Balloon 130 (or other expandable deployment device 130) has a deployed and a non-deployed state. In the deployed state, the deployment balloon 130 can have a dome shape 130$d$ which corresponds to the shape of an end of the capsule. Other shapes 130$s$ for the deployed balloon 130 are also contemplated, such as spherical, tube-shape, etc. The reactants 165 will typically include at least two reactants 166 and 167, for example, an acid such as citric acid and a base such as sodium bicarbonate. Other reactants 165 including other acids, e.g., acetic acid and bases, e.g., sodium hydroxide are also contemplated. When the valve or other separation means 150 opens, the reactants mix in the liquid and produce a gas such as carbon dioxide which expands the aligner balloon 160 or other expandable member.

In an alternative embodiment shown in FIG. 13$b$, the deployment balloon 130 can actually comprise a first and second balloon 130' and 130" connected by a tube 36 or other connection means 136 (e.g., a connecting section). Connecting tube 136 will typically include a separation valve 150 that is degradable by a liquid as described above and/or a liquid having a particular pH such as basic pH found in the small intestine (e.g., 5.5 or 6.5). The two balloons 130' and 130" can each have a half dome shape 130$hs$ allowing them to fit into the end portion of the capsule when in the expanded state. One balloon can contain the chemical reactant(s) 165 (e.g., sodium bicarbonate, citric acid, etc.) the other the liquid water 168, so that when the valve is degraded the two components mix to form a gas which inflates one or both balloons 130' and 130" and in turn, the aligner balloon 160.

Figure 14A:
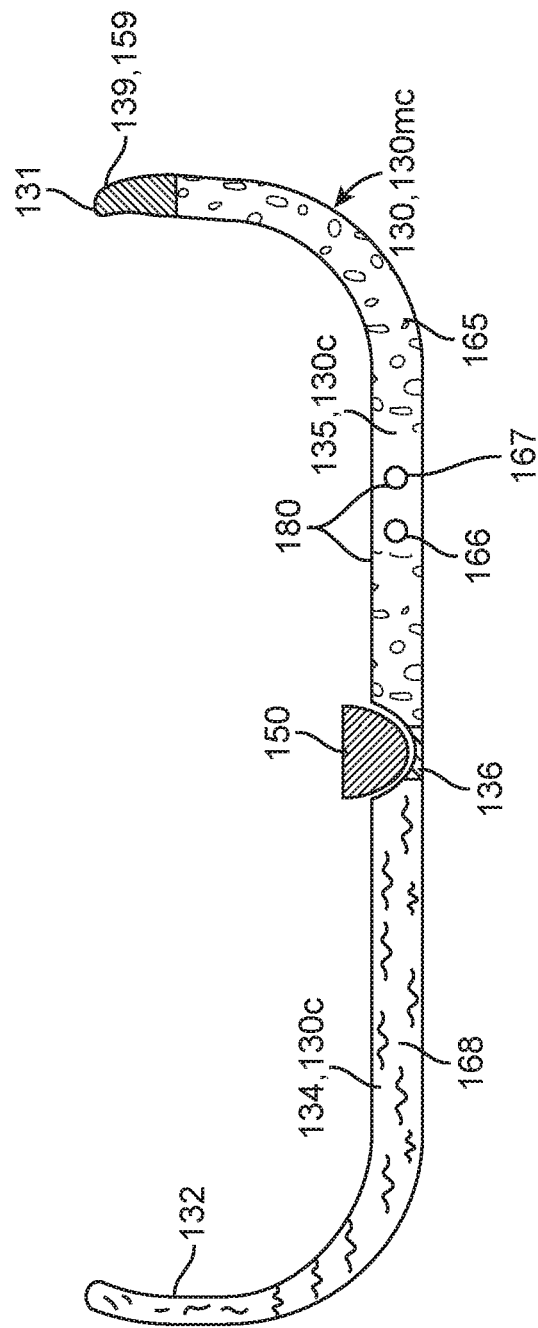
FIGS. 14a-14c are lateral views illustrating embodiments of a multi compartment deployment balloon.
Figure 14B:
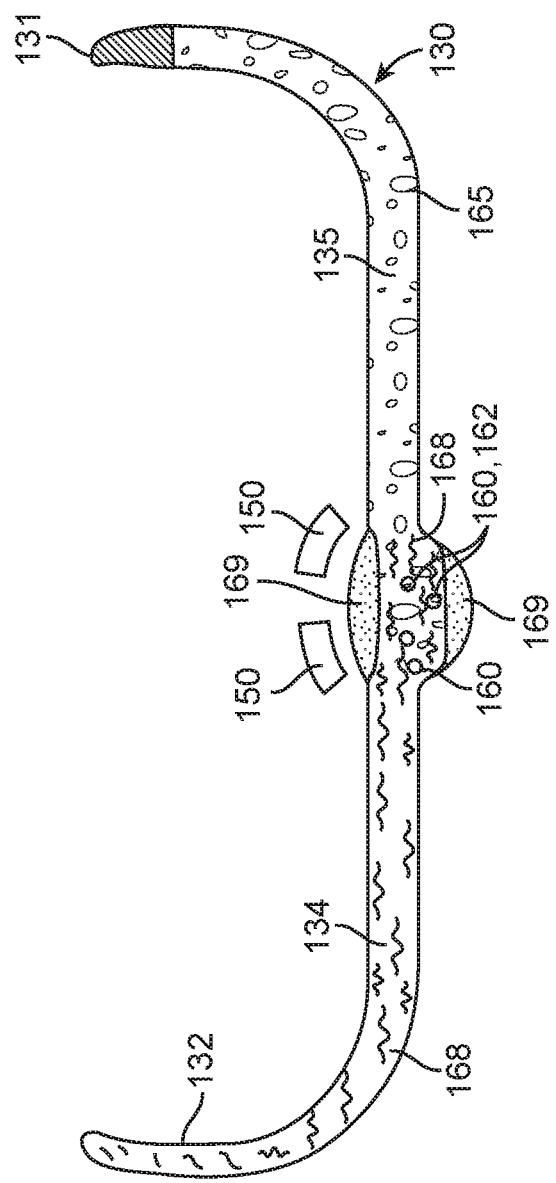
Figure 14C:
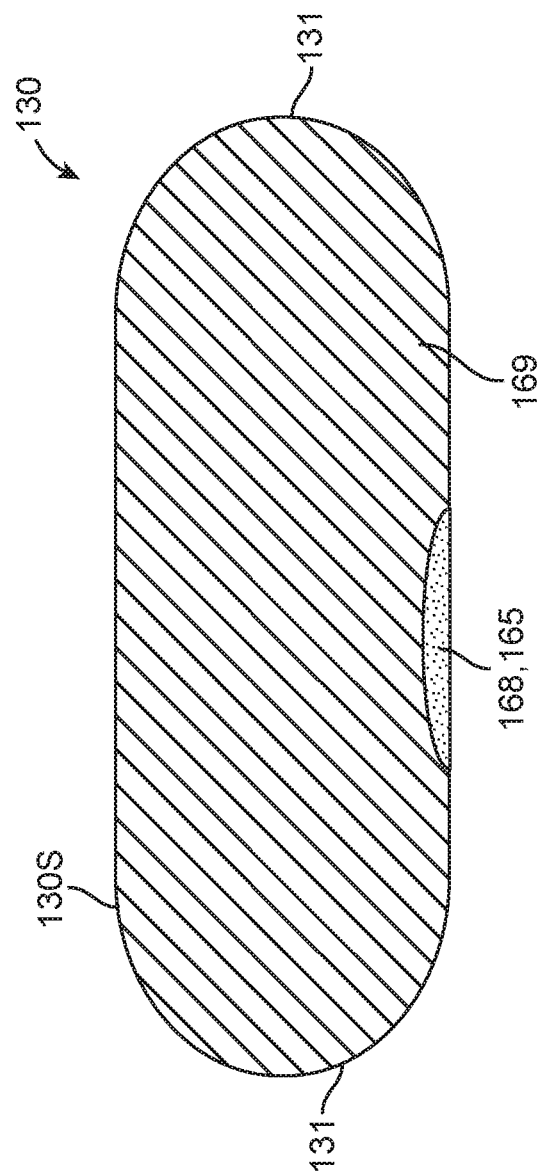

In yet another alternative embodiment, balloon 130 can comprise a multi-compartment balloon 130$mc$, that is formed or other constructed to have multiple compartments 130$c$. Typically, compartments 130$c$ will include at least a first and a second compartment 134 and 135 which are separated by a separation valve 150 or other separation means 150 as is shown in the embodiment of FIG. 14$a$. In many embodiments, compartments 134 and 135 will have at least a small connecting section 136 between them which is where separation valve 150 will typically be placed. A liquid 168, typically water, can be disposed within first compartment 134 and one or more reactants 165 disposed in second compartment 135 (which typically are solid though liquid may also be used) as is shown in the embodiment of FIG. 14$a$. When valve 150 opens (e.g., from degradation caused by fluids within the small intestine) liquid 168 enters compartment 135 (or vice versa or both), the reactant(s) 165 mix with the liquid and produce a gas 169 such as carbon dioxide which expands balloon 130 which in turn can be used to expand one or more of balloons 160 and 172.

Reactants 165 will typically include at least a first and a second reactant, 166 and 167 for example, an acid such as citric acid and a base such as sodium bi-carbonate or potassium bi-carbonate. As discussed herein, in various embodiments they may be placed in one or more of balloon 130 (including compartments 134 and 135 or halves 130' and 130") and balloon 160. Additional reactants, including other combinations of acids and bases which produce an inert gas by product are also contemplated. For embodiments using citric acid and sodium or potassium bicarbonate, the ratios between the two reactants (e.g., citric acid to potassium bicarbonate) can be in the range of about 1:1 to about 1:4, with a specific ratio of about 1:3. Desirably, solid reactants 165 have little or no absorbed water. Accordingly, one or more of the reactants, such as sodium bicarbonate or potassium bicarbonate can be pre-dried (e.g., by vacuum drying) before being placed within balloon 130. Other reactants 165 including other acids, e.g., acetic acid and bases are also contemplated. The amounts of particular reactants 165, including combinations of reactants can be selected to produce particular pressures using known stoichiometric equations for the particular chemical reactions as well as the inflated volume of the balloon and the ideal gas law (e.g., $PV=nRT$). In particular embodiments, the amounts of reactants can be selected to produce a pressure selected one or more of balloons 130, 160 and 172 to: i) achieve a particular penetration depth into the intestinal wall; and produce a particular diameter for one or more of balloons 130, 160 and 172; and iii) exert a selected amount of force against intestinal wall IW. In particular embodiments, the amount and ratios of the reactants (e.g., citric acid and potassium bicarbonate) can be selected to achieve pressures in one more of the balloons 130, 160 and 172 in the range of 10 to 15 psi, with smaller and larger pressures contemplated. Again the amounts and ratios of the reactants to achieve these pressures can be determined using known stoichiometric equations.

In various embodiments of the invention using chemical reactants 165 to generate gas 169, the chemical reactants alone or in combination with the deployment balloon 130 can comprise a deployment engine for 180 deploying one or both of the aligner balloon 160 and delivery mechanism 170 including delivery balloon 172. Deployment engine 180 may also include embodiments using two deployment balloons 130 and 130" (a dual dome configuration as shown in FIG. 13b), or a multi compartment balloon 130mc as shown in FIG. 14a. Other forms of a deployment engine 180 are also contemplated by various embodiments of the invention such as use of expandable piezo-electric materials (that expand by application of a voltage), springs and other shape memory materials and various thermally expandable materials.

One or more of the expandable balloons 130, 160 and 172 will also typically include a deflation valve 159 which serves to deflate the balloon after inflation. Deflation valve 159 can comprise biodegradable materials which are configured to degrade upon exposure to the fluids in the small intestine and/or liquid in one of the compartments of the balloon so as to create an opening or channel for escape of gas within a particular balloon. Desirably, deflation valves 159 are configured to degrade at a slower rate than valve 150 to allow sufficient time for inflation of balloons, 130, 160 and 172 before the deflation valve degrades. In various embodiments, of a compartmentalized balloon 130, deflation valve 159 can correspond to a degradable section 139 positioned on an end portion 131 of the balloon as is shown in the embodiment of FIG. 14a. In this and related embodiments, when degradable section 139 degrades from exposure to the liquid, balloon wall 132 tears or otherwise comes apart providing for a high assurance of rapid deflation. Multiple degradable sections 139 can be placed at various locations within balloon wall 132.

In various embodiments of balloon 172, deflation valve 159 can correspond to a tube valve 173 attached to the end 172e of the delivery balloon 172 (opposite to the end which is coupled to the aligner balloon) as is shown in the embodiment of FIG. 13b. The tube valve 173 comprises a hollow tube 173t having a lumen that is obstructed at a selected location 173l with a material 173m such as maltose that degrades upon exposure to fluid such as the fluid in the small intestine. The location 173l of the obstructing material 173m in tube 173t is selected to provide sufficient time for the delivery balloon 172 to inflate and deliver the tissue penetrating members 40 into the intestinal wall IW before the obstructing material dissolves to open valve 173. Typically, this will be close to the end 173e of the tube 173t, but not quite so as to allow time for liquid to have to wick into the tube lumen before it reaches material 173m. According to one or more embodiments, once the deflation valve 173 opens, it not only serves to deflate the delivery balloon 172 but also the aligner balloon 160 and deployment balloon 130 since in many embodiments, all three are fluidicially connected (aligner balloon being fluidically connected to delivery balloon 172 and the deployment balloon 130 being fluidically connected to aligner balloon 160). Opening of the deflation valve 173 can be facilitated by placing it on the end 172e of the delivery balloon 172 that is forced out of capsule 120 by inflation of the aligner balloon 160 so that the deflation valve has good exposure to liquids in the small intestine. Similar tube deflation valves 173 can also be positioned on one or both of aligner balloon 162 and the deployment balloon 130. In these later two cases, the obstructing material in the tube valve can be configured to degrade over a time period to allow sufficient time for inflation of delivery balloon 172 and advancement of tissue penetrating members 140 into the intestinal wall.

Additionally, as further backup for insured deflation, one or more puncture elements 182 can be attached to the inside surface 124 of the capsule such that when a balloon (e.g., balloon 130, 160, 172) fully inflates it contacts and is punctured by the puncture element 182. Puncture elements 182 can comprise short protrusions from surface 124 having a pointed tip. In another alternative or additional embodiment of means for balloon deflation, one or more of the tissue penetrating members 140 can be directly coupled to the wall of 172w of balloon 172 and configured to tear away from the balloon when they detach, tearing the balloon wall in the process.

Figure 18A:
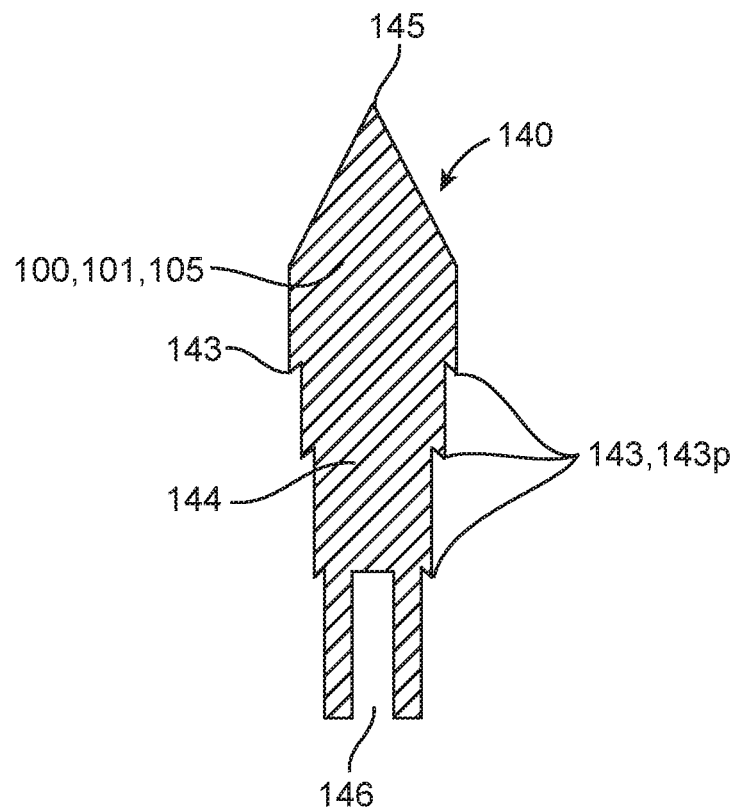
FIG. 18a is a side view of an embodiment of the tissue penetrating member.
Figure 18B:
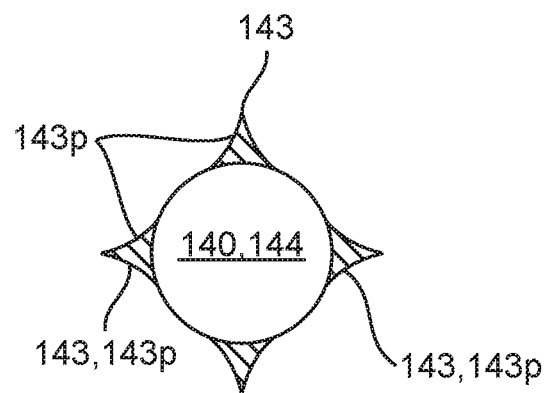
FIG. 18b is a bottom view of an embodiment of the tissue penetrating member illustrating placement of the tissue retaining features.
Figure 18C:
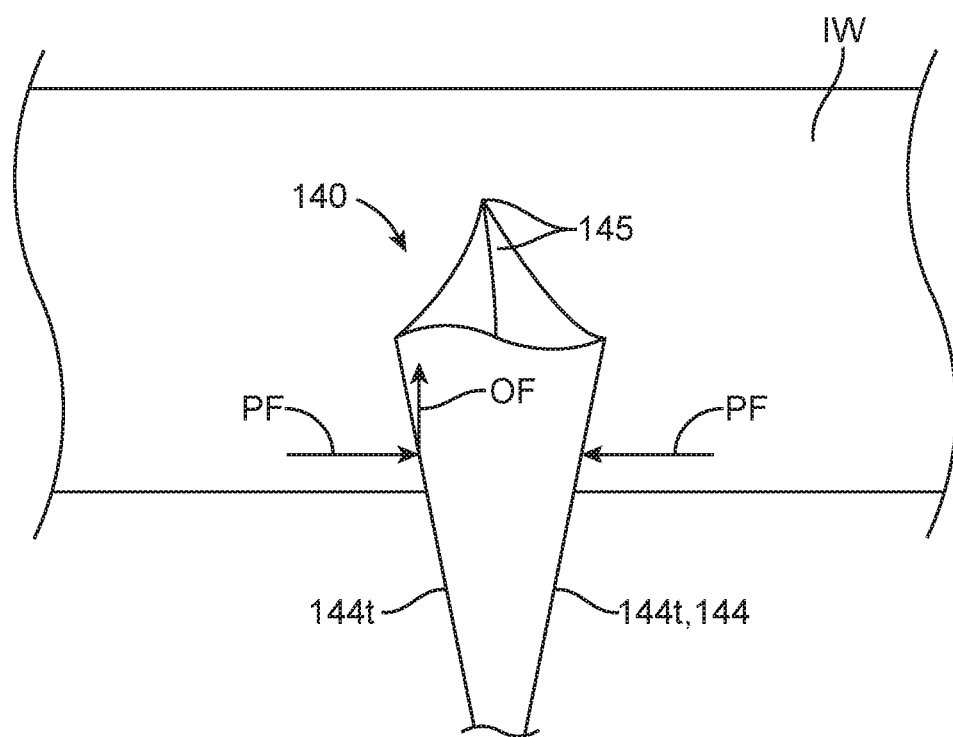
FIG. 18c is a side view of an embodiment of the tissue penetrating member having a trocar tip and inverted tapered shaft.

A discussion will now be presented of tissue penetrating members 140. Tissue penetrating member 140 can be fabricated from various drugs and other therapeutic agents 101, one or more pharmaceutical excipients (e.g., disintegrants, stabilizers, etc.) and one or more biodegradable polymers. The later materials chosen to confer desired structural and material properties to the penetrating member (for example, column strength for insertion into the intestinal wall, or porosity and hydrophilicity for control the release of drug). Referring now to FIGS. 18a-18f, in many embodiments, the penetrating member 140 can be formed to have a shaft 144 and a needle tip 145 or other pointed tip 145 so as to readily penetrate tissue of the intestinal wall as shown in the embodiment of FIG. 18a. In preferred embodiments, tip 145 has a trocar shape as is shown in the embodiment of FIG. 18c. Tip 145 may comprise various degradable materials (within the body of the tip or as a coating), such as sucrose or other sugar which increase the hardness and tissue penetrating properties of the tip. Once placed in the intestinal wall, the penetrating member 140 is degraded by the interstitial fluids within the wall tissue so that the drug or other therapeutic agent 101 dissolves in those fluids and is absorbed into the blood stream. One or more of the size, shape and chemical composition of tissue penetrating member 140 can be selected to allow for dissolution and absorption of drug 101 in a matter of seconds, minutes or even hours. Rates of dissolution can be controlled through the use of various disintegrants known in the pharmaceutical arts. Examples of disintegrants include, but are not limited to, various starches such as sodium starch glycolate and various cross linked polymers such as carboxymethyl cellulose. The choice of disintegrants can be specifically adjusted for the environment within the wall of the small intestine and/or peritoneal wall.

Tissue penetrating member 140 will also typically include one or more tissue retaining features 143 such as a barb or hook to retain the penetrating member within the tissue of the intestinal wall IW after advancement. Retaining features 143 can be arranged in various patterns 143p to enhance tissue retention such as two or more barbs symmetrically or otherwise distributed around and along member shaft 144 as is shown in the embodiments of FIGS. 18a and 18b. Additionally, in many embodiments, penetrating member will also include a recess or other mating feature 146 for attachment to a coupling component on delivery mechanism 170.

Tissue penetrating member 140 is desirably configured to be detachably coupled to platform 175 (or other component of delivery mechanism 170), so that after advancement of the tissue penetrating member 140 into the intestinal wall, the penetrating member detaches from the balloon. Detachability can be implemented by a variety of means including: i) the snugness or fit between the opening 174 in platform 175 and the member shaft 144); ii) the configuration and placement of tissue retaining features 143 on penetrating member 140; and iii) the depth of penetration of shaft 144 into the intestinal wall. Using one or more of these factors, penetrating member 140 be configured to detach as a result of balloon deflation (where the retaining features 143 hold the penetrating member 140 in tissue as the balloon deflates or otherwise pulls back away from the intestinal wall) and/or the forces exerted on capsule 120 by a peristaltic contraction of the small intestine.

In a specific embodiment, the detachability and retention of tissue penetrating member 140 in the intestinal wall IW can be enhanced by configuring the tissue penetrating member shaft 144 to have an inverse taper 144t as is shown in the embodiment of FIG. 18c. The taper 144t on the shaft 144 is configured such that the application of peristaltic contractile forces from the intestinal wall on the shaft result in the shaft being forced inward (e.g., squeezed inward). This is due to the conversion by shaft taper 144t of the laterally applied peristaltic force PF to an orthogonal force OF acting to force the shaft inward into the intestinal wall. In use, such inverse tapered shaft configurations serve to retain tissue penetrating member 140 within the intestinal wall so as to detach from platform 175 (or other component of delivery mechanism 170) upon deflation of balloon 172. In additional embodiments, tissue penetrating members 140 having an inverse tapered shaft may also include one or more retaining features 143 to further enhance the retention of the tissue penetrating member within intestinal wall IW once inserted.

As described above, in various embodiments, tissue penetrating member 140 can be fabricated from a number of drugs and other therapeutic agents 101. Also according to one or more embodiments, the tissue penetrating member may be fabricated entirely from drug 101 (e.g. such as an AP-antibody) or may have other constituent components as well, e.g., various pharmaceutical excipients (e.g., binders, preservatives, disintegrants, etc.), polymers conferring desired mechanical properties, etc. Further, in various embodiments one or more tissue penetrating members 140 can carry the same or a different drug 101 (or other therapeutic agent) from other tissue penetrating members. The former configuration allows for the delivery of greater amounts of a particular drug 101 (e.g., a particular AP antibody), while the later, allows two or more different drugs to be delivered into the intestinal wall at about the same time to facilitate drug treatment regimens requiring substantial concurrent delivery of multiple drugs. In embodiments of device 110, having multiple delivery assemblies 178 (e.g., two, one on each face of balloon 172), a first assembly 178' can carry tissue penetrating members having a first drug 101 and a second assembly 178" can carry tissue penetrating members having a second drug 101.

Figure 18D:
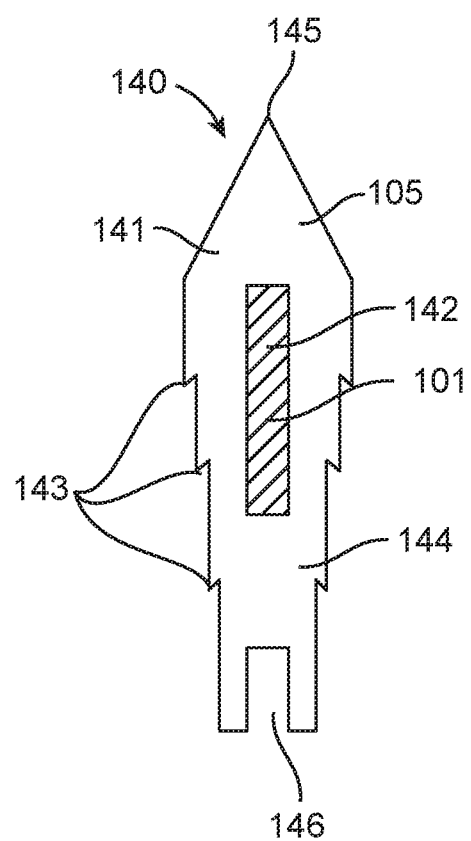
FIG. 18d is a side view of an embodiment of the tissue penetrating member having a separate drug containing section.
Figures 18E, 18F:
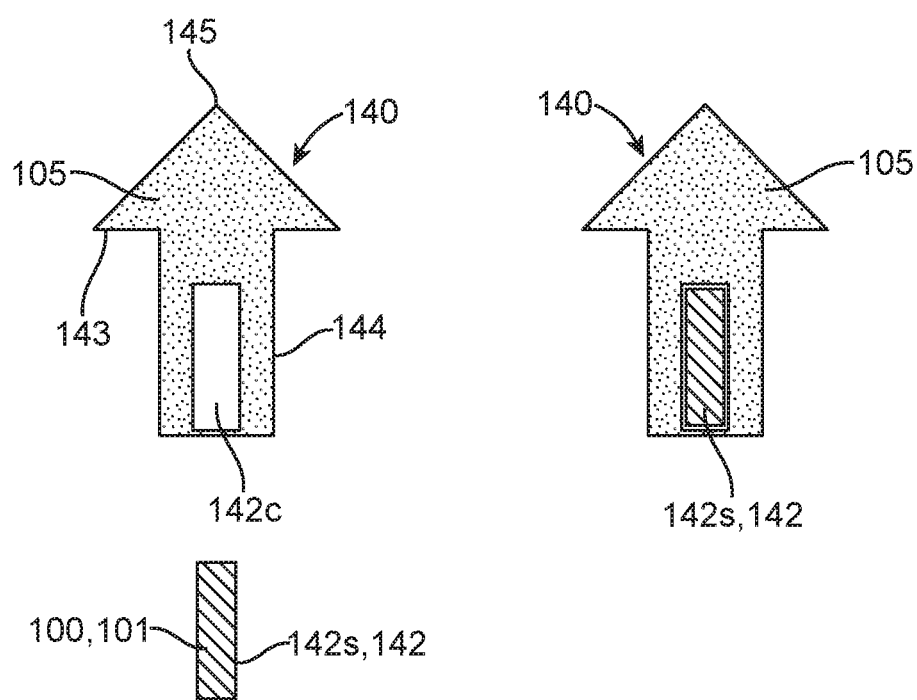
FIGS. 18e and 18f are side views showing assembly of an embodiment of a tissue penetrating member having a shaped drug containing section.

Typically, the drug or other therapeutic agent 101 carried by the tissue penetrating member 140 will be mixed in with a biodegradable material 105 to form tissue penetrating member 140. Material 105 may include one or more biodegradable polymers such as PGLA, cellulose, as well as sugars such as maltose or other biodegradable material described herein or known in the art. In such embodiments, the penetrating member 140 may comprise a substantially heterogeneous mixture of drug 101 and biodegradable material 105. Alternatively, the tissue penetrating member 140 may include a portion 141 formed substantially from biodegradable material 105 and a separate section 142 that is formed from or contains drug 101 as shown in the embodiment of FIG. 18d. In one or more embodiments, section 142 may correspond to a pellet, slug, cylinder or other shaped section 142s of drug 101. Shaped section 142s may be pre-formed as a separate section which is then inserted into a cavity 142c in tissue penetrating member 140 as is shown in the embodiments of FIGS. 18e and 18f. Alternatively section 142s may be formed by adding of drug preparation 100 to cavity 142c. In embodiments, where drug preparation 100 is added to cavity 142c, preparation may be added in as a powder, liquid, or gel which is poured or injected into cavity 142c. Shaped section 142s may be formed of drug 101 by itself or a drug preparation containing drug 101 and one or more binders, preservatives, disintegrants and other excipients. Suitable binders include polyethylene glycol (PEG) and other binders known in the art. In various embodiments, the PEG or other binder may comprise in the range of about 10 to 90% weight percent of the section 142s, with a preferred embodiment for insulin preparations of about 25-90 weight percent. Other excipients which may be used for binders in tissue penetrating member 140 may include for example, PLA, PLGA, Cyclodextrin, Cellulose, Methyl Cellulose, maltose, Dextrin, Sucrose and PGA. Further information on the weight percent of excipients in section 142 may be found in Table 3. For ease of discussion, section 142 is referred to as a pellet in the table, but the data in the table are also applicable to other embodiments of section 142 described herein.

In various embodiments, the weight of tissue penetrating member 140 can range between about 10 to 15 mg, with larger and smaller weights contemplated. For embodiments of tissue penetrating member 140 fabricated from maltose, the weight can range from about 11 to 14 mg. In various embodiments, depending upon the drug 101 and the desired delivered dose, the weight percent of drug in member 140 can range from about 0.1 to about 15%. In exemplary embodiments, these weight percents correspond to embodiments of members 140 fabricated from maltose or PGLA, however they are also applicable to any of the biodegradable materials 105 used in the fabrication of members 140, for example polyethylene and other like materials. The weight percent of drug or other therapeutic agent 101 in member 140 can be adjusted depending upon the desired dose as well as to provide for structural and stoichiometric stability of the drug and also to achieve a desired concentration profile of the drug in the blood or other tissue of the body. Various stability tests and models (e.g., using the Arrhenius equation) known in the art and/or known rates of drug chemical degradation may be used to make specific adjustments in the weight percent range. Table 3 lists the dose and weight percent range for insulin and number of other drugs which may be delivered by tissue penetrating member 140. In some cases, the table lists ranges as well a single value for the dose. It should be appreciated that these values are exemplary and other values recited herein including those in claims are also considered. Further, embodiments of the invention also consider variations around these values including for example, ±1, ±5, ±10, ±25, and even larger variations. Such variations are considered to fall within the scope of an embodiment claiming a particular value or range of values. The table also lists the weight percentage of drug in section 142 for various drugs and other therapeutic agents, where again for ease of discussion, section 142 is referred to as a pellet. Again, embodiments of the invention consider the variations described above.

TABLE 3

| Drug | Dose Via Capsule** | % Weight of Drug in the needle | % Weight of drug in pellet |
|---|---|---|---|
| Insulin | 4-9 units, 5-30 units, 1-50 units | 2-15% | 10-75% |
| Exenatide | 1-10 ug, 1-20 ug, 10 ug | <1%, 0.1-1% | 0.2-1% |
| Liraglutide | 0.1-1 mg, 0.5-2 mg, 0.6 mg | 3-6% | 25-40% |
| Pramlintide | 15-120 ug | 0.1-1% | 0.5-6% |
| Growth Hormone | 0.2-1 mg, 0.1-4 mg | 2-10% | 10-50% |
| Somatostatin and Analogs | 50-600 ug, 10-100 ug | 0.3-8% | 2-35% |
| GnRH and Analogs | 0.3-1.5 mg, 0.1-2 mg | 2-15% | 15-75% |
| Vasopressin | 2-10 units | <1%, 0.1-1% | 0.2-1% |
| PTH and Analogues | 0.1 to 10 ug, 10-30 ug, 20 ug | 1-2% | 0.5-2% |
| Interferons and analogs | | | |
| 1. For Multiple Sclerosis | 0.03-0.25 mg | 0.1-3% | 1.5-15% |
| 2. For Hep B and HepC | 6-20 ug | 0.05-0.2% | 0.2-1% |
| Adalimumab | 1-5 mg, 2-4 mg | 8-12% | 70-90% |
| Infliximab | 1-10, 5 mg | 8-12% | 70-90% |
| Etanercept | 1-5 mg, 3 mg | 8-12% | 70-90% |
| Natalizumab | 1-5 mg, 3 mg | 8-12% | 70-90% |

Tissue penetrating member 140 can be fabricated using one or more polymer and pharmaceutical fabrication techniques known in the art. For example, drug 101 (with or without biodegradable material 105) can be in solid form and then formed into the shape of the tissue penetrating member 140 using molding, compaction or other like method with one or more binding agents added. Alternatively, drug 101 and/or drug preparation 100 may be in solid or liquid form and then added to the biodegradable material 105 in liquid form with the mixture then formed into the penetrating member 140 using molding or other forming method known in the polymer arts. In some embodiments, the tissue penetrating member may have an outer layer or coating which has a slower rate of degradation in the intestinal wall (or surrounding tissue) then the inner body of the tissue penetrating so as to slow the rate of drug release into the blood stream. In various embodiments, the outer coating or layer may have a rate of biodegradation that is 10, 25, 50, 100, 200, 500, or a 1000% slower than that of the inner core. In use, such embodiments allow for a delayed release of the drug 101.

Desirably, embodiments of the tissue penetrating member 140 comprising a drug or other therapeutic agent 101 and degradable material 105 are formed at temperatures which do not produce any substantial thermal degradation of drug including drugs such as various peptides and proteins. This can be achieved through the use of room-temperature curing polymers and room temperature molding and solvent evaporation techniques known in the art. In particular embodiments, the amount of thermally degraded drug or other therapeutic agent within the tissue penetrating member is desirably less than about 10% by weight and more preferably, less than 5% and still more preferably less than 1%. The thermal degradation temperature(s) for a particular drug are either known or can be determined using methods known in the art and then this temperature can be used to select and adjust the particular polymer processing methods (e.g., molding, curing, solvent evaporation methods etc.) to minimize the temperatures and associated level of drug thermal degradation.

Figures 16A, 16B:
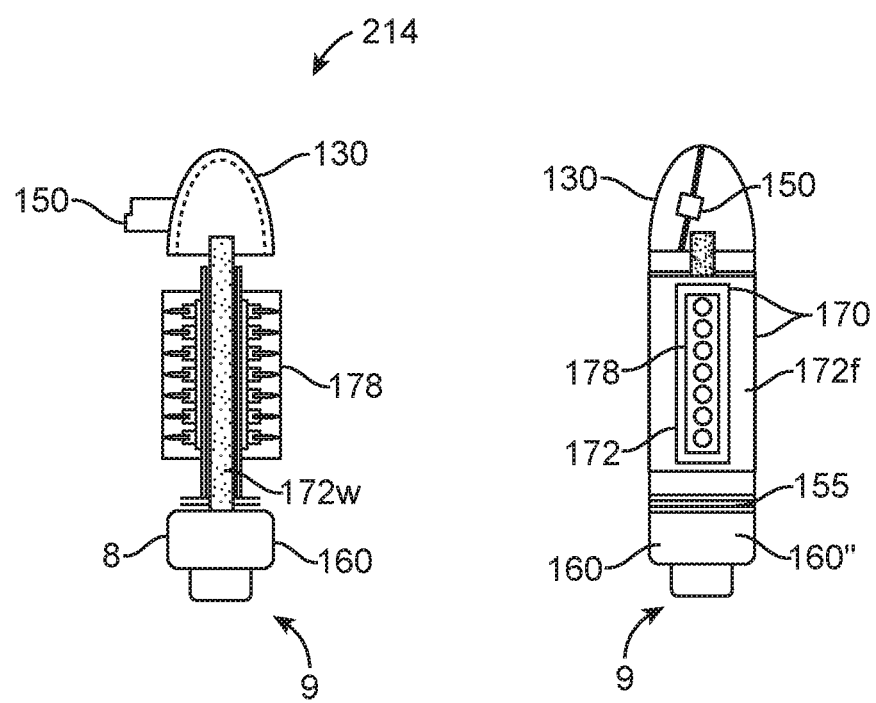
FIGS. 16a and 16b are orthogonal views illustrating embodiments of the final folded multi balloon assembly with the attached delivery assembly.
Figure 17A:
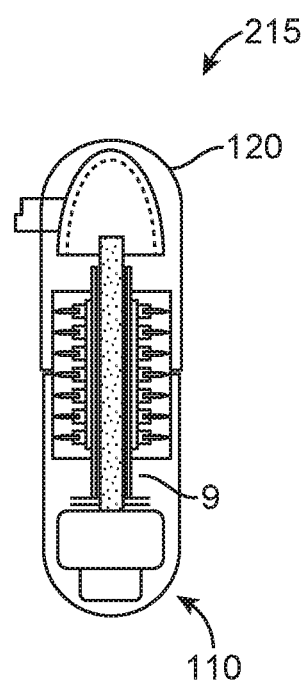
FIGS. 17a and 17b are orthogonal transparent views illustrating embodiments of the final folded multi balloon assembly inserted into the capsule.
Figure 17B:
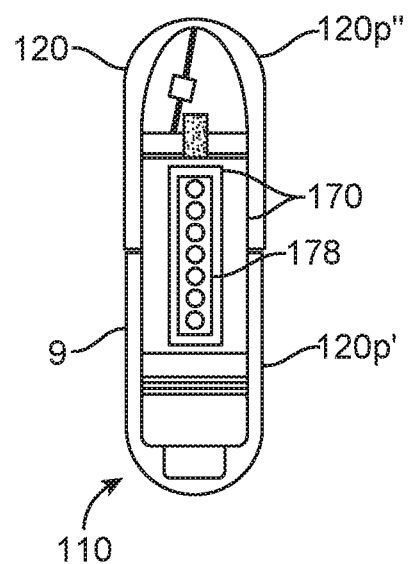

A description will be provided of delivery mechanism 170. Typically, the mechanism will comprise a delivery assembly 178 (containing tissue penetrating members 140) that is attached to delivery balloon 172 as is shown in the embodiment of FIGS. 16a and 16b. Inflation of the delivery balloon provides a mechanical force for engaging delivery assembly 172 outwards from the capsule and into the intestinal wall IW so as to insert tissue penetrating members 140 into the wall. In various embodiments, the delivery balloon 172 can have an elongated shape with two relatively flat faces 172f connected by an articulated accordion-like body 172b. The flat faces 172f can be configured to press against the intestinal wall (IW) upon expansion of the balloon 172 so as to insert the tissue penetrating members (TPMs) 140 into the intestinal wall. TPMs 140 (either by themselves or as part of a delivery assembly 178 described below) can be positioned on one or both faces 172f of balloon 172 to allow insertion of drug containing TPMs 40 on opposite sides of the intestinal wall. The faces 172f of balloon 172 may have sufficient surface area to allow for placement of a number of drug containing TPMs 140 on each face.

Figure 19:
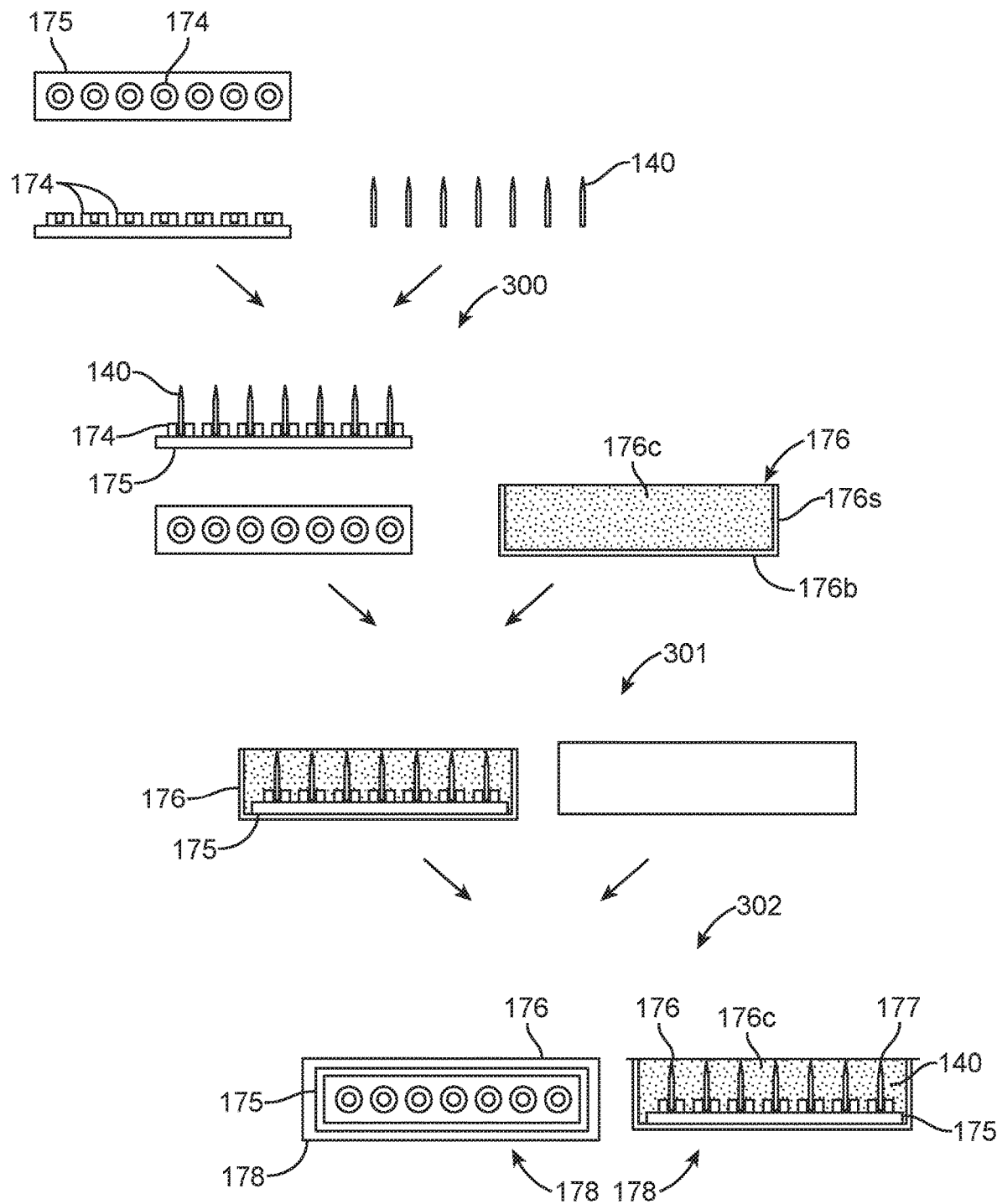
FIG. 19 provides assorted views of the components and steps used to assemble an embodiment of the delivery assembly.

Referring now to FIG. 19, a description will now be provided of the assembly of delivery assembly 178. In a first step 300, one or more tissue penetrating members 140 can be detachably coupled to a biodegradable advancement structure 175 which may correspond to a support platform 175 (also known as platform 175). In preferred embodiments, platform 175 includes one or more openings 174 for insertion of members 140 as shown in step 300. Openings 174 are sized to allow for insertion and retention of members 140 in platform 175 prior to expansion of balloon 172 while allowing for their detachment from the platform upon their penetration into the intestinal wall. Support platform 175 can then be positioned within a carrying structure 176 as shown in step 301. Carrying structure 176 may correspond to a well structure 176 having side walls 176s and a bottom wall 176b which define a cavity or opening 176c. Platform 175 is desirably attached to inside surface of bottom wall 176b using adhesive or other joining methods known in the art. Well structure 176 can comprise various polymer materials and may be formed using vacuum forming techniques known in the polymer processing arts. In many embodiments, opening 176o can be covered with a protective film 177 as shown in step 302. Protective film 177 has properties selected to function as a barrier to protect tissue penetrating members 140 from humidity and oxidation while still allowing tissue penetrating members 140 to penetrate the film as is described below. Film 177 can comprise various water and/or oxygen impermeable polymers which are desirably configured to be biodegradable in the small intestine and/or to pass inertly through the digestive tract. It may also have a multi-ply construction with particular layers selected for impermeability to a given substance, e.g., oxygen, water vapor etc. In use, embodiments employing protective film 177 serve to increase the shelf life of therapeutic agent 101 in tissue penetrating members 140, and in turn, the shelf life of device 110. Collectively, support platform 175 attached tissue penetrating members 140, well structure 176, and film 177 can comprise a delivery assembly 178. Delivery assemblies 178 having one or more drugs or therapeutic agents 101 contained within tissue penetrating member 40 or other drug delivery means can be pre-manufactured, stored and subsequently used for the manufacture of device 110 at a later date. The shelf life of assembly 178 can be further enhanced by filling cavity 176c of the sealed assembly 178 with an inert gas such as nitrogen.

Referring back to FIGS. 16a and 16b, assemblies 178 can be positioned on one or both faces 172f of balloon 172. In preferred embodiments, assemblies 178 are positioned on both faces 172f (as shown in FIG. 16a) so as to provide a substantially equal distribution of force to opposite sides of the intestinal wall IW upon expansion of balloon 172. The assemblies 178 may be attached to faces 172f using adhesives or other joining methods known in the polymer arts. Upon expansion of balloon 172, TPMs 140 penetrate through film 177, enter the intestinal wall IW and are retained there by retaining elements 143 and/or other retaining features of TPM 140 (e.g., an inverse tapered shaft 144t) such that they detach from platform 175 upon deflation of balloon 172.

In various embodiments, one or more of balloons 130, 160 and 172 can be packed inside capsule 120 in a folded, furled or other desired configuration to conserve space within the interior volume 124v of the capsule. Folding can be done using preformed creases or other folding feature or method known in the medical balloon arts. In particular embodiments, balloon 130, 160 and 172 can be folded in selected orientations to achieve one or more of the following: i) conserve space, ii) produce a desired orientation of a particular inflated balloon; and iii) facilitate a desired sequence of balloon inflations. The embodiments shown in FIGS. 15a-15f illustrate an embodiment of a method of folding and various folding arrangements. However, it should be appreciated that this folding arrangement and the resulting balloon orientations are exemplary and others may also be used. In this and related embodiments, folding can be done manually, by automated machine or a combination of both. Also in many embodiments, folding can be facilitated by using a single multi-balloon assembly 7 (herein assembly 7) comprising balloons 130, 160, 170; valve chamber 158 and assorted connecting tubings 162 as is shown in the embodiments of FIGS. 13a and 13b. FIG. 13a shows an embodiment of assembly 7 having a single dome construction for balloon 130, while FIG. 13b shows the embodiment of assembly 7 having dual balloon/dome configuration for balloon 130. Assembly 7 can be fabricated using a thin polymer film which is vacuum-formed into the desired shape using various vacuum forming and other related methods known in the polymer processing arts. Suitable polymer films include polyethylene films having a thickness in the range of about 0.003 to about 0.010", with a specific embodiment of 0.005". In preferred embodiments, the assembly is fabricated to have a unitary construction so as to eliminate the need for joining one or more components of the assembly (e.g., balloons 130,160, etc.). However, it is also contemplated for assembly 7 to be fabricated from multiple portions (e.g., halves), or components (e.g., balloons) which are then joined using various joining methods known in the polymer/medical device arts.

Figure 15A:
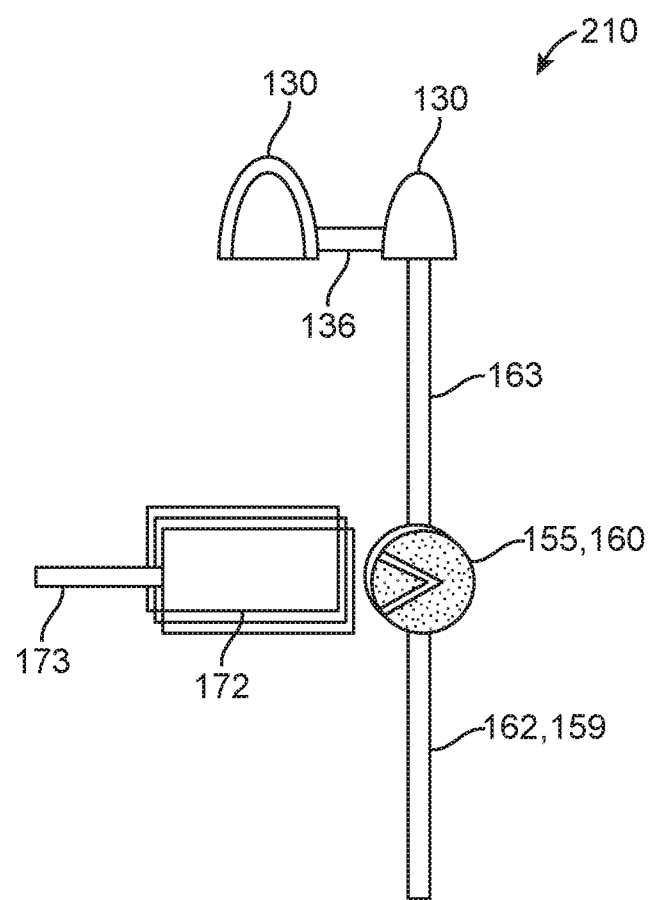
FIGS. 15a-15g are lateral views illustrating a method for folding of the multiple balloon assembly, the folding configuration in each figure applies to both single and dual dome configurations of the deployment balloon, with the exception that FIG. 15c, pertains to a folding step unique to dual dome configurations.
Figure 15B:
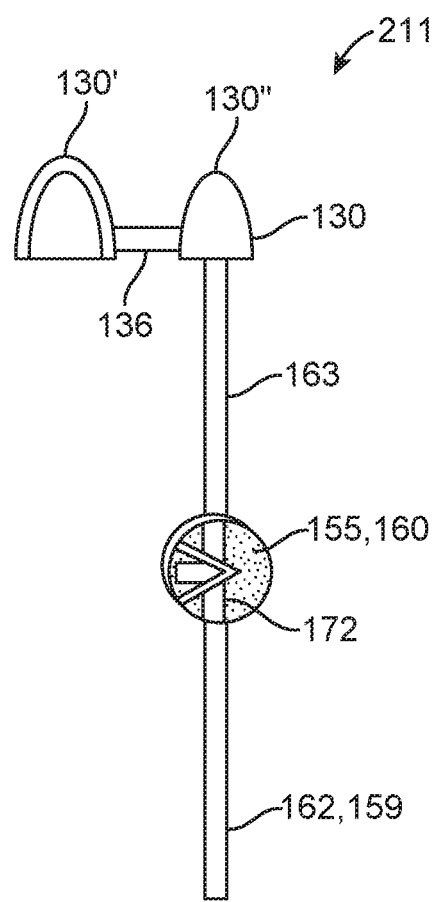
Figure 15C:
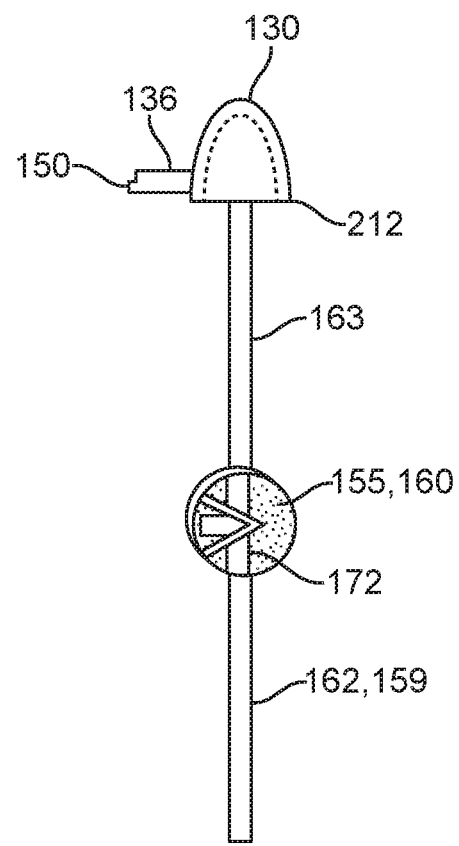
Figure 15D:
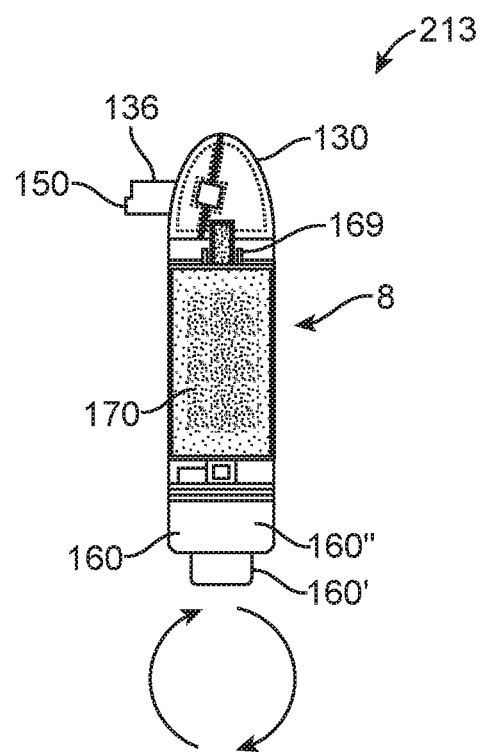
Figure 15E:
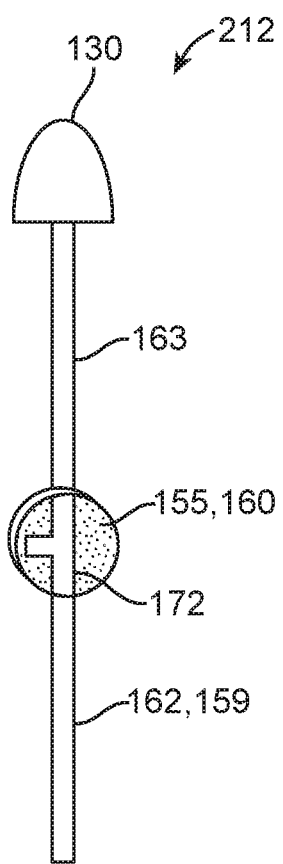
Figure 15F:
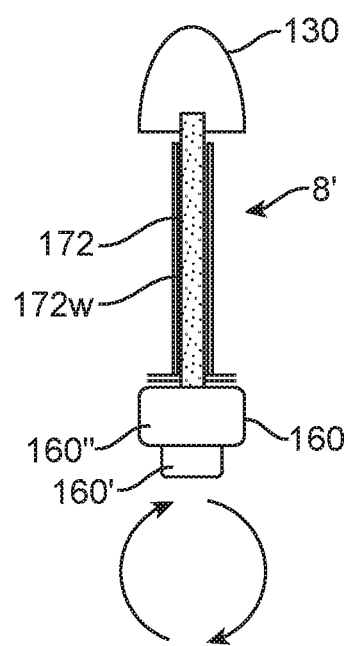
Figure 15G:
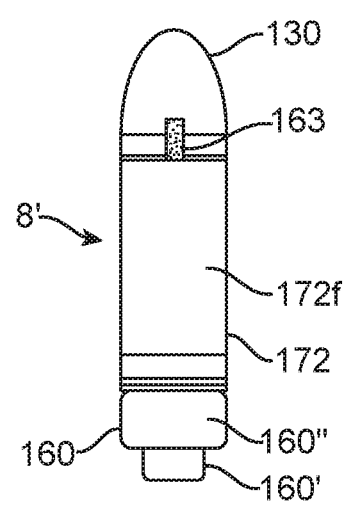

Referring now to FIGS. 15a-15f, 16a-16b and 17a-17b, in a first folding step 210, balloon 160 is folded over onto valve fitting 158 with balloon 172 being flipped over to the opposite side of valve fitting 158 in the process (see FIG. 15a). Then in step 211, balloon 172 is folded at a right angle to the folded combination of balloon 160 and valve 158 (see FIG. 15b). Then, in step 212 for dual dome embodiments of balloon 130, the two halves 130' and 130" of balloon 130 are folded onto each other, leaving valve 150 exposed (see FIG. 15c, for single dome embodiments of balloon 130, is folded over onto itself see FIG. 15e). A final folding step 213 can be done whereby folded balloon 130 is folded over 180° to the opposite side of valve fitting 158 and balloon 160 to yield a final folded assembly 8 for dual dome configurations shown in the FIG. 15e and a final folded assembly 8' for single dome configurations shown in FIGS. 15e and 15f. One or more delivery assemblies 178 are then be attached to assembly 8 in step 214 (typically two the faces 72f of balloon 72) to yield a final assembly 9 (shown in the embodiments of FIGS. 16a and 16b) which is then inserted into capsule 120. After an insertion step 215, the final assembled version of device 110 with inserted assembly 9 is shown FIGS. 17a and 17b.

Figure 20A:
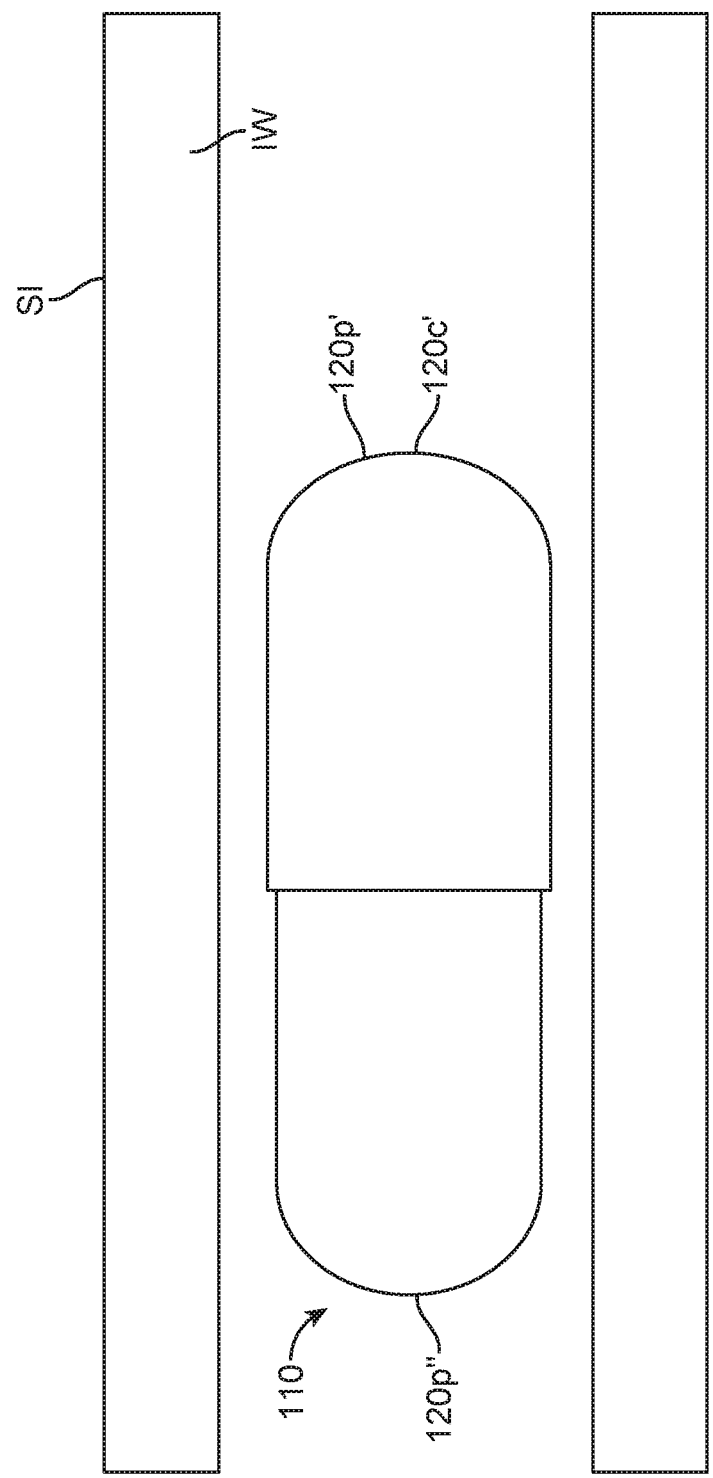
Figure 20B:
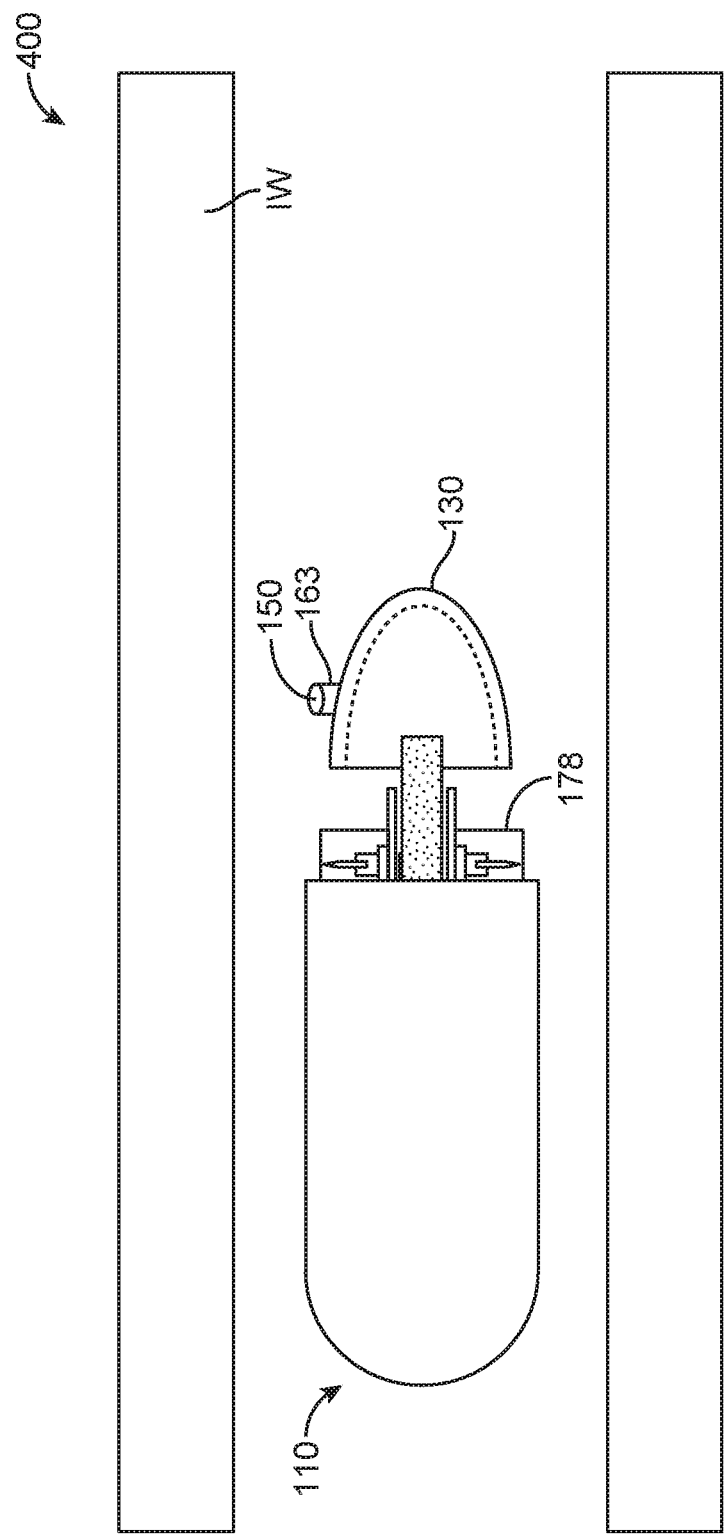
Figure 20C:
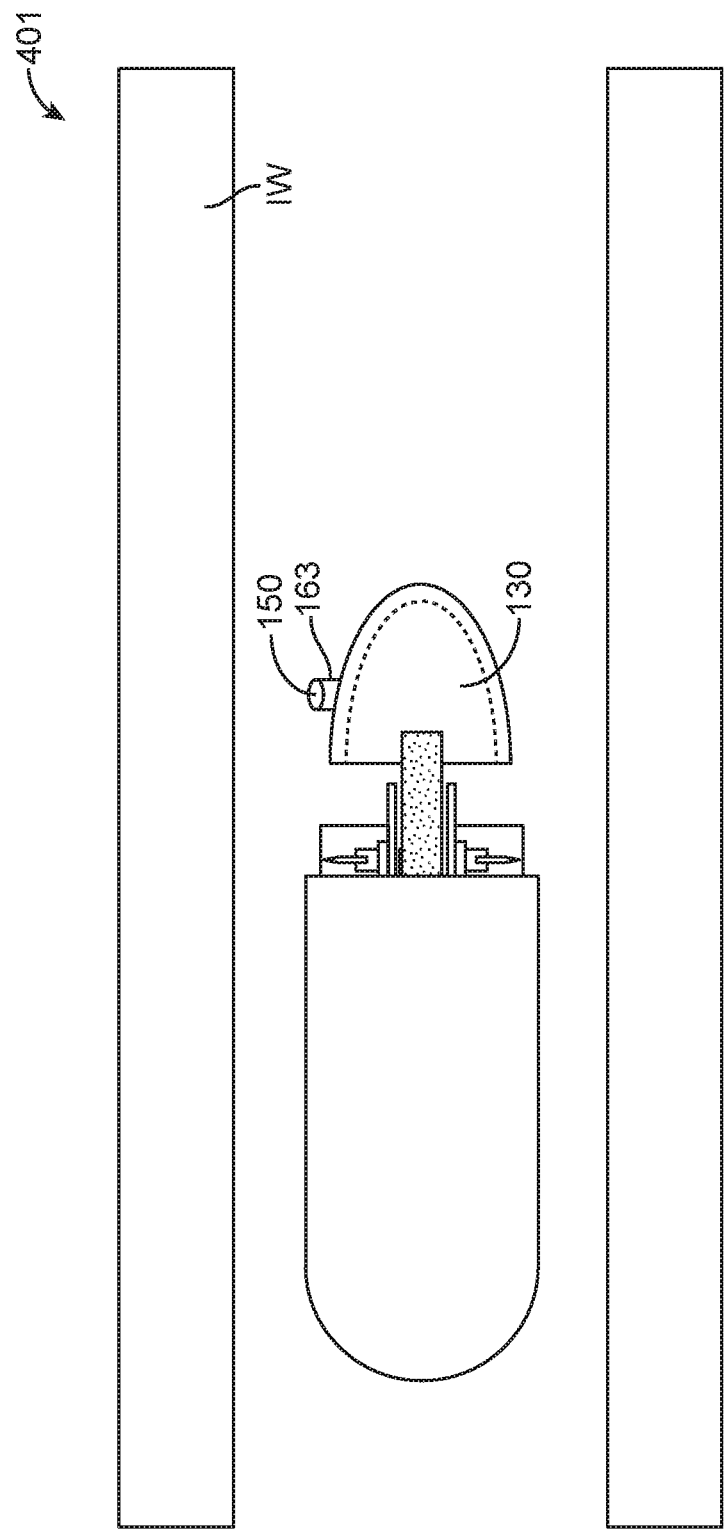
Figure 20E:
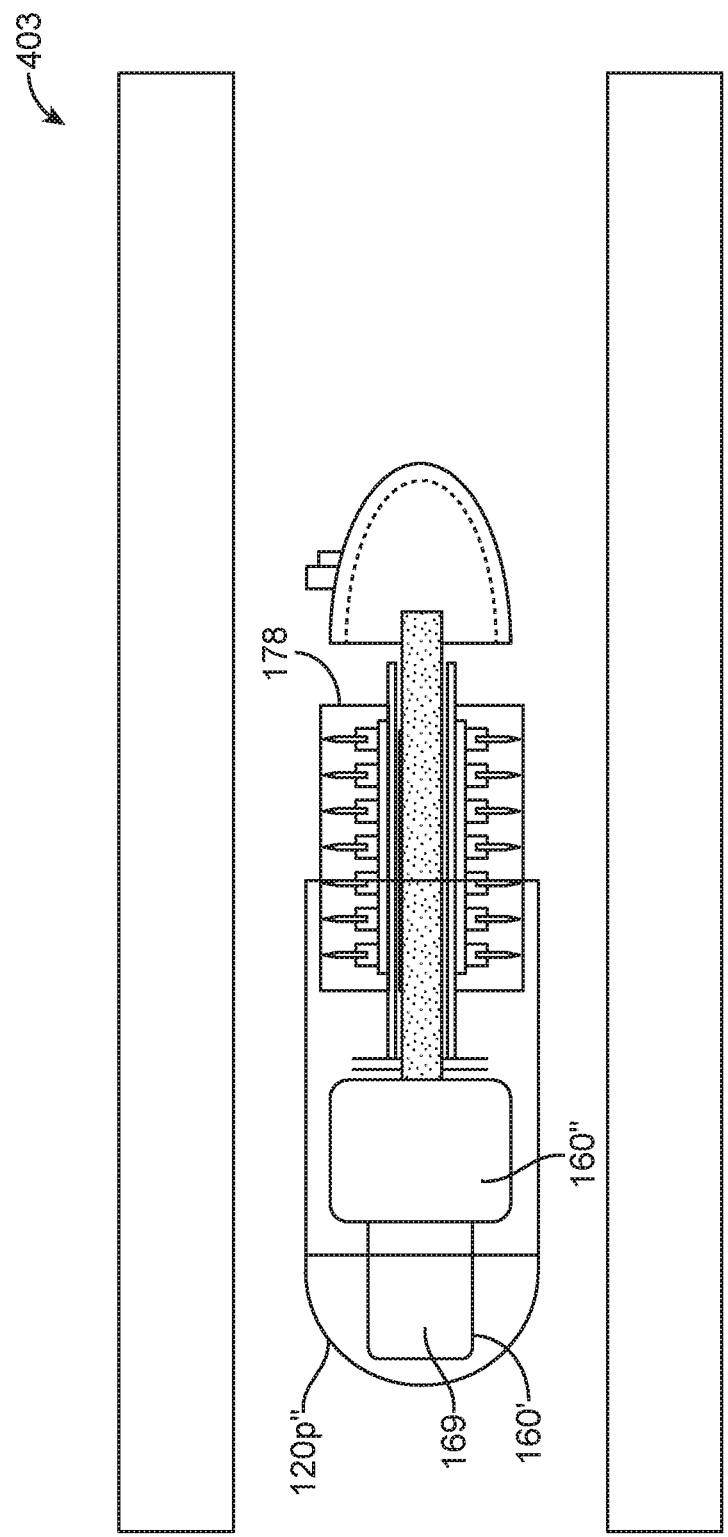
Figure 20F:
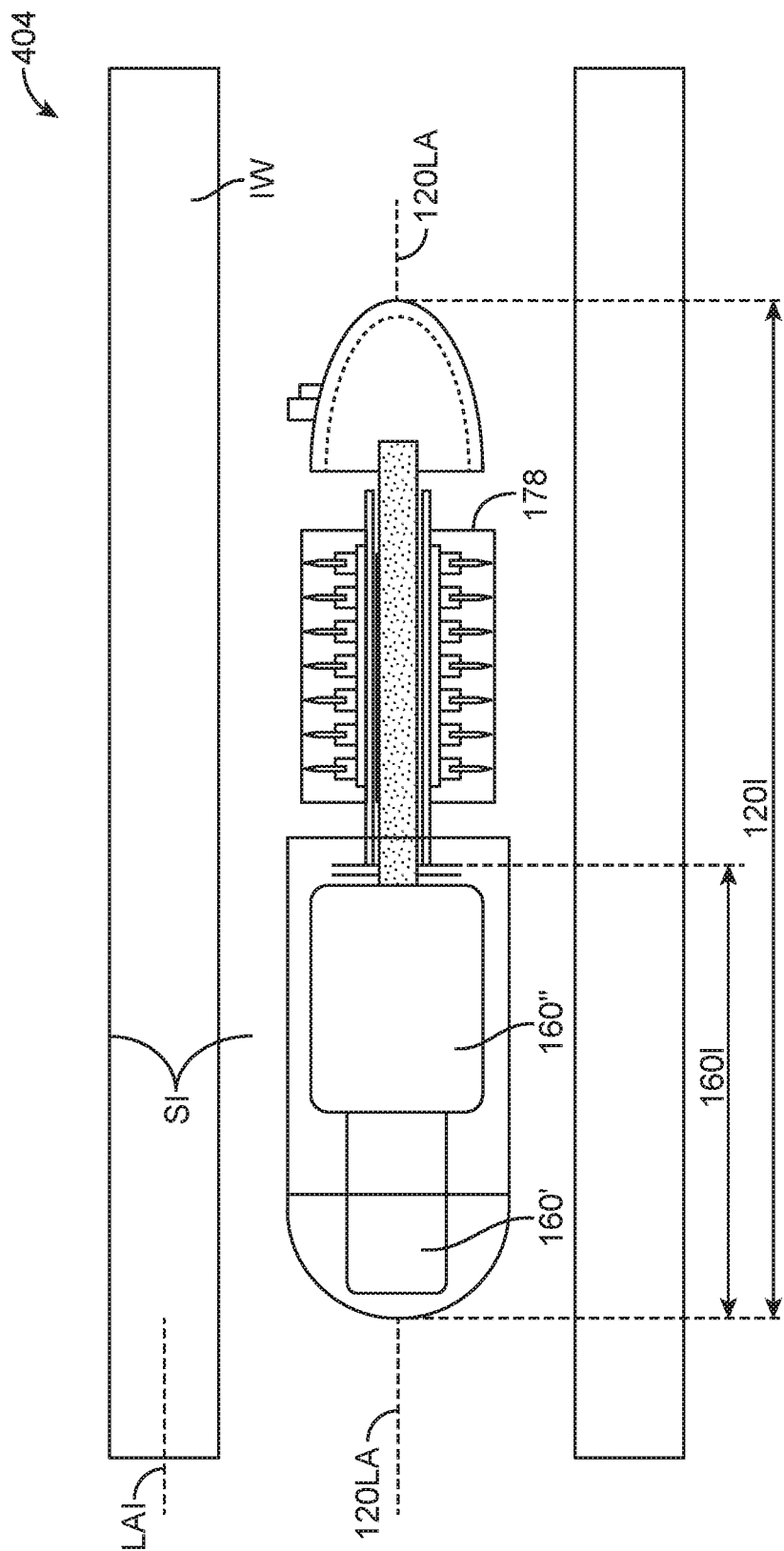
Figure 20G:
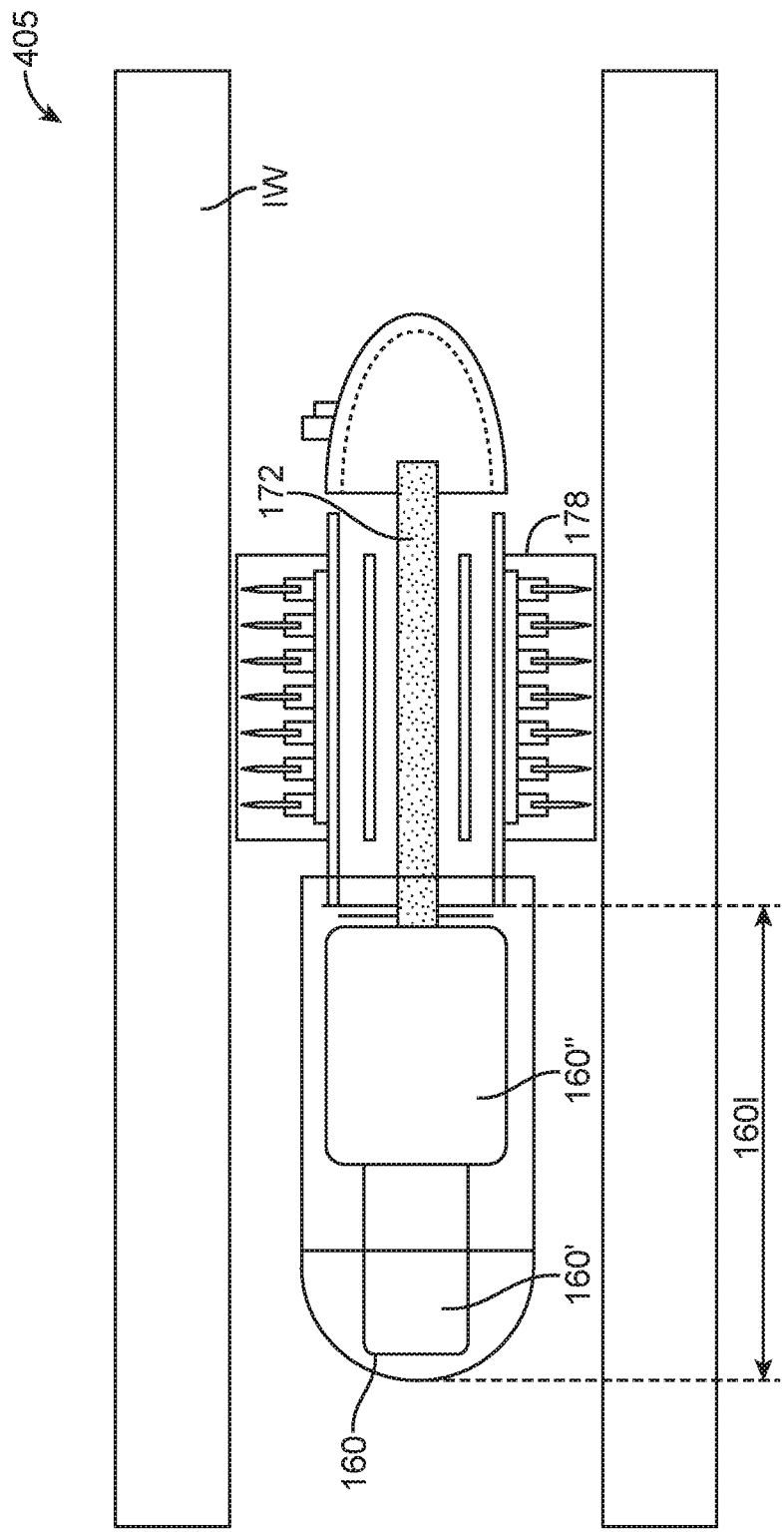
Figure 20H:
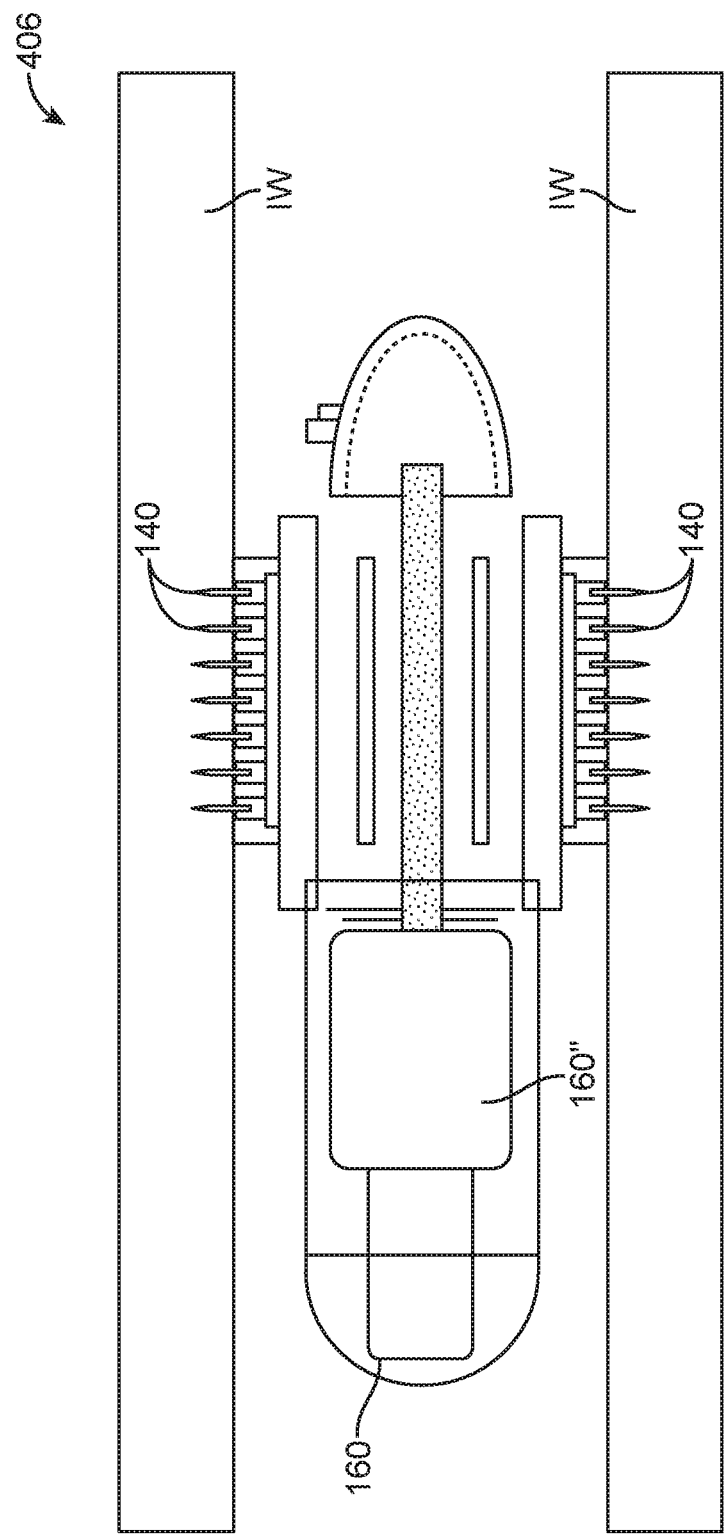
Figure 20I:
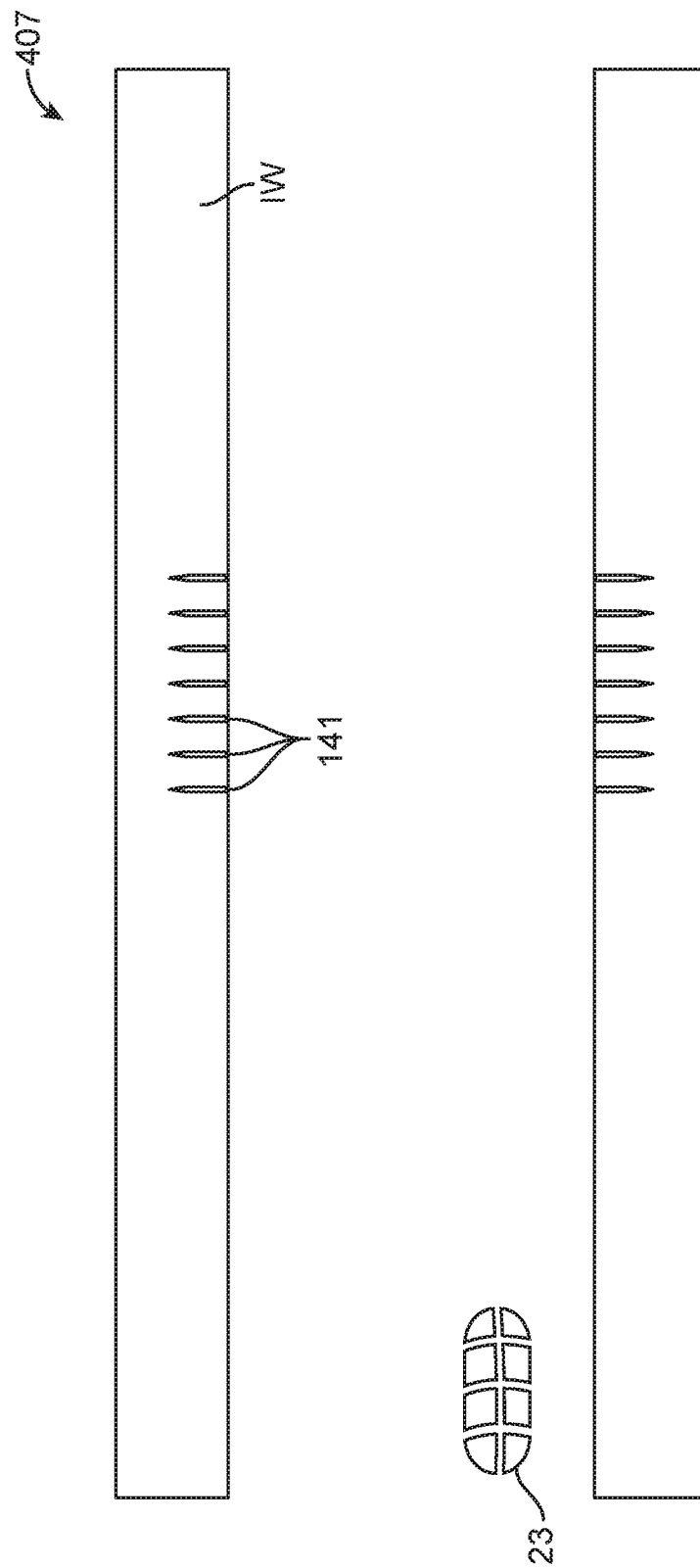

Referring now to FIGS. 20a-20i, a description will be provided of a method of using device 110 to deliver medication 101 to a site in the GI tract such as the wall of the small or large intestine. It should be appreciated that the steps and there order is exemplary and other steps and orders also contemplated. After device 110 enters the small intestine SI, the cap coating 120c' is degraded by the basic pH in the upper small intestine causing degradation of cap 120p' as shown in step 400 in FIG. 20b. Valve 150 is then exposed to fluids in the small intestine causing the valve to begin degrade as is shown in step 401 in FIG. 20c. Then, in step 402, balloon 130 expands (due to generation of gas 169) as shown in FIG. 20d. Then, in step 403, section 160' of balloon 160 begins to expand to start to push assembly 178 out of the capsule body as shown in FIG. 20e. Then, in step 404, sections 160' and 160" of balloon 160 become fully inflated to completely push assembly 178 out of the capsule body extending the capsule length 120l so as to serve to align capsule lateral axis 120AL with the lateral axis of the small intestine LAI as shown in FIG. 20f. During this time, valve 155 is beginning to fail from the increased pressure in balloon 60 (due to the fact that the balloon has fully inflated and there is no other place for gas 169 to go). Then, in step 405, valve 155 has completely opened, inflating balloon 172 which then pushes the now completely exposed assembly 178 (having been pushed completely out of body 120p") radially outward into the intestinal wall IW as shown in FIG. 20g. Then, in step 406, balloon 172 continues to expand to now advance tissue penetrating members into the intestinal wall IW as shown in FIG. 20h. Then, in step 407, balloon 172, (along with balloons 160 and 130) has deflated pulling back and leaving tissue penetrating members retained in the intestinal wall IW. Also, the body portion 120p" of the capsule has completely degraded (due to degradation of coating 120c") along with other biodegradable portions of device 110. Any portion not degraded is carried distally through the small intestine by peristaltic contraction from digestion and is ultimately excreted.

APPENDICES/EXAMPLES

Various embodiments of the invention are further illustrated with reference to the following appendices/examples. It should be appreciated that these examples are presented for purposes of illustration only and that the invention is not to be limited to the information or the details therein.

Appendix 1

Modeling of Alirocumab Serum Concentration Vs Time

The following assumptions and/or data were used in modelling Alirocumab Serum Concentrations vs Time:

The subcutaneous dosing schedule is 150 mg every week, SC (subcutaneous), every two weeks, this corresponds to a daily dosing schedule of approximately 21.4 mg per day using embodiments of the invention.

Monoclonal antibody was obtained from Regeneron/Sanofi. It targets pro-protein convertase subtilisin/kexin type 9 (PCSK9) to lower low density lipoproteins (LDLs).

Pharmacokinetic parameters were obtained from: Lunven, C., Paehler, T., Poitiers, F., et al. "A randomized study of the relative pharmacokinetics, pharmacodynamics, and safety of Alirocumab, a fully human monoclonal antibody to PCSK9, after single subcutaneous administration at three different injection sites in healthy subjects." *Cardiovascular Therapeutics*, 2014, 32:297.301.

No ka was reported, but 0.5 day$^{-1}$ was chosen so that $T_{max}$ was 4.3 days.

The study reported PK parameters for three different sites of injection and found that all three were comparable. For this single simulation, the parameters used were averages of the three.

When steady state is reached for simulated daily dosing using embodiments of the invention, drug concentrations ranged from 10.06 mg/L to 20.05 mg/L, resulting in an average of 15.06 mg/L.

When using embodiments of the invention, daily dosing at doses of approximately 10.5 mg every which corresponded approximately to the 150 mg biweekly dose.

For daily dosing using embodiments of the invention, one can dose a smaller amount daily and receive the pharmacokinetic profile shown in FIG. 22b.

Once steady state is reached, concentrations of Alirocumab ranged from 15.41 mg/L to 15.47 mg/L, with an average steady state concentration of 15.44 mg/L above the 15.06 value for subcutaneous injections every two weeks.

This lower day to day variation in drug concentrations may prevent adverse events and anti-drug antibody formation, and the higher trough concentrations ensure that biological activity of Alirocumab is maintained.

Appendix 2

Model and Calculations Used for Calculation of Steady State Fluctuation in Alirocumab Serum Concentrations % Steady State Fluctuation is a metric which provides an indication of how much variation there is in the patient's plasma/serum concentration of drug over time. It is desirable to minimize steady state fluctuation for multiple reasons. Firstly, drug concentrations that are higher than necessary for pharmacologic activity are more likely to result in adverse events. In addition to specific effects for PCSK9 antibodies, such as myalgia, neurocognitive events and ophthalmologic events for PCSK9, antibody therapies cause anti-drug antibody production. These anti-drug antibodies target the drug and may neutralize them by blocking binding sites or marking the drugs for destruction. A patient who develops anti-drug antibodies to a drug will no longer respond to that drug and must be placed on a different regimen. On the other hand, drug concentrations that are lower than necessary for pharmacologic activity are also not desired. There is a greater chance of no pharmacologic activity during these periods, and thus lower drug efficacy. It is ideal to maintain a constant, steady level of pharmacologic activity in order to effectively treat the targeted disorder.

TABLE 1

% Steady State Fluctuation for Alirocumab

|  | Alirocumab |
| --- | --- |
| Current SC dosing | 66.33% |
| Rani dosing | 0.39% |

Calculations were made for % Steady State Fluctuation for the three antibodies shown in Table 1. Values were determined using the existing pharmacokinetic simulations described in Appendix 1. The specific formula used to calculate % Steady State Fluctuation is shown below:

$$\frac{C_{ss,peak} - C_{ss,trough}}{C_{ss,avg}} * 100 = \% \text{ steady state fluctuation}$$

The above equation calculates the difference between peak steady state concentration ($C_{ss,peak}$) and trough steady state concentration ($C_{ss,trough}$) and divides by the average steady state concentration ($C_{ss,avg}$) to yield the percent change of serum drug concentrations relative to the average steady state drug concentration. Steady state fluctuation serves as a quantitative measure of how much we can expect serum drug concentrations to change in single dosing period.

From the data, it is evident that daily dosing using embodiments of the invention allows much lower steady state fluctuation for the same drugs than subcutaneous dosing. In addition to the expected benefits of less frequent, less intense adverse events and maintenance of pharmacologic activity, dosing via injection into the small intestine using embodiments of the invention avoids the injection site reactions that may occur in subcutaneous dosing.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device and therapeutic preparations (e.g., in the form of a tissue penetrating member) can be sized and otherwise adapted (e.g., dosage adjusted for therapeutic preparations) for various pediatric and neonatal applications as well as various veterinary applications. Also those skilled in the art will recognize, or be able to ascertain using no more than routine experimentation, numerous equivalents to the specific devices and methods described herein. Such equivalents are considered to be within the scope of the present invention and are covered by the appended claims below.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for reducing a low-density lipoprotein cholesterol (LDL-C) level in a patient having hypercholesterolemia, the method comprising: providing a solid anti-proprotein convertase subtilsin-kexin type 9 (PCSK9)-antibody (AP-antibody) dosage shaped as a tissue penetrating member, wherein the AP-antibody is selected from the group consisting of Alirocumab, Evolocumab and Bococizumab and wherein a dose of AP-antibody in the solid AP dosage is in a range from about 1 to 15 mg; penetrating the solid dosage AP-antibody into an intestinal wall after oral ingestion by the application of force on the tissue penetrating member such that the tissue penetrating member is retained in the intestinal wall or surrounding tissue; and releasing the AP-antibody into the blood stream from the solid dosage AP-antibody in the intestinal wall or surrounding tissue to reduce the LDL-C level by binding of PCSK9 molecules by the released dosage of PCSK9 antibody.

2. A method for treating hypercholesterolemia by in a patient by reducing the patient's low-density lipoprotein cholesterol (LDL-C) level, the method comprising: providing a solid anti-proprotein convertase subtilsin-kexin type 9 (PCSK9),-antibody (AP-antibody) dosage shaped as a tissue penetrating member, wherein the AP-antibody is selected from the group consisting of Alirocumab, Evolocumab and Bococizumab and wherein a dose of AP-antibody in the solid AP dosage is in a range from about Ito 15 mg; penetrating the solid dosage AP-antibody into an intestinal wall after oral ingestion by the application of force on the tissue penetrating member such that the tissue penetrating member is retained in the intestinal wall or surrounding tissue; releasing the AP-antibody into the blood stream from the solid dosage AP-antibody in the intestinal wall or surrounding tissue to reduce the LDL-C level by binding of PCSK9 molecules by the released dosage of PCSK9 antibody; monitoring an LDL-C level in the patient; and adjusting a dose of the AP-antibody in response to the monitored LDL-C level in the patient.

3. A method for treating a cardiovascular condition in a patient caused by hypercholesterolemia by reducing the patient's low-density lipoprotein cholesterol (LDL-C) level, the method comprising: providing a solid anti-PCSK9 antibody (AP-antibody) dosage shaped as a tissue penetrating member, wherein the AP-antibody is selected from the group consisting of Alirocumab, Evolocumab and Bococizumab and wherein a dose of AP-antibody in the solid AP dosage is in a range from about 1 to 15 ma; penetrating the solid dosage AP-antibody into an intestinal wall after oral ingestion by the application of force on the tissue penetrating member such that the tissue penetrating member is retained in the intestinal wall or surrounding tissue; releasing the AP-antibody into the blood stream from the solid dosage AP-antibody in the intestinal wall or surrounding tissue to reduce the LDL-C level by binding of PCSK9 molecules by the released dosage of PCSK9 antibody; monitoring an LDL-C level in the patient; and adjusting a dose of the AP antibody in response to the monitored LDL-C level in the patient.

4. The method of claim 1, wherein the force is a mechanical force.

5. The method of claim 1, wherein when inserted into the intestinal wall of a patient on a daily basis, the preparation results in a percent steady state fluctuation in plasma concentration of AP-antibody in the patient in a range of about 0.12 to about 0.39%.

6. The method of claim 1, wherein the surrounding tissue is a peritoneal wall.

7. The method of claim 1, further comprising performing genetic testing on the patient to determine a preferred AP-antibody to be delivered to the patient.

8. The method of claim 7, wherein the preferred AP-antibody is based on effectiveness in reducing LDL-C levels in the patient.

9. The method of claim 7, wherein the preferred AP-antibody is selected based on that having the fewest or least severe side effects in the patient.

10. The method of claim 7, wherein the preferred AP-antibody is Alirocumab, Evolocumab and Bococizumab.

11. The method of claim 1, further comprising: monitoring an LDL-C level in the patient.

12. The method of claim 11, further comprising: adjusting a dose of the AP antibody in response to the monitored LDL-C level in the patient.

13. The method of claim 12, wherein the dose of AP-antibody is adjusted to produce a selected level of reduction in an LDL-C level in the patient.

14. The method of claim 13, wherein the selected level of LDL-C reduction is at least 30%.

15. The method of claim 13, wherein the selected level of LDL-C reduction is in a range of about 40 to 60 mg/dl.

16. The method of claim 11, further comprising decreasing a dose of the orally ingested AP antibody when the LDL-C level in the patient falls below a threshold level.

17. The method of claim 16, wherein the threshold level is <25 mg/dl.

18. The method of claim 1, wherein the AP-antibody released into the blood stream from the solid dosage AP-antibody reaches a Cmax in a shorter time period than a time period to achieve a Cmax for an extravascularly injected dose AP-antibody.

19. The method of claim 18, wherein a tmax for the AP-antibody released from the solid dosage AP-antibody is less than 50% of a tmax for the extravascularly injected dose of AP-antibody.

20. The method of claim 18, wherein a tmax for the AP-antibody released from the solid dosage AP-antibody is less than 10% of a tmax for the extravascularly injected dose of AP-antibody.

21. The method of claim 1, wherein an immune response in the patient to the AP-antibody is minimal.

22. The method of claim 21, wherein a white blood cell count in the patient's serum is increased by no more than about 10% in response to release of the AP-antibody into the patient's blood stream.

23. The method of claim 21, wherein a serum titer of patient antibodies to the AP-antibody is increased by no more than about 10% in response to release of the AP-antibody into the patient's blood stream.

24. The method of claim 21, wherein a serum titer of interleukin-7 is increased by no more than about 10% in response to release of the AP-antibody into the patient's blood stream.

25. The method of claim 1, wherein an immune response in the patient to the AP-antibody is reduced as compared to delivery of the AP-antibody by an intramuscular or sub-dermal injection.

26. The method of claim 25, wherein the immune response in the patient to the AP-antibody is reduced by an amount in the range of about two to thirty times as compared to an intramuscular or sub-dermal injection.

27. The method of claim 2, wherein the dose of AP-antibody is adjusted to produce a selected level of reduction in LDL-C level in the patient.

28. The method of claim 27, wherein the selected level of LDL-C reduction is at least 30%.

29. The method of claim 27, wherein the selected level of LDL-C reduction is in a range of about 40 to 60 mg/dl.

30. The method of claim 2, further comprising decreasing a dose of the AP antibody when the LDL-C level in the patient falls below a threshold level.

31. The method of claim 30, wherein the threshold level is <25 mg/dl.

32. The method of claim 2, wherein an immune response in the patient to the AP-antibody is minimal.

33. The method of claim 32, wherein a white blood cell count in the patient's serum is increased by no more than about 10% in response to release of the AP-antibody into the patient's blood stream.

34. The method of claim 32, wherein a serum titer of patient antibodies to the AP-antibody is increased by no more than about 10% in response to release of the AP-antibody into the patient's blood stream.

35. The method of claim 32, wherein a serum titer of interleukin-7 is increased by no more than about 10% in response to release of the AP-antibody into the patient's blood stream.

36. The method of claim 2, wherein an immune response in the patient to the AP-antibody is reduced as compared to delivery of the AP-antibody by an intramuscular or sub-dermal injection.

37. The method of claim 36, wherein the immune response in the patient to the AP-antibody is reduced by an amount in the range of about two to thirty times as compared to an intramuscular or sub-dermal injection.

38. The method of claim 2, wherein the force is a mechanical force.

39. The method of claim 38, wherein the force is a mechanical force.

* * * * *